(12) United States Patent
Mauro

(10) Patent No.: US 10,031,060 B2
(45) Date of Patent: Jul. 24, 2018

(54) CONTINUOUS, REAL TIME MONITOR FOR AIRBORNE DEPLETED URANIUM PARTICLES IN THE RESPIRATORY RANGE AND CORRESPONDING METHOD OF USE

(71) Applicant: John Mauro & Associates, LLC, Red Bank, NJ (US)

(72) Inventor: John Mauro, Red Bank, NJ (US)

(73) Assignee: MAURO & ASSOCIATES, LLC, Red Bank, NJ (US)

( * ) Notice: Subject to any disclaimer, the term of this patent is extended or adjusted under 35 U.S.C. 154(b) by 0 days.

(21) Appl. No.: 15/649,626

(22) Filed: Jul. 13, 2017

(65) Prior Publication Data

US 2018/0017477 A1    Jan. 18, 2018

Related U.S. Application Data

(60) Provisional application No. 62/361,603, filed on Jul. 13, 2016.

(51) Int. Cl.
| | |
|---|---|
| *G01N 15/06* | (2006.01) |
| *G01N 15/02* | (2006.01) |
| *G01N 23/20* | (2018.01) |

(52) U.S. Cl.
CPC ......... *G01N 15/0618* (2013.01); *G01N 15/02* (2013.01); *G01N 23/20* (2013.01);
(Continued)

(58) Field of Classification Search
CPC .... G01N 15/0618; G01N 15/02; G01N 23/20; G01N 2015/0045; G01N 2223/00; G01N 2223/638; G01N 2223/641; G01N 2223/652; G21C 17/00; G21C 17/06; G01T 1/178; G01T 7/04; G01T 1/38; G06F 17/18

See application file for complete search history.

(56) References Cited

U.S. PATENT DOCUMENTS

| | | |
|---|---|---|
| 3,914,602 A | 10/1975 | Goldstein |
| 4,078,178 A | 3/1978 | Lowes |
| | (Continued) | |

OTHER PUBLICATIONS

EPA 2006, Depleted Uranium Technical Brief, EPA 402-R-06-011, pp. 1-48, US EPA, Washington, DC, Dec. 2006.
(Continued)

*Primary Examiner* — Jack W Keith
*Assistant Examiner* — Lily Crabtree Garner

(57) ABSTRACT

A continuous alpha monitor includes an air intake mechanism, which in turn includes an air mover, an air intake prefilter that limits particulates in the air intake mechanism to an aerodynamic diameter of 10 microns or less, and a particle detector mounted downstream of the air intake prefilter, the air particle detector providing a first airborne dust concentration and a first distribution of aerodynamic diameters of particulates in air passing the prefilter, the particulates including depleted uranium particulates. The monitor further includes a movable sample filter web that collects the particulates; a solid state detector that detects alpha radiation emitted by the collected particulates; a processor that executes machine instructions embodied on a non-transient computer-readable storage medium to compute a dust loading on the sample filter web; and the processor computes an indication of alpha concentration detected by the solid state detector.

20 Claims, 22 Drawing Sheets

(52) U.S. Cl.
CPC . *G01N 2223/638* (2013.01); *G01N 2223/641* (2013.01); *G01N 2223/652* (2013.01)

(56) References Cited

U.S. PATENT DOCUMENTS

| | | | |
|---|---|---|---|
| 4,262,203 A | 4/1981 | Overhoff |
| 4,295,045 A | 10/1981 | Minami |
| 4,400,621 A | 8/1983 | Kiefer |
| 4,454,587 A | 6/1984 | Kiefer |
| 4,607,165 A | 8/1986 | Burghoffer |
| 4,700,067 A | 10/1987 | Carossi |
| 4,805,827 A | 2/1989 | Coffman |
| 4,888,485 A | 12/1989 | Becker |
| 5,124,938 A | 6/1992 | Pellitier |
| 5,235,190 A | 8/1993 | Tucker |
| 5,514,872 A | 5/1996 | Bolton |
| 5,552,610 A | 9/1996 | McIsaac |
| 5,561,515 A | 10/1996 | Hairston |
| 5,654,899 A | 8/1997 | Leonard |
| 6,822,235 B2 | 11/2004 | Ryden |

OTHER PUBLICATIONS

Parkhurst, Capstone Depleted Uranium Aerosols: Generation and Characterization, PNNL-14168, pp. B1-B33; D1-D41; E1-E25, US Department of the Army, Washington, DC, Oct. 2004.
ATSDR 2013, Toxicological Profile for Uranium, pp. 17-262, US Department of Health and Human Services, Washington DC, Feb. 2013.
NCRP 94, Exposure of the Population of the United States and Canada from Background Radiation, NCRP Report No. 94, p. 61, Washington DC, 1994.
EPA 1999, Cancer Risk Coefficients for Environmental Exposure to Radionuclides—Federal Guidance Report No. 13, EPA 402-R-99-001, excerpt from accompanying CD, US EPA, Sep. 1999.
ICRP 1998, The ICRP Database of Dose Coefficients: Workers and Members of the Public, Tables from CD, referenced in ICRP 68, Dose Coefficients for Intakes of Radionuclides by Workers, Annals of the ICRP vol. 24, No. 4, Tables from Associated CD, International Commission on Radiation Protection, ISSN 0146-6453, Pergamon, 1994 and ICRP 72, Age-Dependent Doses to the Members of the Public from Intake of Radionuclides—Part 5 Compilation of Ingestion and Inhalation Coefficients, Annals of the ICRP vol. 26, No. 1, ICRP, Pergamon, 1995.
Sarap, et al., Environmental Radioactivity in Southern Serbia at Locations Where Depleted Uranium Was Used, Radioactivity in Southeren Serbia, 65: pp. 189-197, Arh big Rada Toksikol, Belgrade, Serbia, 2014.
Kennedy, et al., Residual Radioactive Contamination form Decommissioning, NUREG/CR-5512, PNL-7994, vol. 1, Pacific Northwest Laboratory, Richland, Washington, USA, Oct. 1992.
Hindin, et al., Tetratogenicity of Depleted uranium Aerosols: A Review from an Epidemiological Perspective, Environmental Health: A Global Access Science Source, 4:17, pp. 1-9, USA, Aug. 2005.
Crean, et al., Remediation of Soils Contaminated with Particulate Depleted Uranium by Multi-Stage Chemical Extraction, Journal of Hazardous Materials, 263, pp. 382-390, Elsevier BV, United Kingdom, 2013.
Mohammed, et al., Assessment of Depleted Uranium Contamination in Selective Iraqi Soils, Journal of Al-Nahrain University, vol. II(1). pp. 74-81, Baghdad, Iraq, Apr. 2008.
Exposure of the Population in the United States and Canada from Natural Background Radiation, NCRP Report No. 94, p. 61, USA, 2001.
Sources and Effects of Ionizing Radiation, UNSCEAR 1993 Report to the General Assembly, pp. 54, 73, United Nations, New York, USA 1993.
Huang, et al., Influence of Dust Loading on the Alpha-Particle Energy Resolution of Continuous Air Monitors for Thin Deposits of Radioactive Aerosols, Health Physics 83(6), pp. 884-891, USA, 2002.
Zhang, et al., Measurements of Dust Deposition Velocity in a Wind-Tunnel Experiment, Atmospheric Chemistry and Physics, 14, pp. 8869-8882, Copernicus Publications, United Kingdom, Apr. 2014.
Choy, et al., Removal of Depleted Uranium from Contaminated Soils, Journal of Hazardous Materials, 136, Abstract, Elsivier BV, United Kingdom, Aug. 2008.
Stevens, et al., Effect of Particle Size and Dust Loading on the shape of Alpha Pulse-Height Spectra of Air Sample Filters, AERE-R-4249, Abstract, United Kingdom, 1963.
Manickam, et al., Method design and Validation for the Determination of Uranium Levels in Human Urine Using High-Resolution Alpha Spectrometry, Journal of Environmental Radioactivity, 99(3), Abstract, Elsevier BV, United Kingdom, Oct. 2007.
Besic, et al., Meta-analysis of Depleted Uranium Levels in the Balkan Region, Journal of Environmental Radioactivity, 172, pp. 207-217, Elsevier BV, United Kingdom, Apr. 2017.
Cheng, et al., Physicochemical Characterization of Capstone Depleted Uranium Aerosols II: Particle Size Distributions as a Function of Time, Health Physics, vol. 96, No. 3, pp. 266-275, Health Physics Society, USA. Mar. 2009.
Alpha-7A Alpha Particulate, Product Specifications, available at www.thermo.com/mp, Thermo Scientific, Fairfax, VA, USA 2007.
Ebinger, et al., Depleted Uranium Risk Assessment at Abeerden Proving Ground, American Defense Preparedness Associates, 19th Environmental Symposium and Exhibition, pp. 1-12, USA, Mar. 23, 1998.
Depleted Uranium Munitions Act. H.R. 2410, 109th Congrress, 1st Session, pp. 1-9, USA, May 2005.
Rostker, Environmental Exposure Report, Sections I-III, and IV, pp. 10-11, US DOD, Washington, DC, Dec. 2000.
Garamone, Study Finds Little Risk from Depleted-Uranium Particles, pp. 1-2, American Forces Press Service, USA, Oct. 2004.
Holmes, et al., Aerosol Sampling System for Collection of Capstone Depleted Uranium Particles in a High-Energy Environment, Health Physics, vol. 93, No. 3, pp. 221-238, Health Physics Society, USA, Mar. 2009.
ICAM Alpha/Beta Air Monitor, Product Brochure, available at www.canberra.com, pp. 1-12, Canberra, USA, 2010.
Krupka, et al., Physiochemical Characterization of Capstone Depleted Uranium Aerosols III: Morphologic and Chemical Oxide Analyses, Health Physics, vol. 96. No. 3, pp. 276-292, Health Physics Society, USA, Mar. 2009.
Miller, et al., Methods Used to Calculate Doses Resulting from Inhalation of Capstone Depleted Uranium Aerosols. Health Physics, vol. 96, No. 3, pp. 306-327, Health Physics Society, USA, Mar. 2009.
Seiler, et al., Continuous Monitoring for Airborne Alpha emitters in a Dusty Environment. Health Physics, vol. 54, No. 5, pp. 503-515, Health Physics Society, USA, May 1988.
McDiarmid, et al., The U.S. Department of Veterans' Affairs Depleted Uranium Exposed Cohort at 25 Years: Longitudinal Surveillance Results, Environmental Research 152, pp. 175-184, Elesvier, Inc., USA, Oct. 2016.
DOE 2004, Guide of Good Practices for Occupational Radiological Protection in Uranium Facilities, DOE-STD-1136-2004, p. 2-2, USDOE, Washington, DC, Dec. 2004.
Yu et al., Data Collection Handbook to Support Modeling Impacts of Radioactive Material in Soil, pp. 13-25, 93, 100-104, and 116-118, USDOE, Washington, DC, Apr. 1993.
Yu et al., Manual for Implementing Radioactive Material Guidelines Using RESRAD, Version 5.0, pp. 11-19, USDOE, Washington, DC, Sep. 1993.

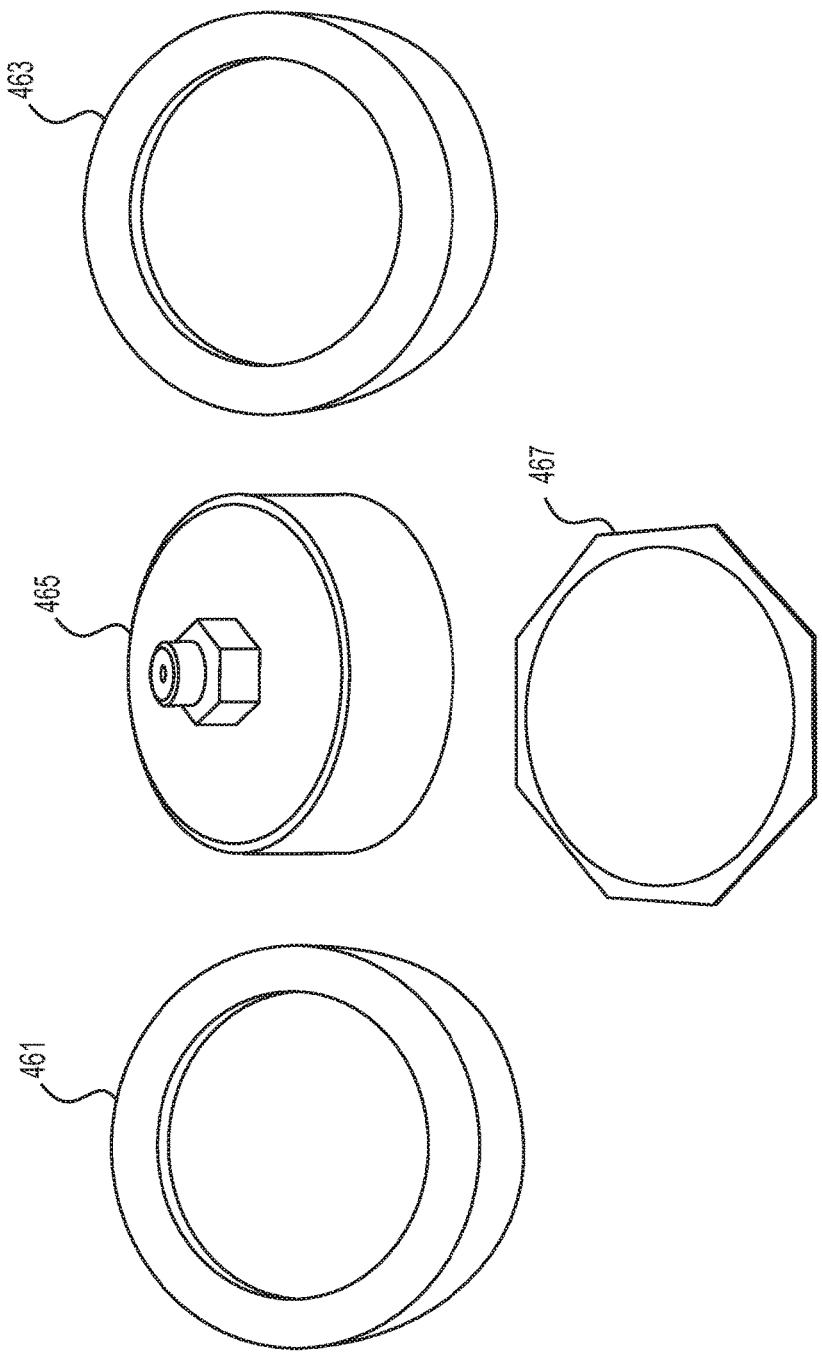

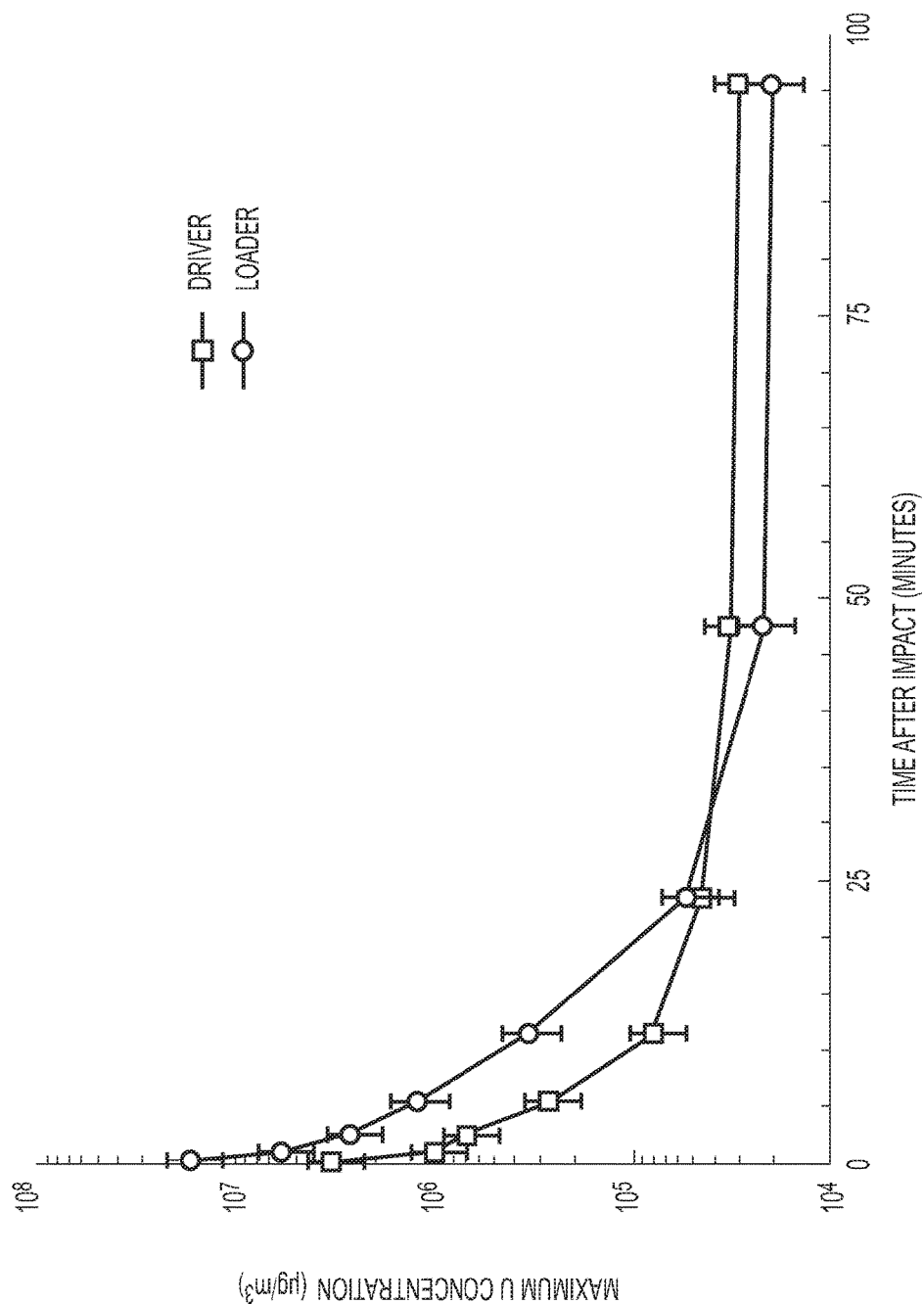

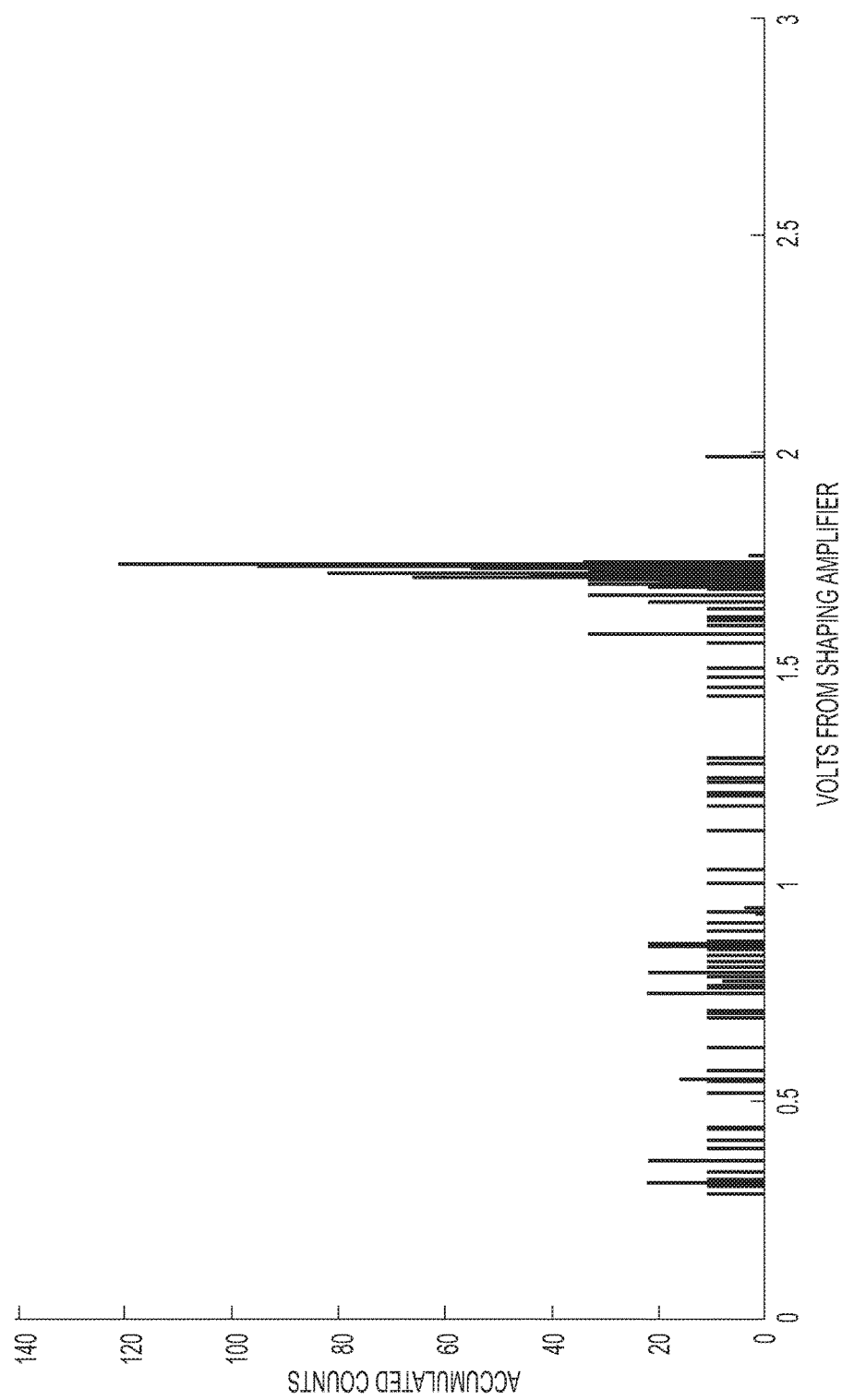

CONTINUOUS, REAL TIME MONITOR FOR AIRBORNE DEPLETED URANIUM PARTICLES IN THE RESPIRATORY RANGE AND CORRESPONDING METHOD OF USE

RELATED APPLICATIONS

This application claims priority to provisional patent application 62/361,603 filed Jul. 13, 2016, entitled "A CONTINUOUS, REAL TIME MONITOR FOR AIRBORNE DEPLETED URANIUM PARTICLES IN THE RESPIRATORY RANGE AND CORRESPONDING METHOD OF USE." The disclosure of this provisional application is incorporated by reference.

BACKGROUND

Certain radioactive materials emit particulate matter, namely alpha and beta particles that may be detected, identified, and quantified based on the measurement of the amount and energy of the alpha and beta particles emitted by the material containing the radioactive material. The emitted particulate matter may pose a hazard to humans through, for example, respiratory inhalation and/or ingestion. Various sampling systems are used to monitor for the presence of these particulate matter.

One specific alpha-emitting radioactive material is depleted uranium (DU). Depleted uranium has both military and civilian applications. Depleted uranium is uranium with a lower content of U-234 and the fissile isotope U-235 than is found in naturally-occurring uranium. Specifically, naturally-occurring uranium contains about 0.72 percent of the fissile isotope U-235, while the DU used by the U.S. Department of Defense contains 0.3% U-235 or less, as shown in Table 1.

TABLE 1

Summary of the Table of Isotopic Abundances of DU

| Isotope | Natural (mass Fraction) | Typical Commercial Feed Enrichment (mass fraction) | Depleted Uranium (mass Fraction) | Specific Activity (Ci/g) |
|---|---|---|---|---|
| U-238 | 99.20 | 97.01 | 99.80 | 3.3E−7 |
| U-235 | 0.72 | 2.96 | 0.20 | 2.1E−6 |
| U-234 | 0.0055 | 6.2E−3 | 0.0007 | 6.2E−3 |

From DOE-STD-1136-2004 (DOE 2004)

Natural uranium has a specific activity of 0.68 pCi/µg, while DU has a specific activity that is about 60% of this value (see first page of the Overview section of Rostker 2000) (citations to references are provide in footnotes and/or at the end of this disclosure). Also, as described in Section 3 of Rostker, DU could contain trace levels of neptunium, plutonium and americium if the original source of the DU is recycled uranium from reprocessing spent reactor fuel. However, these radionuclides are in such trace quantities as compared to U-238 they do not require explicit consideration in assessing the doses and risks associated with inhaled or ingested DU.

Depleted uranium is useful primarily because of its high density, on the order of 19.1 $g/cm^3$, as compared to the density of lead, 11.34 $g/cm^3$. Civilian DU applications include counterweights in aircraft, radiation shielding in medical radiation therapy and industrial radiography equipment, and containers for transporting radioactive materials. Military DU applications include armor plating and armor-piercing projectiles.

Most DU is a by-product of the production of enriched uranium for use as fuel in nuclear reactors and in the manufacture of nuclear weapons. Enrichment processes generate uranium with a higher-than-natural concentration of lower-mass-number uranium isotopes (in particular U-235, which is the uranium isotope supporting the thermal fission chain reaction) with the bulk of the feed ending up as DU, in some cases with activity fractions of U-235 and U-234 less than a third of those in natural uranium. Since U-238 has a much longer half-life than the lighter uranium isotopes, DU emits less alpha radiation than natural uranium (i.e., about 40% less). Depleted uranium also arises from nuclear reprocessing; DU from this source has isotopic ratios different from enrichment-byproduct DU, from which it can be distinguished by the presence of U-236

A large body of literature exists directed to DU issues; references from this body of literature cited herein are listed in detail at the end of this specification. The monograph, EPA 2006, provides an overview of the potential radiological and toxicological hazards associated with DU in the environment. Appendix 3 of the monograph provides a listing of the Superfund sites that are concerned, at least in part, with DU. Publications by the Wise Uranium Project, specifically "Current Issues—Depleted Uranium Weapons Tests and Incidents" (May 3, 2016) lists 21 sites where DU munitions have been or are being used in the U.S. The report also provides a summary of status reports of the issues associated with DU at individual sites and links to full text retrieval of the full reports (too numerous to describe here). In addition, a vast body of literature exists describing various physical and chemical forms of natural, depleted, and enriched uranium, and their associated radiological and toxicological hazards (see Cheng et al., 2009, ATSDR 2013, Parkhurst, et al., 2004, and Rostker, 2000). The literature describes the use of uranium and DU in a variety of commercial products, weapons systems, munitions, and as a byproduct associated with the development and production of the atomic bomb. Because of its widespread production and use, DU is ubiquitous throughout the world, and there is concern that it might represent both a radiological and toxic chemical hazard to individuals who might inhale or ingest DU under a number of conditions and settings, including:

1. Exposures to cleanup workers and members of the public during remediation of contaminated sites and facilities,
2. Exposures to members of the public exposed to DU in soil where legacy DU is present in soil,
3. Exposure of military and contractor personnel at facilities where munitions are tested, and
4. Exposure to military personnel during battle and also first-responders; i.e., those military personnel first on the scene (who were not in the vehicle) who help with vehicle and equipment evacuation, including battle damage assessment teams).[1]

[1] See Committee on Toxicologic and Radiologic Effects from Exposure to Depleted Uranium During and After Combat, Committee on Toxicology, Board on Environments Studies and technology, Division on Earth and Life Sciences. National Research Council, The National Academy Press, Washington D.C., www.nap.edu.

Many sites contaminated with natural uranium and DU are undergoing cleanup, where the soil and associated structures were contaminated with both natural uranium and DU. During cleanup, the natural uranium and DU may be resuspended and thus pose primarily an inhalation hazard to radiation workers and members of the general public. The literature provides some insight into the extent and concentration of DU in soil at selected sites. Hindin, et al, 2005 cited references that reveal that "In the United States there are over 50 sites that have been/are engaged in developing, producing, and testing DU munitions". Crean, et al. 2013 explains, "when a penetrator strikes an armored target, 10-35% (maximum about 70%) of the mass is converted into aerosol with median aerodynamic diameter of d<15 micron." This material disperses in the atmosphere and eventually deposits on nearby soil.

The following are examples of literature where the concentration of DU in soil at test sites have been reported:

Crean et al, 2013 describes the DU concentration in soil collected to a depth of 15 cm at Eskmeals in Cunbria, NW England, a Ministry of Defense (MOD) firing range that was used in the development and testing of DU weapons from the 1960s to 1995. The observed concentration of DU in surficial soil observed at different locations ranged from 37 to 320+/−40 mgU/kg (or about 10 to 100 to pCi/g).

Choy et al., 2005 reports concentrations of DU in surficial soil at U.S. Army sites of 3.99E3 Bq/Kg (1077 pCi/g), and that 83 percent of the DU is in fines (<0.075 mm or <75 microns) in which the DU concentration was 9.61E4 Bq/kg (2595 pCi/g) (note that natural background concentrations were reported as ranging from 1.7 to 2.2 mg/kg (i.e., 1.1 to 1.5 pCi/g) This concentration of naturally occurring uranium in soil is commonplace throughout the world. Table 25 of UNSCEAR 1993 summarizes the concentrations of naturally occurring Th-232 and U-238 in heavy mineral sands in Australia, reporting average concentrations in soil and rock for both Th-232 and U-238 of 40 Bq/kg or 1.08 pC/g).

The residual concentrations of DU in soil at battlefields have also been cited as follows:

Besic et al. 2017 reports soil concentration of DU in the Balkans at Hadzici and Han Pijsak in Bosnia and Herzegovina. The highest report activity of DU in soil at these battle ground sites range from 1024 Bq/kg (26 pCi/g) to 255,871 Bq/kg (6,909 pCi/g).

Mohammed 2008 presents a review of DU contamination in soil and its depletion and dispersion in the southern part of Iraq (Nassireya and Amara). In 2003, the DU concentrations in surface soil at 3 sites ranged from about 16 ppm (about 6.4 pCi/g) to 6 ppm (about 1.2 pCi/g). By 2007 the higher concentrations declined by about 25%, believed to be primarily by wind.

Sarap, et al 2014 reports the concentration of U-238 soil samples collected to a depth of 10-15 cm in southern Serbia at locations where DU penetrators were used and following cleanup of left over DU fragments by NATO. The observed U-238 concentrations in soil samples reported in Table 1 of the report ranged from 21 to 95 Bq/Kg (0.57 to 1.3 pCi/g of soil), which is consistent with values reported in the literature, also in Table 1 of the paper. These values are quite low and likely do not represent a radiological or toxicological hazard.

The assessment of the potential radiological and toxicological health risks at such sites, whether the sites are occupied or undergoing remediation, requires measuring the concentration of both natural uranium and DU in soil, air, and water. The health risks are primarily due to inhalation and ingestion of the different chemical and physical forms of uranium and DU. However, following an accident or during battle, relatively large fragments of DU can become imbedded in a person, and serve as a source of chronic DU dissolution into body fluids and the blood stream and deposition into organs of the body, such as the kidney and liver. Section 3 Part 5 of Rostker 2000 and also the latest update of Current Issues-Depleted Uranium Weapons Tests and Incidents (last updated May 3, 2017) present excellent overviews of issues and health effects associated exposure of military personnel to DU.

Parkhurst, et al., 2004 provides a comprehensive (627 page) report on aerosols of DU produced during testing of DU munitions used on Abrams tanks. A key finding of the report is that the airborne concentration inside armored vehicles following DU penetrator penetration ranged from 16 g/m$^3$ (16,000 mg/m$^3$) at 10 seconds after penetration to 0.029 g/m$^3$ (29 mg/m$^3$) one hour after penetration. An example of the time dependent airborne concentrations in the vehicle following penetration is provided in FIG. 5.5, in Parkhurst, et al., 2004 is in FIG. 18. The particle size distribution of the aerosols as a function of time following penetration ranged from a fraction of 1 AMAD (activity median aerodynamic diameter) at time 0-30 sec to about 100-micron AMAD after several hours following penetration.

The implications of FIG. 18 are that the concentrations of DU, both in terms of radioactivity and micrograms per cubic meter are both high and rapidly changing. This figure serves as a good example of the conditions that the CAM 10 might encounter and how the software controlling the air sampling and counting will continually and automatically self-adjust in order to ensure that reliable alpha counts, representative of the airborne concentration in real time, are obtained. The key to ensuring the accuracy and reliability of the continuous measurements of airborne DU under circumstances such as those described in FIG. 18 is to ensure that the amount of particulates (primarily DU) deposited on the filter does not exceed a level that could result in the self-attenuation of the alpha emissions from the DU deposited on the filter. Specifically, in other sections of this application, it is demonstrated that, as that thickness of the particulate material deposited on the filter approaches 1E-3 cm, the potential exists for alpha self-attenuation. Assuming the airborne concentration of DU is at the high end of the distribution in FIG. 18 (i.e., 1E6 micrograms per m$^3$) and the air flow rate is 10 L/min, the amount of DU deposited on the filter in one minute would be 10,000 micrograms (1E6 micrograms/m$^3$× 10 L/min×1E-3 m$^3$/L). Since the area of the filter is 450 mm$^2$, and assuming the density of the loosely deposited DU oxide on the filter, along with other airborne particulate material that may be present, is about 2 g/cm$^3$, the thickness of the particulates on the filter would be 1×10-3 cm; about the thickness that could fully attenuate the alpha emissions from the DU on the filter (1E4 micrograms/450 mm$^2$×100 mm$^2$/cm$^2$×0.5 cm$^3$/g×1E-6 g/microgram=0.0011 cm). Since the software controlling the air flow rate and duration of the airflow passing through the filter is continually being monitored, along with the airborne particulate concentration, the software will continually estimate the amount and thickness of the particulates on the filter. The software will continually adjust the flow rate and air sampling duration to ensure that the amount of particulates on the filter never reaches a point where the alpha emission from the DU on the filter will be substantively self-attenuated. Such a thickness will be empirically determined, but will initially be established at 1E-4 cm. When this thickness is reached, the filter will be moved from the sample collection location to the sample counting location, and a new filter will be moved to the sample collection location. These operational controls are referred to as a genetic algorithm.

During typical remediation efforts, both natural uranium and DU are monitored using methods that involve collecting samples and bringing the collected samples to a laboratory for analysis. A wide variety of techniques for the measurement of natural uranium and DU in solid and liquid samples have been developed and have been validated by many standard setting bodies. In addition, many laboratories are accredited for the performance of such analyses (DOE 2004 pg. 6-18)).

In addition to DU that is resuspended at legacy sites during occupancy or remediation, there is also a potential issue associated with outdoor testing of munitions and armor and the generation of airborne plumes of DU at the time of such testing. This topic was investigated in depth in the Capstone Depleted Uranium Aerosol Characterization and Risk Assessment Study (Holmes et al. 2009). The Capstone Study was initiated following the 1991 Gulf War (Operation Desert Storm). Although the investigations addressed DU aerosols inside armored vehicles, the data provide some insight into the anticipated characteristics of the aerosols of DU outdoors in the vicinity of these munitions tests. The data include airborne concentrations of DU particles, particle size distribution (an approximation of activity medium aerodynamic diameter—AMAD, which is the value of aerodynamic diameter for which 50 percent of the airborne activity in a given aerosol is associated with particles smaller than the AMAD, and 50 percent of the activity is associated with particles larger than the AMAD) and particle chemistry as a function of time inside the test vehicles. A review of the papers reveals that the airborne concentration of uranium inside the test vehicles within a few minutes after impact was between 1E4 to 1E5 µg/m$^3$ and remained at that level for at least two hours (Holmes, et al., 2009). The particle size distribution was found to be one micron AMAD at the end of two hours after the test (Cheng et al., 2009), and the aerosols quickly converted from the VI to the IV valence state; i.e., relatively soluble to highly insoluble (Krupka et al., 2009).

Because of concern regarding the exposure of workers during munitions testing and the possibility of fires associated with oxidation of uranium during testing (uranium metal is highly pyrophoric), such tests are now usually performed indoors and in other enclosures that minimize the potential for DU oxide aerosols to become airborne outdoors. However, it is often necessary for personnel to enter such enclosures shortly after testing in order to evaluate the performance of the munitions. Workers must wait until the airborne concentrations of DU aerosols decline before entry, and it is desirable to monitor DU prior to, during, and following entry into these enclosures. Such workers also often wear respiratory protection (which impedes worker efficiency to a degree). In addition, breathing zone samples and bioassay measurements are often made after the fact to ensure that worker exposures are maintained below radiation protection standards and as low as is reasonable achievable.

Depleted uranium munitions are also tested in a manner where they are fired but not detonated for the purpose of testing range and trajectory. In dry environments, such as in western regions of the U.S., DU penetrators oxidize on the firing range and can become aerosolized; again, posing a potential radiological and toxicological inhalation hazard.

SUMMARY

A continuous, real time monitor for airborne depleted uranium (DU) in the respiratory range includes mechanisms that enable continuous real-time determination or estimation of the airborne concentration of respirable DU (e.g., pCi/m$^3$ of U-238), real time dust loading on a sample filter (e.g., mg/cm$^2$), real time airborne concentration of respirable airborne particulates (e.g., mg/m$^3$) and size distribution of airborne particles, including particles of DU or aerosols with DU attached, in air being sampled; as a result, the monitor enables real-time determination of not only the airborne concentration of respirable particles of DU (e.g., pCi/m$^3$) but can also be set to alarm at a set point which immediately provides notification when the airborne concentration of particulates (e.g., mg/m$^3$) and U-238 concentration (e.g., pCi/m$^3$) approaches or exceeds a designated concentration as required to protect radiation workers and members of the general public from the potential harmful effects of airborne DU. The alarm set points can be prescribed by the user or set automatically based on the airborne, real-time measurement of the concentration of DU particles and the particle size distribution of the DU, both of which can vary based on changing on-site conditions.

A continuous, real time monitor for airborne depleted uranium (DU) in the respiratory range includes an air mover that pulls an air sample into the monitor, a continuous airborne particulate mass concentration device that enables a dust loading determination, a particle size detector device that provides a size distribution of particulates contained in the air sample, a movable filter mechanism through which the air sample is pulled and upon which particulates in the air sample are deposited, a solid state detector that measures alpha activity emitted from DU attached to particulates, and a processor that controls movement of the movable filter mechanism to place the movable filter mechanism in a first position in which the air sample passes thereby depositing the particulates and a second position at which the emitted alpha activity is detected and measured by the solid state detector, wherein the processor executes machine instructions to maintain the movable filter mechanism in the first position for a first time period, maintain the moveable filter mechanism in the second position for a second time period such that short-lived radionuclides decay, and maintain the moveable filter mechanism in the second position with the solid state detector activated to count the alpha activity from decay of the DU.

A continuous alpha monitor includes an air intake mechanism, which in turn includes an air mover and an air flowrate monitor, an air intake prefilter that limits particulates in the air intake mechanism to an aerodynamic diameter of 10 microns or less, and a particle size detector mounted downstream of the air intake prefilter, the air particle size detector providing a distribution of aerodynamic diameters of particulates in air passing the prefilter, the particulates including depleted uranium particulates. The monitor further includes a sample filter mechanism that collects the particulates; a detector mechanism that detects alpha radiation emitted by the collected particulates; a dust loading mechanism that computes a dust thickness on the sample filter mechanism; and an output mechanism that provides an indication of alpha concentration detected by the detector mechanism.

A continuous, real time monitor for airborne depleted uranium (DU) particles in a respiratory range, includes an air mover that pulls an air sample into the monitor at a desired airflow rate to deposit particles in the air sample on a filter media; a prefilter sized to pass only respirable range particles in the air sample, wherein the respirable range comprises particles having a maximum aerodynamic diameter of 10 microns or less; a first particle size detector that provides a first size distribution of the particles contained in the air sample; a movable filter mechanism through which the air sample is pulled, the mechanism supporting a plurality of the filter media upon which the particles in the air sample are deposited; a solid state detector that measures alpha activity emitted from DU particles in the air sample and deposited on the filter media; and a processor that executes a program of machine instructions, the program contained on a non-transient computer-readable storage medium, to: control movement of the movable filter mechanism to place the movable filter mechanism in a first position in which the air sample passes thereby depositing the particles and a second position at which the emitted alpha activity is detected and measured by the solid state detector, and compute, using the first size distribution, a dust loading on the filter media.

DESCRIPTION OF THE DRAWINGS

The detailed description refers to the following Figures, in which like numerals refer to like items, and in which:

FIGS. 8-12 illustrate components of a bread board model used to conduct example experiments related to DU sampling and counting operations that may be performed using the monitor of FIG. 1; and FIGS. 13-19 illustrate example experiment results and information related to the example experiments.

DETAILED DESCRIPTION

Figure 1:
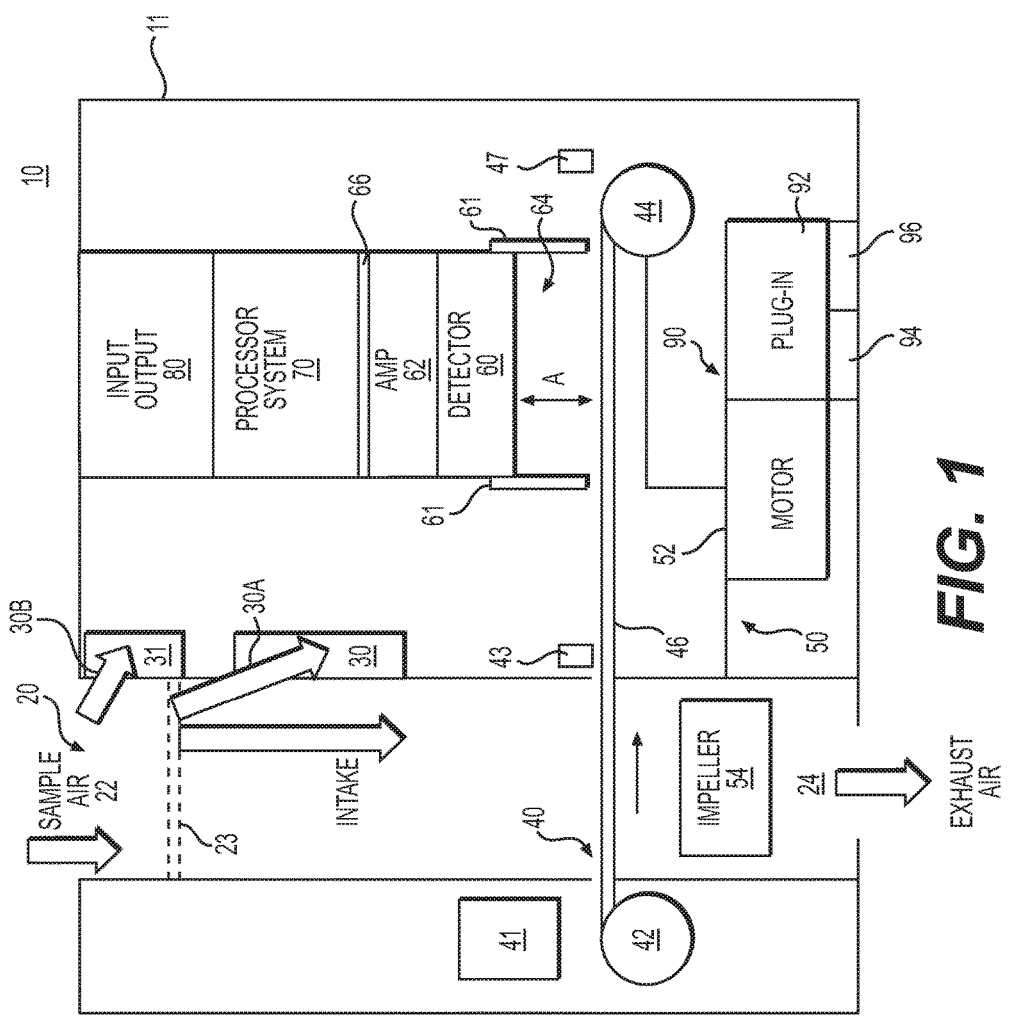
FIGS. 1-3 illustrate an example continuous, real time monitor for airborne depleted uranium in the respiratory range, and components thereof.

Except for the very specialized investigations performed as part of the Capstone Study, a review of the vast body of reports and analytical methods reveals that both natural uranium and DU in air, water, and soil usually are analyzed in a batch mode; i.e., samples are collected and then analyzed in a laboratory, and the results are reported at a later time, sometimes days later. Currently, no device or methodology exists for specifically monitoring airborne, respirable concentrations of DU at sites undergoing remediation or at munitions and armor testing sites using a real time, continuous monitor. The ability to monitor DU in such a manner is desirable so that action can be taken quickly when the airborne concentrations exceed acceptable levels for both workers who are involved in the indoor and outdoor munitions and armor testing and those workers involved in remediation of sites, as well as nearby members of the general public. Such a monitor can also serve a useful purpose during and following a military engagement where DU penetrators are employed. To address limitations associated with the use of periodic gab samples and subsequent analysis of these samples, disclosed herein is a device and a corresponding method of use to monitor the airborne concentrations of respirable DU particles in a continuous and real-time manner, with the objective of helping to ensure that no radiation workers, soldiers, military contractors, or members of the general public experience exposures to DU that exceed acceptable levels and are maintained as low as reasonably achievable. The device is, in addition, autonomous and operates in a generally unattended mode in the sense that particulates in the air sample are collected and the activity is measured and reported without the need for direct human operation of the device (such as removing sample filters).

Despite the very long history associated with the handling of both natural uranium and DU in its various forms, no real time, continuous air monitor has been developed for DU in the respiratory range. There are several reasons for this. First, although real time airborne monitors for alpha particulates are commercially available, they are designed for use in facilities and situations where very high levels of radioactive material are being stored, manufactured, or handled and must be contained. These situations and facilities are relatively dust-free (compared to outdoor DU environments), which, as is discussed herein, is an important design consideration for DU monitoring. In these facilities and situations, should containment fail, it is essential that workers be immediately informed so that protective and corrective actions can be implemented. Thus, currently air monitors operate with specific constraints that are not suitable at many DU facilities but may be acceptable in facilities that could experience such high levels of radioactive material. Depleted uranium is a type of radioactive material that generally does not pose a radiological acute risk (exposure to relatively high concentrations for short periods of time) during remediation. Instead, DU is of concern primarily as an outdoor contaminant and represents a potentially chronic, relatively low level of exposure of workers and the public. However, DU can represent an acute radiological and toxicological risk during munitions testing when workers need to enter the indoor testing enclosures shortly following testing and under battlefield and post action recovery operations.

In some scenarios, air particulate samples that are periodically analyzed in a laboratory (possibly in conjunction with periodic urine sample analyses for workers) may be adequate to ensure the health and safety of remediation workers and members of the general public associated with DU in the environment. However, laboratory analysis of site and urine samples may not provide the level of protection required or desired during cleanup of sites contaminated with DU, or during munitions testing involving DU. For example, members of the general public do not normally submit to urine samples and site samples may not be completed in real time. Thus, collecting periodic grab samples of airborne DU particulates during a remediation or munitions testing project and then analyzing the samples in a laboratory has been considered adequate for the protection of radiation workers and members of the general public. In contrast to these delayed sampling processes currently in use at DU sites, the use of continuous real-time monitoring of respirable particles of DU as disclosed herein may allow responsible parties to almost immediately be informed when unusually high levels of airborne DU occur, as opposed to waiting for the results of the periodic analysis of site and urine samples to determine that off-normal situations have occurred. In addition, at locations where munitions are tested indoors, continuous real-time monitoring will be helpful in identifying when workers can enter the testing enclosures.

Second, and perhaps more importantly, are the technical challenges associated with monitoring airborne respirable concentrations of uranium and DU in a continuous, real time manner in the environments in which DU may be encountered, such as at sites undergoing DU remediation and DU munitions and armor testing facilities. The challenges arise because the normal procedure to collect uranium aerosols is to continuously draw an air sample and deposit the dust and other aerosols contained within the air sample onto a filter. Because the filter collects all airborne particulates, including airborne DU, the result is the accumulation of a layer of dust in which the DU is deposited. This sampling process creates a problem because the way in which DU is detected and measured is by counting alpha particles emitted during the decay of uranium collected on the filter. However, alpha particles are easily attenuated by the smallest amount of dust present on the filter, making it difficult to accurately determine the quantity of DU present on the filter. In addition, there are many naturally occurring airborne radionuclides that also emit alpha particles, not unlike the alpha particles emitted by DU. Such radionuclides include the progeny of radon gas, which are ubiquitous in both the indoor and outdoor environments. The specific radon progeny that collect on filters and emit alpha particles include primarily Po-218 (3.05-minute half-life) and Po-214 (164 microseconds (μs) half-life and daughter of the beta emitter, Bi-214, which has a 20-minute half-life and is also deposited on the filter). As a result, even if the dust layer deposited on a filter is thin relative to the range of alpha particles, the presence of Po-218 and Po-214 can result in false positives in a real-time monitoring setting. These false positives can be managed with grab samples because counting a grab sample can be delayed until these short-lived progeny decay away. The challenges associated with the real-time, continuous monitoring of any airborne alpha emitter are described in detail in Seiler et al., 1988.

As a result of these challenges, the standard method for measuring the concentration of uranium in air, including the concentration of DU, is to draw a sample of air through a filter for some period of time, and then take the sample to a laboratory, weigh the sample, dissolve the sample, chemically separate the uranium from the rest of the solids that are on the filter, deposit the uranium atoms onto a planchette (leaving behind the other dissolved and undissolved solids that were on the filter), and then determine the number of uranium atoms on the planchette by counting the number of alpha particles emitted by the uranium atoms. This process removes any solids that could attenuate the alpha particles emitted by the uranium atoms and also excludes other non-uranium alpha emitters that might have been deposited on the filter during air sampling, such as Po-218 and Po-214. Alternatively, if the dust loading on the filter paper is very thin, and the only manmade radionuclide of interest is U-238 or natural uranium, it is possible to obtain a reliable estimate of the amount of uranium on the filter by waiting for the short-lived naturally occurring, alpha-emitting radon progeny to decay and then obtain a gross alpha count of the alphas in the uranium region of interest. Thus, this standard DU sampling method is far from continuous, real-time sampling.

As noted herein, assessment of the radiological risks associated with the use of DU or clean-up of sites potentially containing DU have generally been based on a grab sample (including general air samples and breathing zone or lapel samples), followed by laboratory analysis; this process is intended to remove the effects of certain radionuclides to achieve an accurate assessment for radionuclides of interest, and the delay in producing results is considered acceptable. To provide results in a timelier manner, some form of detector that counts activity from the sample in a continuous manner and produces a real-time readout may be desired. As noted herein, continuous air monitors exist that sample air for particulate matter and provide the results of radioactivity associated with the particular matter. However, these continuous air monitors have limited applicability, and certainly will not provide the desired results in an outdoor environment, such as exists at DU contaminated sites undergoing remediation, and/or DU projectile and armor test sites, and recovery activities following a military engagement where DU projectiles were employed. As an example, U.S. Patent Application 2003/0015655 to Ryden (hereafter Ryden) discloses an air monitor for alpha and beta emitters. A Canberra iCAM™ Alpha/Beta Air Monitor (referred to hereafter as iCAM™) (description available at www.canberra.com) appears to be a commercial embodiment of the Ryden air monitor. The Ryden air monitor and the iCAM™ are designed for a specific environment in which naturally occurring alpha emitters might interfere with reading alpha activity from radionuclides of interest, such as Pu-238 and Pu-239. As such, both the Ryden and iCAM™ monitors employ an auto adaptive radon and thoron compensation scheme for both alpha and beta based on alpha spectrometry. However, neither monitor includes the features and elements needed to function satisfactorily at, for example, a DU testing site undergoing remediation, munitions or armor testing, or long-term monitoring of a DU testing site. Specific differences between the herein disclosed continuous, real time monitor for airborne depleted uranium particles in the respiratory range and the iCAM™ are discussed in detail later.

To overcome limitations inherent in current alpha detection devices, systems, and methods, including the iCAM™, disclosed herein is a continuous, real-time monitor, and a corresponding method of use, for measuring respirable alpha particles emitted by depleted uranium. The monitor is autonomous and can operate unattended for an extended time. The monitor operates under atmospheric conditions within its counting chamber (with the possible exception of controlling temperature and humidity in the counting chamber), and thus does not require generation of a vacuum when counting alpha particles. The monitor includes mechanisms that enable real-time determination or estimation of dust loading on a sample filter and size distribution of airborne particles, including DU particles and particles with DU attached, in air being sampled; as a result, the monitor enables real-time determination of DU exposure for both radiation workers and members of the general public, with the DU exposure limit established based on the real time airborne particle size distribution, which can vary based on changing on-site conditions related to airborne particle size distribution and dust loading on the sample filter. The monitor is especially useful for monitoring during remediation of DU sites, such as outdoor firing ranges involving DU munitions and/or DU armor and immediately following munitions testing performed indoors. The monitor also is useful for monitoring during actual DU firing exercises.

FIG. 1 is a simplified diagram showing example components of an embodiment of the continuous, real time monitor (referred to hereafter as continuous air monitor (CAM) 10). The description of the CAM 10 that follows, including the descriptions referring to FIGS. 1-4B, uses the following terms and their associated meanings or definitions:

Aerosols are colloids or suspensions of fine solid airborne particles in the respirable range, having diameters ranging from less than 1 micron to about 10 microns. Larger sized particles can be present in the air, but are not respirable; i.e., they will be deposited in the upper respiratory tract and then removed by clearance up the respiratory tract mucociliary ladder and swallowed or eliminated in expectorate or blowing out of the nose. DU taken into the body by these mechanisms do not represent a radiological risk because they do not penetrate to the deep lung, but can represent a chemical toxicological risk to other organs, notably the kidney, if absorbed into the body. Such absorption can be important for the more soluble forms of DU (Rostker 2017)

Airborne DU concentration is the radioactivity of the airborne DU particles expressed in $pCi/m^3$.

Airborne particulate or aerosol mass concentration is the concentration of airborne material expressed in $mg/m^3$.

Dust consists of airborne particles, typically originating as soil, and which may settle onto a filter during air sampling operations. As used herein, dust refers to particles or particulate matter deposited on a sample filter during airborne monitoring.

Dust loading on a filter is the amount of dust on a sample on a filter expressed in $mg/cm^2$.

Mass concentration refers to the mass of materials, such as airborne particulates generally expressed in terms of $mg/m^3$.

Particulates refers to the fine solid airborne particles also referred to as aerosols.

Referring to FIG. 1, the CAM 10 includes intake/exhaust 20, particle size distribution/dust loading mechanism 30, movable air sampling mechanism 40, air mover 50, solid state detector 60, processor system 70, input/output module 80, and power supply and environment module 90. Finally, the components and mechanisms of the CAM 10 are contained in housing 11.

The intake 20 is shaped and designed to provide a straight flow of sample air through intake port 22 into the housing 11, through various components of the CAM 10, and on to the movable air sampling mechanism 40. After passing through the mechanism 40, the sample air exits the housing through exhaust port 24. The intake 20 also may include an optional adjustable intake filter 23 to filter out large diameter particulates. The filter 23 may operate in conjunction with a differential pressure monitor and alarm (not shown) to indicate filter clogging. The filter 23 may be removed (and if necessary, replaced) easily, either as a result of clogging or to change the size of particles the filter 23 are intended to pass into the intake 20. In an embodiment, the filter 23 is intended to pass particles with an aerodynamic diameter of 10 microns or less.

The particle size distribution and associated real time respirable airborne particulate concentration mechanism 30 provides the means to account, in real time, for particle size distribution in the air sample and airborne particulate concentrations when determining DU activity. Elements of the CAM 10 then may use the determined particle size distribution, as discussed herein, to compute, on a real-time basis, activity limits for both radiation workers and members of the general public. The computation of the dust loading on the filter is used by elements of the CAM 10 to determine if sample counts may be unduly affected because of shielding of alpha particles by dust collected on the sample filter (referred to hereafter as sample location 46A of web 46—see FIG. 2B).

In another embodiment, a second air particle size detector 31 may be installed upstream of prefilter 23 and may operate to provide a particle size distribution in terms of aerodynamic diameter (for particles with aerodynamic diameters greater than 10 microns (for example, up to or in excess of 50 microns). Such a detector 31 may have utility in situations when larger size particles may be of concern. As can be seen, when the second air particle size detector 31 is installed, a portion 30B of the air intake may be diverted through the detector 31.

To enable these computations, in one embodiment, the mechanism 30 receives the intake air sample and determines particle size distribution for aerosol particles contained in the air sample. In an aspect, the mechanism 30 provides data to express particle size in terms of diameter (microns) and/or median aerodynamic diameter, and/or activity median aerodynamic diameter (AMAD), also expressed in microns. The mechanism 30 provides the particle size distribution to the processor system 70 so that DU activity may be measured and an allowable set point for exposure to radiation workers and members of the general public may be computed, in real time.

In another embodiment, the mechanism 30 may be used to estimate the dust loading on the sample location 46A that will occur during air sampling. The dust loading may be expressed as $mg/cm^2$. In an aspect, two devices are used to measure airborne concentration of particles (microgram/$m^3$) and median aerodynamic diameter (microns) both upstream and downstream of a prefilter; a first device is upstream of the prefilter and a second device is downstream of the prefilter. In each device, sample air passes through a measurement chamber where the particles are illuminated by a light source and the resulting scattered light is detected under a certain detection angle. The resulting signal of the scattered light is output as airborne dust concentration ($mg/m^3$), or dust loading. In an embodiment, a portion of the air sample entering the intake 20, indicated by arrow 30A, is diverted from the intake 20 for measurement. The operation of the mechanism 30 is discussed in more detail below.

As an alternative embodiment, rather than placing the particle size distribution/dust loading mechanism 30 in the intake 20, the functions of the mechanism 30 may be incorporated into a standalone device; that is, for example, the dust loading measurement may involve a sample chamber that is separate from the intake 20. In an aspect, the dust loading measurement device (and the particle size measurement device) may be separate from the CAM 10. In yet another alternative embodiment, particle size distribution and/or dust loading may be estimated based on data from the site being remediated and using algorithms disclosed herein.

The movable air sampling mechanism 40 may be structured as a continuous conveyor belt or, as illustrated in FIG. 1, a mechanism having dispenser roller 42 and uptake roller 44 over which replaceable web 46 is set to move past the intake 20 to collect an air sample and then move to the solid-state detector 60 to read alpha activity from the collected sample. The roller 44 may be operated by motor 52 with the roller 42 rotating (idling) in response to the rotation of the roller 44. The motor 52 operates in response to signals from the processor system 70. Use of replaceable web 46 (instead of a continuous web or belt) may be preferable so that any particles remaining on the web after a prior sampling operation will not affect future sampling operations. That is, in an embodiment, the web 46 does not form a continuous loop around the rollers 42 and 44. In addition, rollers 42 and 44, and other elements of the mechanism may be contained in a replaceable cartridge assembly (not shown) that allows easy replacement of the web 46 and also serves to contain radioactive material deposited on the web 46. Finally, a filter media lifting device, described with respect to FIG. 3, may be included.

The web 46 may be formed from Teflon®, glass fiber, paper, or other media material. Preferably, the web 46 is formed from a material that will not repel the aerosol particles, nor allow the aerosol particles to become embedded in or absorbed by the web 46. The web 46 may be changed when the amount of web material on the roller 42 reaches a near endpoint. The mechanism 40 may include a detector 41 that determines the near endpoint of the unrolling web 46 and provides a corresponding signal to the processor system 70. The detector 41 may perform this function by simply counting rotations of the roller 42 or the roller 44, or the number of samples counted, for example.

In an aspect, the mechanism 40 may include optional advanced, passive static eliminator 43, which may consist of a rod or wire placed perpendicular to the movement direction of the web 46. Such static eliminators are available from Stopstatic.com.

Figure 2A:
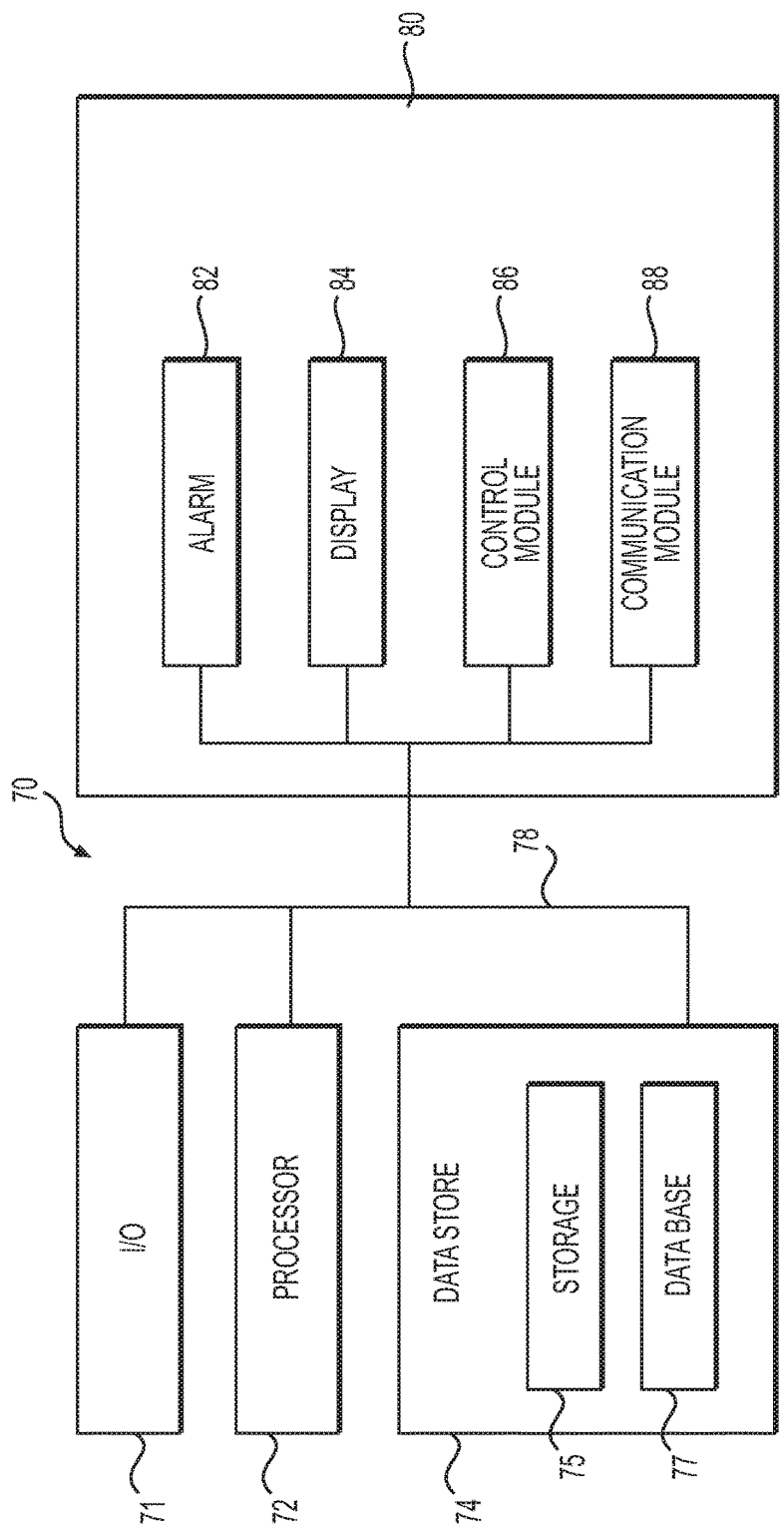
Figure 4A:
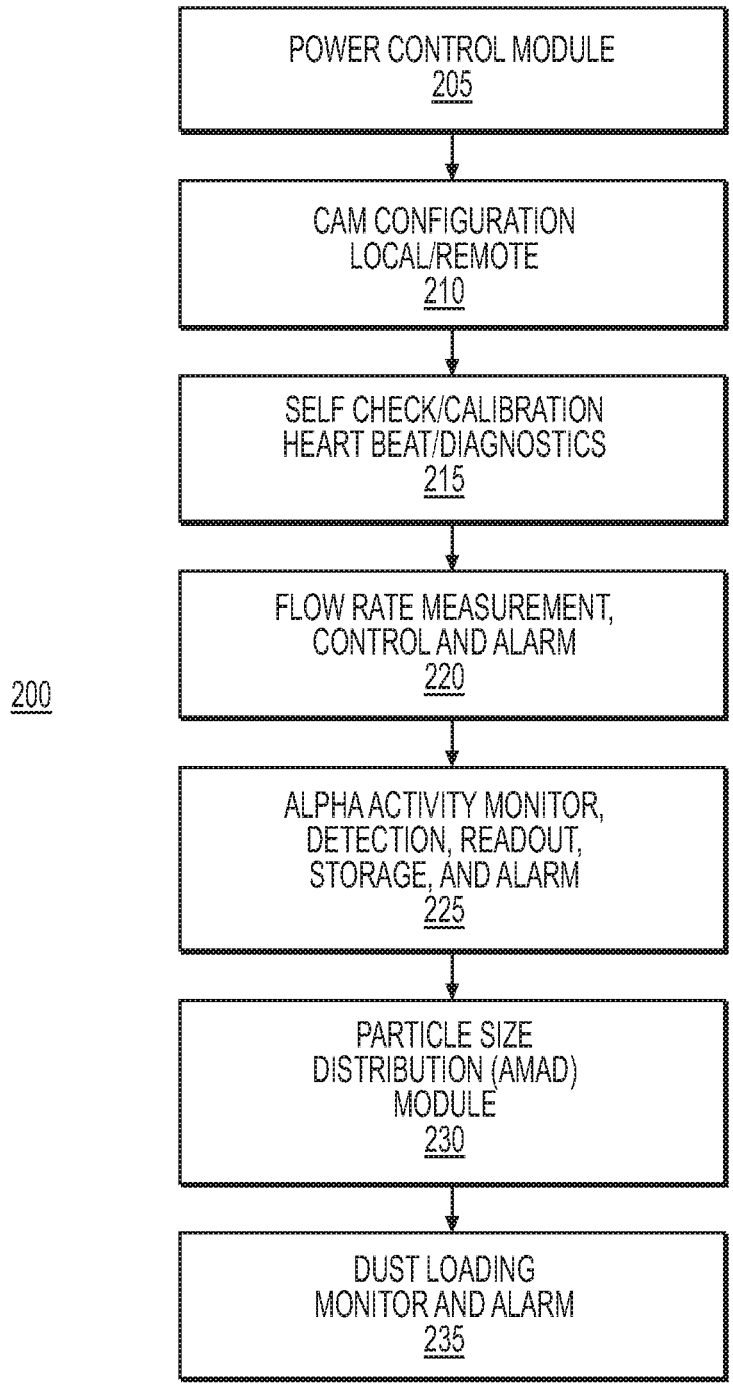
FIGS. 4A-B illustrate an example program executable by components of the monitor of FIG. 1.
Figure 4B:
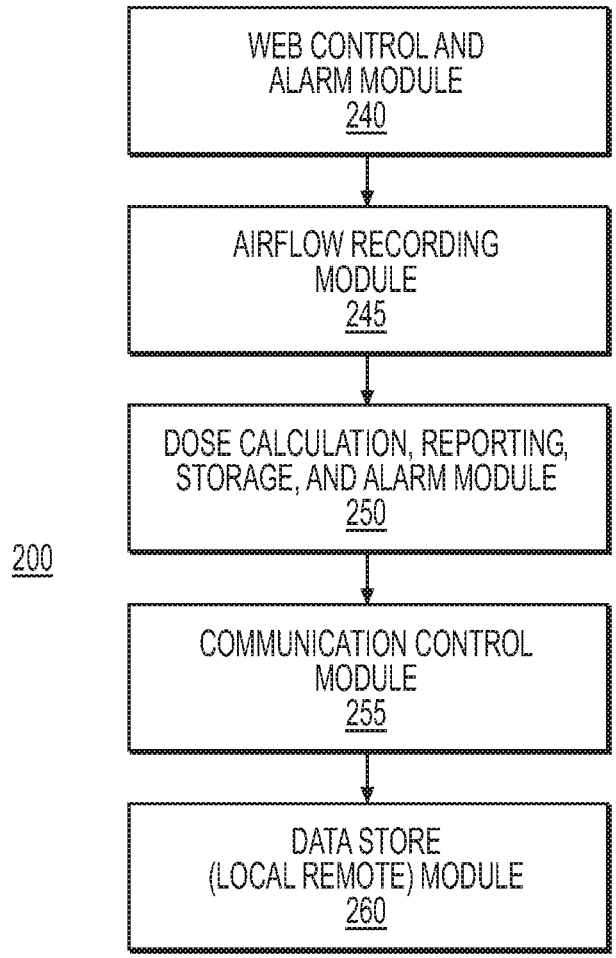

Further aspects of the mechanism 40 are described with respect to FIGS. 2A and 4B, The air mover 50 includes a multi or variable-speed electric motor 52 driving an impeller mechanism 54 that pulls air through the intake 20, past the particle size mechanism 30 and through the movable air sampling system 40, and exhausts through exhaust port 24. The size of the air mover 50 is chosen to achieve the desired air flow rate to achieve the desired sampling efficiency and accuracy, and may be 10 liters per minute (L/min), for example. The air flow rate of 10 L/min may be employed when the CAM 10 operates in a battery mode, and the air flow rate may be changed based on a variety of factors including the source of power to the motor 52.

The solid-state detector 60 is a silicon dioxide ($SiO_2$) detector or similar detector. Such detectors are well known and are efficient in alpha spectroscopy. The detector is coupled to an amplifier circuit 62 to ensure an adequate signal is available for supply to the processor system 70. In an embodiment, the detector 60 may be encased in movable detector housing 61, which forms a light-tight barrier when the CAM 10 is actually counting alphas.

The detector 60 may be placed within the CAM 10 such that surface 64 of the detector 60 is spaced A millimeters (mm) above the surface of the web 46. The spacing A is preferably about 3 mm or less, and may be as small as about 1 mm. In an embodiment, the detector 60 is attached to adjustment mechanism 66 that may be used to adjust the height of the detector surface 64 above the web 46.

The processor system 70, in an embodiment, includes a programmable processor and various data and program storage elements. The processor system 70 is described in more detail with reference to FIG. 2A.

The input/output module 80 receives signals from the processor system 70 and provides various outputs, including an alarm indicating a protective set point has been reached, and end of filter signal indicating the web 46 should be replaced, a readout of particle size, dust loading on the web 46 (e.g., $mg/cm^2$-milligrams per square centimeter), and alpha activity, and other data. The module 80 may provide outputs locally on the CAM 10 and may send outputs to a remote station, either by wired or wireless communications. The module 80 also may allow an operator to change settings such as air flow rate and other parameters to affect operation of the CAM 10

The power supply and environment module 90 performs two functions. First, the module 90 provides electrical power to the various mechanisms, modules, and components of the CAM 10. The module 90 may include a plug-in power supply 92, a rechargeable battery 94 and an alternate power supply 96. The module 90 may include an AC/DC converter, a DC/AC converter, power regulators, and other components (not shown in FIG. 1) normally found in a regulated power supply. The alternate power supply 96 may be or may include a solar power system, for example. The module 90 allows the CAM 10 to be used in remote locations, away from any grid-based power source. The battery 94 is sized to permit protracted operation of the CAM 10.

An optional second function of the module 90 is to maintain satisfactory environmental conditions within the housing 11. For example, the module 90 may include a temperature control unit (which may include one or more ventilation fans, or a refrigerant-based cooling system, and a heating system, for example—not shown) to regulate temperature within the housing 11 and a humidity control unit (not shown) to regulate humidity.

FIG. 2A illustrates selected components of the CAM 10 of FIG. 1. The selected components are shown without specific reference to their location within the CAM 10. In FIG. 2A, processor system 70 is shown to include input/output (I/O) 71, processor 72, data store 74, and communications bus 78. The data store 74 includes non-transient computer-readable storage medium 75 on which is stored monitoring program 200, described in detail with respect to FIGS. 4A and 4B, and data base 77, which stores data used by and/or generated by the processor 72. The communications bus 78 connects the processor 72 to data store 74 and to other components of the CAM 10, including the I/O module 80 (as shown in FIG. 2A) such that the processor 72 may receive signals from and provide signals to those components, as appropriate.

In the embodiment of FIG. 2A, processor 72 is shown installed within the CAM 10 and can be seen to direct the operations of the CAM 10 by execution of program 200 and by possible reception of command signals from another remote computer or processor. In another embodiment, most or all of the functions of the CAM 10 may be directed from a remote processor (e.g., at station 130—see FIG. 5—or in a cloud computing environment) with the processor 72 receiving commands from the remote processor and sending data and reports to the remote processor.

The I/O module 80 includes alarm module 82, display module 84, control module 86, and communication module 88. The alarm module 82 provides for physical manifestations of alarms, such as visual alarms (lights), audible alarms, and alarm readouts at the CAM 10. The display module 84 includes physical display, at the CAM 10, of various readouts, in text and image format on a human-readable display or graphical user interface. The control module 86 provides human user interface and local control of the CAM 10 through various switches, buttons, and soft keys, for example. The communication module 88 provides wired and wireless communications from the CAM 10 to one or more remote locations. Using the communication module 88, the CAM 10 may send data, alarms, status, and other information to connected machines using any current network, including wide area networks such as the Internet, and local area networks. The communication module 88 allows for cloud storage of information from the CAM 10.

Figure 2B:
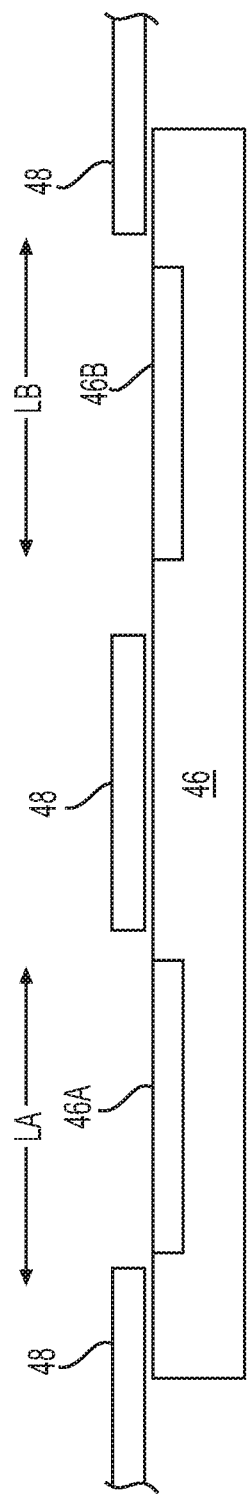

FIG. 2B illustrates a segment of the web 46. In FIG. 2B, the web 46 is shown with sample location 46A. Sample location 46A corresponds to a position in the intake 20, and is where samples impinge, and pass through, web 46, depositing particulate matter on the web surface. Counting location 46B corresponds to a position below the detector 60. Thus, web 46 is seen to advance sample location 46A where a sample is collected to counting location 46B, where (1) the collected sample may sit without counting to allow decay of short-lived radionuclides, and (2), after the wait, the detector 60 is activated to count alpha activity from DU (and other alpha emitters) in the sample. Movement of the web 46 is under control of the processor 72 executing program 200 (described with respect to FIGS. 4A and 4B) to allow a sufficient collection time at sample location 46A, sufficient decay time at counting location 46B, and sufficient counting time at counting location 46B.

In an embodiment, the mechanism 40, and in particular the web 46, may be supplied as a replaceable cartridge and, may be encased, in part, in housing 48, a portion of which is shown in FIG. 2B. In addition to making web replacement easy, the housing 48 provides some containment of radioactive materials remaining on the web 46 after sampling and counting. To allow for sample collection and subsequent counting, the housing 48 is open over the lengths LA and LB while allowing the detector housing 61 to maintain a light-tight seal with the housing 48.

Figure 3:
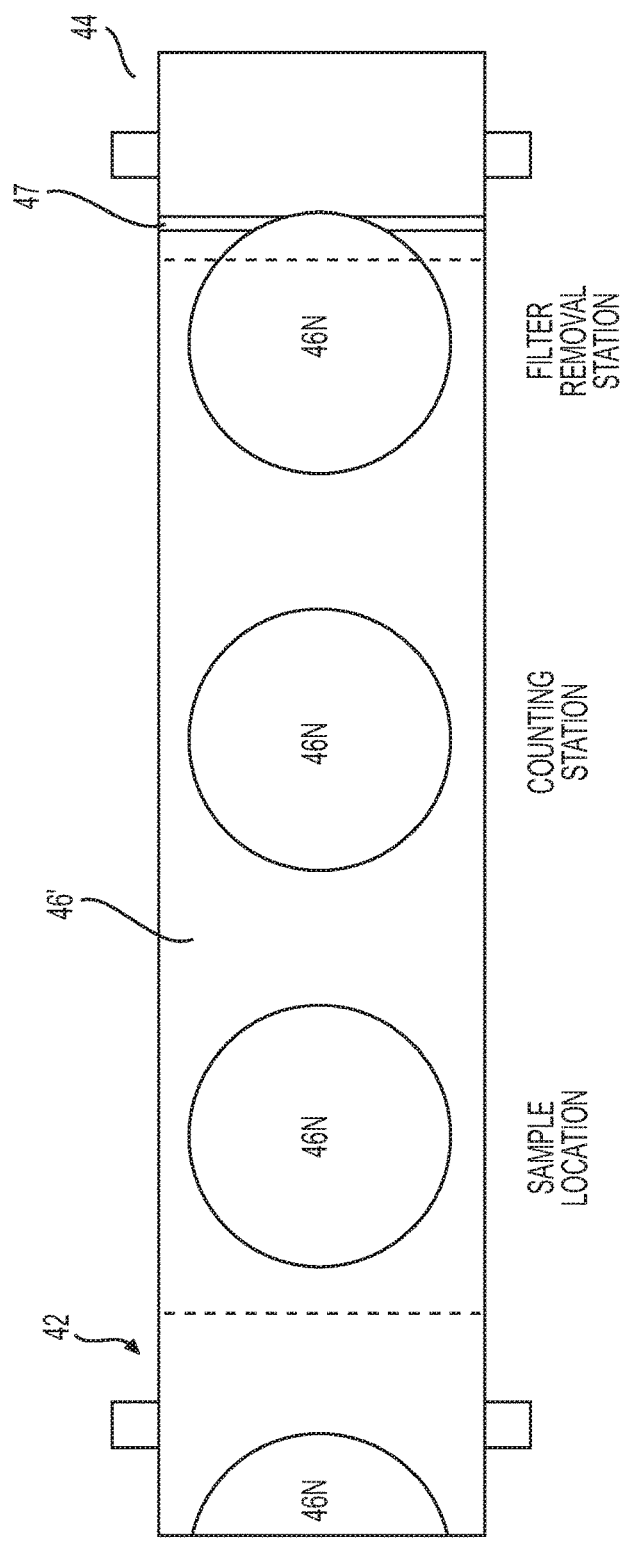

FIG. 3 illustrates an embodiment of a movable web, held within housing 48 (not shown in FIG. 3), that may be used with the CAM 10. In FIG. 3, web 46' is shown in a top-down view suspended around rollers 42 and 44 (shown partially by the dashed lines). The web 46' may be made of any suitable material but is porous to allow passage of air. The web 46' has mounted thereon, a number of circular elements 46N. FIG. 3 shows three such elements 46N, one in a sample location, one in counting station, and one in filter removal station. The circular elements 46N are adhered to the underlying web 46' using a flexible, non-permanent adhesive such that the elements 46N may be removed from the web 46' by a human user or automatically by a suitable lifting device, such as device 47, which lifts a leading edge of the element 46N when the element 46N arrives at the filter removal station without displacing or disturbing any material collected on the element 46N during airborne sampling operations of the CAM 10. In an aspect, the lifting device may be built in to the housing 48 and the housing 48 may be constructed with a slot or opening that allows the lifted element 46N to be removed from the housing 48 and collected for subsequent laboratory analysis. In an alternative configuration, the housing 48 may be constructed with an opening that allows manual removal of elements 46N (by a human user).

The elements 46N, as well as the web 46', may be formed from Teflon®, glass fiber, paper, or other material. Preferably, the elements 46N are formed from a material that will not attract or repel the aerosol particles, nor allow the aerosol particles to become embedded in or absorbed by the elements 46N. The adhesive (not shown) that holds the elements 46N to the web 46' may be any suitable material that maintains the elements 46N securely adhered to the web 46' during storage and operation, including sampling and counting, yet allows air flow and easy removal of the elements 46N from the web 46' without disturbing the collected material deposited on the element 46N.

Figure 5:
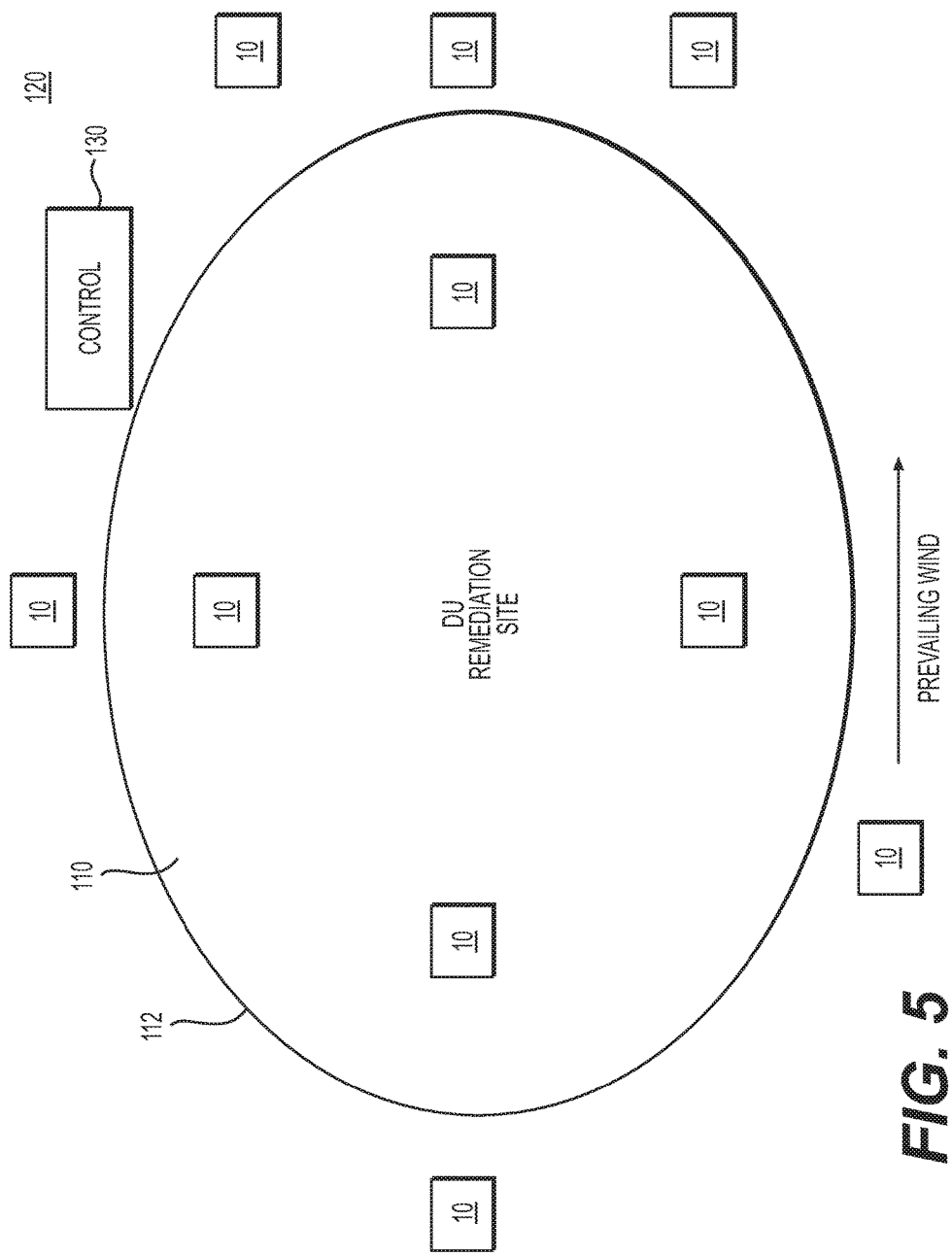
FIG. 5 illustrates an example system deployment of one or more of the monitor of FIG. 1.

FIG. 5 illustrates an environment in which one or more CAMs may be used. In FIG. 5, environment 100 includes a DU site 110 undergoing remediation. The DU site has a perimeter fence 112 to limit access. Members of the general public may reside or work outside the perimeter 112. Network 120 includes control station 130 and a number of CAMs 10 placed inside and outside the perimeter 112 and operating under control of the station 130. The distribution of CAMs 10 is purely for illustrative purposes. The CAMs 10 may communicate with the station 130 by wired or wireless means. One or more of the CAMs 10 also may be under local control. Some or all of the CAMs 10 may be in operation simultaneously. Some or all of the CAMs 10 may operate during actual remediation operations or may operate continuously until remediation is complete.

FIGS. 4A and 4B illustrate, in block diagram form, an example program of instruction executable by components of the CAM 10. In FIGS. 4A and 4B, program 200 includes power module 205, CAM configuration module 210, self-check/calibration/heart beat/diagnostics module 215, flow rate measurement, control, and alarm module 220, alpha activity monitor, detection, readout, storage, and alarm module 225, particle size distribution (AMAD) module 230, dust loading monitor and alarm module 235, web control and alarm module 240, airflow recording module 245, airborne DU activity concentration computation and reporting, storage, and alarm module 250, communication module 255, and data storage module 260.

The power module 205 controls power into the CAM 10 and distribution of power to various components of the CAM 10.

The CAM configuration module 210 receives commands from the processor 72 and provides signals to components of the CAM 10 to operate in a specific manner. For example, the module 210 may direct the variable speed motor 52 to operate at a speed that achieves a desired flow rate of sample air. The module 210 also may provide signals that indicate the configuration of the CAM 10, such as the sample air flow rate or motor speed.

The self-check/calibration/heart beat/diagnostics module 215 provides start-up checks and optionally provides a "heart beat" signal to the control station 130. The module 215 also enable calibration checks and diagnostics routines.

The air sampling flow rate measurement, control, and alarm module 220 measures air flow rate in the intake 20 and adjusts the speed of the motor 52 as needed to provide a desired/required airflow. The module 220 also provides a low flow and a high flow alarm, locally at the CAM 10, and remotely at the control station 130.

The alpha activity monitor, detection, readout, storage, and alarm module 225 controls operation of the detector 60 to detect and count alpha emissions and provides a real-time readout of counts, derived airborne DU activity concentration, and related data. The module 225 also provides for local and remote storage of the data. Finally, the module 225 provides alarm set points and activates alarms (audible, visual) when set points are reached.

The particle size distribution (AMAD) module 230 may use a default value for the AMAD of DU. Thus, in an embodiment, the CAM 10 may operate on the premise that the airborne particles of DU have an AMAD of 5 microns or other selected AMAD. A 5-micron or a 1-micron AMAD is recommended by the International Commission on Radiation Protection (ICRP) (depending on circumstances) because these diameters are representative of respirable airborne particles in general and also are associated with a relatively high radiological hazard potential as compared to particles with larger sizes. In another embodiment, the module 230 may incorporate an algorithm, such as the algorithm of Equation 1, that may be executed to adjust the alarm level if the AMAD of the actual particles deviates significantly from 1 or 5 microns AMAD. The module 230 may receive various measurements from the module 230 to estimate the AMAD. In an aspect, the module 230 includes instructions and routines to perform a real-time determination or estimation of particle size distribution of particles in air being sampled; the real-time determination provides an appropriate DU exposure limit for both radiation workers and members of the general public with the DU exposure limit varying based on changing on-site conditions related to airborne particle size distribution.

The dust loading and alarm module 235 directly measures the airborne concentration of aerosols entering the air sampling intake 20 (in terms of mg/m$^3$), in combination with the measured airflow rate (e.g., L/min) with appropriate unit conversions estimates the amount of dust accumulating at the sample location 46A (in terms of mg/cm$^2$ and/or in terms of thickness in mm, provides a readout for each sample collected, and provides an alarm if the airborne DU concentration or the amount of dust deposited in the filter exceeds the selected set points.

The web control and alarm module 240 controls movement of the web 46 between the sample position and the counting position (see FIG. 3). The module 240 also provides an end-of-web alarm when the web 46 requires replacement.

The airflow recording module 245 receives measurements of airflow from the mechanism 30 and provides a readout. The module 245 also provides alarm values should airflow reach a high or low alarm set point (L/min).

The airborne DU aerosol calculation, reporting, storage, and alarm module 250 provides a readout of DU concentration in pCi/m$^3$ with an associated time stamp. The module 250 also computes average concentration for radiation worker locations, site boundaries, and offsite locations on a daily, weekly, monthly, and annual basis. The module 250 may provide for storage of the data locally in the database 77 and may send the data, in the form of reports or in other formats, to a remote-control station. Finally, the module 250 may provide visual and audible alarms when computed DU concentrations reach a specified limit, such as 7 pCi/m$^3$ for radiation workers.

The communication module 255 controls signal and data reception and transmission components of the CAM 10 to send and receive data, commands, and alarms, as appropriate, between the CAM 10 and other devices and the control station 130.

The data storage module 260 provides for data storage onboard the CAM 10, optionally in a cloud, and formats data for transmission to other devices and the control station 130.

Having described components of the CAM 10, and an example environment in which the CAM 10 may operate, following is a conceptual design description of the CAM 10. The conceptual design takes into account the short-lived progeny of radon as well as the likelihood that the DU itself will contain relatively small amounts of alpha-emitting U-234 and U-235 and perhaps other alpha emitters associated with DU from recycled uranium. Some depleted uranium is produced from sources of uranium that were previously irradiated and recycled and may contain very small amounts of manmade alpha emitters and other radionuclides that are extremely small in concentration and will not interfere in the intended performance of this device.

Miller et al., 2009 reports that DU munitions are comprised of 12.3 Bq/mg of U-238, 1.39 Bq/mg of U-234, and 0.16 Bq/mg of U-234. Accordingly, about 10 percent of the alpha emissions from DU are from isotopes of uranium other than U-238. In an embodiment of the CAM 10, the alphas from U-234 (4.8 MeV) and U-235 (4.4 MeV) are included because these alphas also contribute to the radiation exposures of interest. In another embodiment, the CAM 10 counts the alpha emissions from U-238 (4.2 MeV) and multiplies this count by 1.1 to account for the contribution of alphas from U-234 to the dose. This embodiment takes advantage of the fact that both the inhalation and ingestion effective dose conversion factors for the three uranium isotopes (U-234, 235, and 238) are virtually identical. Thus, either embodiment of the CAM 10 may include the contribution of U-234 and U-235 to the radiation exposure associated with DU. Other aspects of these two embodiments; i.e., counting the alphas directly by extending the energy region of interest up to 4.8 MeV or multiplying the count in the U-238 region of interest i.e., 4.2 MeV and below, by 1.1, are discussed in more detail below.

Naturally occurring Th-232 and U-235 series radionuclides also are present in soil and airborne particulates, but in concentrations that are negligible compared to the concentration of U-238 associated with DU. Specifically, the concentration of U-238 in DU in soil at many sites contaminated with DU are on the order of hundreds to thousands of pCi/g (see Choy et al., 2006 and the other references cited above), while the concentrations of naturally occurring uranium and thorium in soil are about one to two pCi/g each (see Table 4.3 of NCRP 1987). In an aspect of the two embodiments mentioned above, the CAM 10 is designed specifically to quantify the concentration of U-238 (and perhaps also the small amounts of U-234 and U-235 associated with the U-238) in airborne DU at a site while discounting the presence of other alpha emitting radionuclides except for Po-218 and Po-214. Should a DU site include other man-made alpha emitting radionuclides (i.e., transuranic elements), those alpha emitters likely will not be present in concentrations of concern; however, the CAM 10 may not be suitable at sites where other man-made alpha emitters are a major concern (i.e., at airborne concentration comparable to that of U-238).

For typical DU sites undergoing remediation, the output of the CAM 10 will include an accurate determination or estimate of the activity concentration (pCi/m$^3$) of DU at levels of interest for the protection of radiation workers (i.e., workers operating under an NRC, NRC Agreement State, or DOE License), military personnel, and members of the general public without the risk of false positives or false negatives, as long as the CAM 10 can exclude counts associated with Po-218 and Po-214 (i.e., in theory, Po-218 and Po-214 may cause false positives), and avoid attenuation of the alpha emissions from U-238 (which, if it occurs, may result in false negatives). These two aspects are addressed in detail in the description of the conceptual design of the CAM 10 provided below.

How the CAM 10 works and why the CAM 10 differs from and is an improvement on other monitors and methods currently used to monitor alpha emitters, as applied to continuously monitoring DU, is shown with a hypothetical example. The example begins with the assumption of a site where soil or the floors, walls, and equipment within a building are contaminated with DU, and the site and its facilities are undergoing remediation or workers need to enter an enclosure where munitions are tested. During remediation, the contaminated soil, structures, and/or equipment will generate aerosols that contain DU. It would be desirable to know the activity concentration of DU in real time and when the airborne activity concentrations of respirable particles exceed a level that could result in radiation exposures to radiation workers and also members of the public that exceed the applicable radiation protection standards for each category of individual. The design of the CAM 10 is based on the assumption that the airborne DU activity concentration of interest is that which could result in a lifetime committed effective dose of 500 mrem/yr or greater (500 mrem/yr is 10 percent of the radiation protection standard for occupational radiation workers) and 50 mrem/yr or greater (50 mrem/yr is half the radiation protection limit for members of the general public; i.e., 100 mrem/yr effective dose commitment). There are alternative design objectives that can be established for the CAM 10, which would require different alarm set points that are discussed below.

A review of EPA 1999[2] reveals that the inhalation committed effective dose conversion factor for adults for insoluble particles of U-238, which is the form of uranium that is of primary interest during remediation, is 8.04E-06 Sv/Bq for adult workers exposed to particles of DU that are in the respirable range of 5-micron activity median aerodynamic diameter (AMAD). For members of the general public, the limiting effective dose conversion factor is 2.85E-5 Sv/Bq. This is the highest inhalation effective dose conversion factor for insoluble uranium and applies to infants. For other age groups, the dose conversion factor is slightly less restrictive. For particles with a smaller than 5-micron AMAD, the dose conversion factors can be higher than those for 5-micron AMAD.

[2] The inhalation dose conversion factors recommended by the EPA in Federal Guidance Report No 13 are conveniently and more completely tabulated in a CD prepared by the International Commission on Radiation Protection (ICRP) Version 2.01 for Windows 95/98/Me/NT/2000 titled "ICRP Database of Dose Coefficients: Workers and Member of the Public," ISBN 0 08 043 8768 Distributed by Elsevier Science Ltd. Pergamon.

Given these dose conversion factors, the concentration (C) of U-238 in air that could result in a committed effective dose of 500 mrem/yr to exposed workers and 50 mrem/yr to exposed members of the public may be calculated as follows:

Radiation Workers $$Cw = Dw \div (DCFw) \times Bw \times a \times b$$

where:

$Cw$=the concentration of uranium in air that would result in 500 mrem/yr to radiation workers under continuous exposure or a 2000-hour work year (Bq/m$^3$)

$Dw$=the annual lifetime committed effective dose corresponding to 10 percent of the limit for occupational radiation workers (mrem/yr)

$DCFw$=the inhalation dose conversion factor for workers exposed to insoluble forms of U-238 aerosols with an AMAD of 5 microns (Sv/Bq)

$Bw$=Breathing rate for adult males during light work activity (m$^3$/hr)

a=unit conversion factor (mrem/Sv)

b=unit conversion factor (work hours per year)

Inserting the values for each parameter, the calculation is as follows:

$$Cw \text{ (Bq/m}^3\text{)}=500 \text{ mrem/yr} \div (8.04\text{E-6 Sv/Bq} \times 1.0\text{E5}$$
$$\text{mrem/Sv} \times 1.2 \text{ m}^3/\text{hr} \times 2000 \text{ hr/yr});$$

$$Cw=0.25 \text{ Bq/m}^3=7 \text{ pCi/m}^3$$

Members of the General Public $$Cp = Dp \div (DCFp) \times Bp \times a \times b$$

where:

$Cp$=the concentration of uranium in air that would result in 50 mrem/yr for full time exposures to the limiting members of the general public (Bq/m$^3$)

$Dp$=the annual lifetime committed effective dose corresponding to 50 percent of the limit for radiation exposures to members of the general public (mrem/yr)

$DCFw$=the inhalation dose conversion factor for the limiting members of the general public exposed to insoluble forms of U-238 aerosols with an AMAD of 5 microns (Sv/Bq)

$Bw$=breathing rate for the limiting members of the general public (m$^3$/day)

a=unit conversion factor (mrem/Sv)

b=unit conversion factor (days per year)

Inserting the values for each parameter, the calculation is as follows:

$$Cp \text{ (Bq/m}^3\text{)}=50 \text{ mrem/yr} \div (2.85\text{E-5 Sv/Bq} \times 1.0\text{E5}$$
$$\text{mrem/Sv} \times 5.4 \text{ m}^3/\text{day} \times 365 \text{ days per year})$$

$$Cp=8.9\text{E-3 Bq/m}^3=0.24 \text{ pCi/m}^3$$

These calculations indicate that a real time, continuous air sampling monitor that could detect 7 pCi/m$^3$ of DU (in this calculation it is assumed that the DU is entirely U-238; in reality, a small fraction (about 10%) of the measured alpha activity is from U-234 plus U-235) in the respirable range would be useful for ensuring the protection of any radiation worker who may be exposed to airborne DU. The CAM 10 can detect and record DU concentrations well below 7 pCi/m$^3$. In addition, for members of the public (particularly children who may be exposed 8760 hours per year), it would be desirable to detect 0.24 pCi/m$^3$ of DU. These are useful benchmarks, but alternative benchmarks could be employed. For example, the radiation protection standards for radiation workers involved in work licensed by the U.S. Nuclear Regulatory Commission (NRC) and Agreement States are set forth in Part 20 of Title 10 of the Code of Federal Regulations (10CFR20). Appendix B of that regulation establishes an airborne concentration limit for insoluble U-238 uranium particles of 2E-11 pCi/ml for workers and 6E-14 pCi/ml for members of the general public, referred to as Derived Air Concentrations (DACs). These concentrations correspond to 24 pCi/m$^3$ for radiation workers and 0.06 pCi/m$^3$ for members of the public. In order to meet these or other objectives, the design of the CAM 10 would not be affected, but the operational characteristics of the CAM 10 may need to be modified, including air sampling flow rate, air sampling time, and duration of counting the air samples in a manner that will allow clear and unambiguous output that would indicate when the airborne concentration of DU exceeds concentrations of concern. These matters are addressed in detail below.

Two questions emerge from these calculations. Can such exposures and associated airborne concentrations of DU actually occur during the cleanup of a DU site, and can a continuous real-time monitor (i.e., the CAM 10) be designed that can detect these, or possibly lower, concentrations of airborne DU?

With respect to the first question, assume that the soil at a DU site contains 9.61E4 Bq/kg (2,595 pCi/g) as cited above in the paper by Choy, et. al., 2006. During remediation, it would not be unusual for the airborne dust concentration to reach one mg/m$^3$. The subject of outdoor air dust concentrations (sometimes also referred to as outdoor airborne dust loadings) is reviewed in Kennedy et al., 1992, (referred to as NUREG/CR-5512). In that review, a number of document findings are described, as follows:[3]

[3] The following are the citations for the references cited in this quote:

Stern, A. C. 1968, 2$^{nd}$ edition, Academic press, N.Y.

HEW 1969, U.S. Department of Health and Human Services, "Air Quality Criteria for Particulate Matter," HEW, Washington, D.C.

MaGill, P. L., R. R. Holden, and C. Ackley, eds. 1956. Air Pollution Handbook. McGraw Hill, N.Y.

Sehmel, G. A. 1974. "Particle Resuspension from and Asphalt Road." Atmosphere-Surface Exchange of Particulate and Gaseous Pollutants. Conf. 740921, U.S. Atomic Energy Agency, Washington, D.C.

Sehmel, G. A. 1975. Atmospheric Dust Size Distribution as a Function of Wind Speed. In Pacific Northwest Laboratory Report for 1974, BNWL-1950-3, Pacific Northwest Laboratory, Richland, Wash.

Sehmel, G. A. 1977a. Transuranic and Trace Simulant Resuspension. BNWL-SA-6236, Pacific Northwest Laboratory, Richland, Wash.

Sehmel, G. A. 1977b. Radioactive Particle Resuspension Research on the Hanford Reservation. BNWL-2081. Pacific Northwest Laboratory, Richland, Wash.

Sehmel, G. A. 1980. Particle Resuspension: A Review. Environ. Int. 4:107-127.

Sehmel, G. A. 1984. Deposition and Resuspension. In Atmospheric Science and Power Production.

DOE/TIC-27601, U.S. Department of Energy, Washington, D.C.

Sinclair, P. C. 1976. Vertical Transport of Desert Particulates by Dust Devils and Clear Thermals. Atmosphere-Surface Exchange of Particulate and Gaseous Pollutants. Conf. 740921, U.S. Department of Energy, Wash.

Soldat, J. K. et al, et al. 1973, "Assessment of Environmental Impact of the Retrievable Surface Storage Facility," BNWL-B-313, Pacific Northwest Laboratory, Richland, Wash.

Anspaugh, L. et al. 1974, resuspension and Redistribution of Plutonium in Soils," Health Physics 29:571-582

For outdoor air concentrations, a number of references are provided for a wide variety of situations. In Air Pollution, Vol 1 (Stern 1968), measurements from the National Air Sampling Network for urban situations are summarized for the period 1957-1963. Chemical analyses for suspended particles (soot and ash) of 14,494 urban and 3,114 non-urban samples in the United States yielded a geometric mean of 98 $\mu g/m^3$, with a maximum of 1706 $\mu g/m^3$. Information in Air Quality for Particulate Matter (HEW 1969) indicated that . . . average suspended mass concentrations range from about 10 $\mu g/m^3$ in remote nonurban areas to about 60 $\mu g/m^3$ near urban locations. In urban areas, averages range from 60 $\mu g/m^3$ to 220 $\mu g/m^3$, depending on the size of the city and its industrial activity.

The Air Pollution Handbook (MaGill, Holden, and Ackley 1956) reported that suspended particles in the atmosphere of a number of communities in the United States can range from 100 $\mu g/m^3$ to 1000 to 2000 $\mu g/m^3$ . . . .

Upper and lower limits of airborne-soil mass-loadings as a function of particle size were estimated for the Hanford Site near Richland, Wash. (Sehmel 1975, 1977a, 1984). The volume distributions were for wind erosion, without mechanical disturbance, for a semi-arid climate. For particulate sizes less than 10 $\mu m$, the upper limit for mass loading was estimated to be about 700 $\mu g/m^3$. For particle diameters less than 10 $\mu g$, the upper limit for mass loading was 232,000 $\mu g/m^3$. The effect of mechanical disturbance is to create somewhat higher localized air concentrations than for wind erosion alone. For comparison, relatively clean air has a dust loading [note that in this reference, the term "dust loading" corresponds to the airborne concentration of particulates material] of about 20 $\mu g/m^3$ (Sehmel 1977b); a dust loading of 110,000 $\mu g/m^3$ is barely tolerable for breathing (Stewart 1964); and the dust concentration measured in a dust devil (whirlwind) is approximately 5 $g/m^3$ (Sinclair 1976).

Previous estimates have been made to determine a long-term average dust-loading for purposes of radiation dose assessment. A 1973 study assessed the potential environmental impacts of the interim storage of commercial high-level waste in a retrievable surface storage (Soldat et al. 1973). This high level waste assessment used an average atmospheric dust loading of 100 $\mu g/m^3$ as being a typical annual average dust-loading. In 1975, Anspaugh et al. suggested the use of 100 $\mu g/m^3$ for predictive purposes. This value was partly based on measurements for 30 nonurban locations with arithmetic averages from 9 to 70 $\mu g/m^3$ (Anspaugh et al. 1975).

Under these conditions (i.e., those of Kennedy et al., 1992), the activity concentration of DU in the air would be 2.5 $pCi/m^3$. The implications are that the airborne concentration may approach the activity concentration of interest for radiation workers (i.e., 7 $pCi/m^3$ for a 5-micron AMAD) under fairly dusty conditions and exceed the concentrations of concern under highly dusty conditions at a DU remediation site.

With respect to members of the public, the chronic (chronic refers to airborne concentrations of DU aerosols that remain elevated for protracted periods of time over the course of a year but can fluctuate during that time period) aerosol dust concentration is unlikely to exceed about $\frac{1}{10}$th the level at the remediation site or about 0.1 $mg/m^3$. Under these conditions, the airborne concentration of DU would be 0.25 $pCi/m^3$, which, coincidentally, is the approximate activity concentration of interest for the protection of the public (i.e., 0.24 $pCi/m^3$).

From the perspective of members of the public, pathways other than inhalation might also be of concern. These exposure scenarios would be those that occur during and after remediation activities have ceased, but offsite contamination might persist in the environment for extended periods of time. Three exposure scenarios can be used to conceptualize these offsite exposure pathways. The first is if the contamination settles on the soil surface and erodes away rapidly (due primarily to wind and/or rain) and is deposited in a nearby body of water. This scenario results in virtually no exposures. The second scenario is if airborne DU is transported offsite and results in a cumulative soil surface contamination. The inventor estimates a reference offsite cumulative soil surface contamination of 2.2E6 $pCi/m^2$ per $pCi/m^3$ of chronic levels of airborne DU at the location of an offsite resident. The method used to derive this value is described below. Assuming this activity does not erode away but comingles with surface soil to a shallow depth of about one cm, the annual dose to individuals residing at such a location would be about 1.58 mrem/yr per $pCi/m^3$ of chronic airborne concentrations of DU. This exposure occurs due to the deposition and resuspension of deposited uranium. Depleted uranium deposited onto soil can result in external exposure and also internal exposure due to the resuspension and inhalation of the deposited uranium.

The third scenario is if the deposited DU co-mingles more deeply into the soil due to tilling the soil. In this scenario, other pathways of exposure come into play, such as food ingestion after the uranium deposits onto the ground. The computer code RESRAD is useful in exploring the potential exposures associated with these other pathways (Yu et al 1993a and Yu et al 1993b). Zhang et al., 2014 present a review of the literature on dust deposition velocities and the results of their own experiments. Depending on particle size, wind speed, surface conditions, and atmospheric conditions, the deposition velocity can vary widely, reportedly ranging from 0.1 to 1.28 m/sec in the published literature. Zhang et al., 2014 shows results consistent with the literature review. Based on Zhang et al., 2014, the example presented herein assumes a chronic airborne DU concentration of about one $pCi/m^3$, and that uranium aerosol is depositing at a rate of 0.7 m/sec resulting in the activity concentration of DU accumulating on the ground over the course of a year to be 2.2E6 pCi/m². This assumes no natural attenuation in the soil, which finds support in Yu et al., 1993. This reference includes a literature review that reveals that the erosion rate varies with the characteristics of the soil, slope of the land, weather, wind, rainfall, types of vegetation, etc. Based on Yu et al., 1993, the example uses an erosion rate of one cm/yr. For the purpose of a conservative short-term analysis, the inventor elected to ignore erosion in this scenario because it has very little effect on the results of the calculation. In agricultura soil, it can be assumed that that tilling of the land would distribute the DU to the root zone of vegetation, or about 15 cm. On this basis, the activity concentration of DU in soil offsite can be estimated to be about 7.3 pCi/g at the end of one year of deposition, assuming the airborne activity concentration of DU is chronically at one pCi/m³.

RESRAD and its default parameters then are used to derive the anticipated radiation doses to members of the public at offsite locations due to this level of contamination in soil for a number of exposure pathways. The results of this analysis reveal a peak dose of 0.78 mrem/yr per pCi/m³ of U-238 chronically airborne at the location of the offsite receptor for one year.

These calculations indicate that individuals located offsite could experience 50 mrem/yr effective dose commitment from inhalation of the passing plume of DU as it is produced from a variety of mechanisms that result in the resuspension of DU present in soil (e.g., during remediation, vehicular disturbance, and/or wind erosion). In addition, assuming one year of remediation, individuals offsite could also experience about one mrem per year from DU deposited onto soil after work has terminated, assuming that the chronic airborne activity concentration of DU is one pCi/m³. Hence, an alarm set point of 0.24 pCi/m³ serves a design objective of the CAM 10 that ensures that operators are notified when the concentration of airborne uranium is at a level that begins to approach exposures to any member of the public in excess of 100 mrem/yr if the airborne particulate mass concentration remained at the derived elevated levels for protracted periods of time.

The implications of these calculations are that periodic grab samples (e.g., daily or weekly) followed by laboratory analysis for DU may be adequate to ensure that the levels of airborne DU can be managed well below applicable radiation protection standards. However, members of the public may prefer a continuous monitor that would be able to detect the presence of elevated levels of DU as soon as possible. One of the other advantages of the CAM 10 is that changes in airborne dust loading can be readily correlated with changes in cleanup operations as they occur. This is useful as a way to optimize protection of workers and the public by understanding what practices and conditions are associated with episodic increases in the concentrations of airborne DU so that corrective actions could be quickly implemented.

Considering the above radiological conditions and a desire to show protection for both radiation workers and members of the public, the CAM 10 is expected to meet the following specifications, which will be confirmed by testing a CAM 10 prototype:
1. minimize the amount of dust (i.e., the dust loading) that would accumulate on a filter (e.g., the web 46) during sampling such that the dust does not degrade the energy distribution of the alpha particles emitted by DU on the filter,
2. use a sensor that discriminates between the amount of alpha particles emitted by DU on the web 46 and alpha particles from other radionuclides that might be on the web 46, and
3. measure the amount of DU on the web 46 at a level of sensitivity that does not require a large amount of DU and/or counting time to determine if the airborne activity concentrations of DU exceed acceptable levels for radiation workers and members of the public.

The description that follows explores the degree to which the CAM 10 meets these specifications as applied to the protection of radiation workers and as applied to the protection of members of the public. In the case of radiation workers, the CAM 10 should be able to detect 7 pCi/m³ and in a second case, the CAM 10 should be able to detect 0.24 pCi/m³.

Protecting Radiation Workers

The starting point for evaluating whether it is possible to meet these specifications as applied to radiation workers is selecting the air flow rate entering the CAM 10. For the purpose of this analysis, let us assume the following:
1. A continuous air sampling rate of about 10 liters per minute for about one hour and a concentration of DU in the air in the respirable range of 7 pCi/m³. This flow rate and sampling time can be adjusted as needed to achieve the objectives of the CAM 10. Ten liters per minute was selected because a conventional battery powered air mover can easily achieve this flow rate for an extended period of time before the batteries need to be charged or replaced. A one-hour sampling time was selected in this example because it can be considered close enough to real time to meet the need for an early indication of changing conditions.
2. An average airborne particulate concentration ranging from of 0.1 to 1.0 mg/m³ on site and no more than 0.1 mg/m³ at the site boundary and offsite for extended periods of time. Kennedy, et al., 1992 (NUREG/CR-5512) present a review of the outdoor airborne dust concentration under a broad range of conditions. Under these hypothetical circumstances, the amount of DU that would deposit on the web 46 would be about 4 pCi for a sampling time of about one hour.

A typical solid-state detector will likely be able to detect the presence of 4 pCi of U-238 on the web 46 by accumulating counts for one hour. Four pCi on the web 46 corresponds to about 9 disintegrations per minute and 533 disintegrations per hour (i.e., 4 pCi×0.037 dps per pCi×3600 sec/hr=533 disintegrations) or about 160 counts in one hour of counting, assuming an approximate 30% counting efficiency above instrument background, which is likely to be less than one count per hour. For example, the web site for the AMETEK ORTEC AlphaSuite alpha spectrometers, cites a detector efficiency of >25% and a background count rate of <1 count per hour for alpha emissions above 3 MeV based on their BU-020-450-AS detector, which is one inch in diameter and under vacuum conditions. However, this count level of 160 counts in one hour is based on the assumption that the dust loading (mg/cm²) on the web 46 will not degrade the energy of the alpha particles before they reach the detector. This issue of dust loading is discussed below. In addition, solid state detectors that currently are used to measure airborne alpha emitters usually operate in a vacuum to avoid degradation of the alpha energy distribution by the air space between the filter and the detector. However, as discussed below, Applicant believes, based on careful reasoning and study, that in the scenario of DU site monitoring discussed herein, if the detector 60 is not placed in a vacuum, the energy distribution of the alpha particles will not be substantively degraded, and the detector 60 should be able to provide a clear and unambiguous signal when the airborne activity concentration of DU is above 7 pCi/m³ and the detector is placed close (about 2 mm or less) to the web 46. This is a matter that will be confirmed through testing.

One confounding variable is the possibility of a false positive, which could occur if there are other alpha emitters present in the sample. There are certainly a large number of alpha emitters that might be airborne at a given site. However, the only alpha emitters that are ubiquitous at all sites and that need to be taken into consideration in the design and operation of the CAM 10 are the short-lived progeny of Rn-222 (radon), which include Po-218 (6.114 MeV alpha) and Po-214 (7.833 MeV alpha). Other naturally naturally occurring alpha emitters in soil associated with the U-238 and Th-232 radioactive decay series are at levels that cannot substantively affect the alpha dust loading of interest to this application. For example, the concentration of naturally occurring U-238 in soil is approximately one (1) pCi/g (see Table 4.3 (page 61) of NCRP 1987), which is orders of magnitude below the concentration of DU in soil at sites where this monitor is intended for use.

In a typical outdoor environment (not including sites with elevated levels of radium), the outdoor concentration of radon is on the order of 270 pCi/m³ (see Table 24 (page 73) of UNSCEAR 1993), and its progeny include particulate alpha emitters, namely Po-218 and Po-214. This short-lived radon progeny rarely are in equilibrium with their parent. For example, paragraph 135, pg. 54 of UNSCEAR 1993 reports equilibrium fractions of 0.4 indoors and 0.7 outdoors. Also, note that their concentrations in air are close to three orders of magnitude greater than the concentrations of U-238 that are of interest here (e.g., 270 pCi/m³×0.6÷0.24 pCi/m³=788). Under these conditions, the alpha emitters associated with Po-218 and Po-214 present on the web 46 could result in a false positive because their natural presence in the atmosphere is so much greater than the concentrations of U-238 that are of interest here (i.e., 7 pCi/m³ for workers and 0.24 pCi/m³ for members of the general public). The following explores the mitigating factors and potential challenges posed by Po-218 and Po-214.

One mitigating factor is the relatively short half-life of Po-218 (3 minutes). Because of its relatively short half-life, Po-218 will not continually build up on the web 46 for the entire one-hour time period of sampling and, once sampling ceases, will decay away quickly, as demonstrated by the following calculations.

Assume that the outdoor concentration of Po-218 is 0.7×270 pCi/m³ (e.g., 189 pCi/m³), and it is being continuously deposited onto the web 46 at a rate of 10 L/min. At equilibrium, the amount of Po-218 on the filter will be:

189 pCi/m³×10 L/min×1E-3 m³/L÷(0.693/3 min)=8.2 pCi.

The activity of U-238 on the web 46 after one hour of filtration at 10 L/min, with the U-238 concentration at 7 pCi/m³ will result in 4 pCi on the web 46. Hence the concentration on the web 46 of U-238 would be comparable to that of Po-218. If counting is delayed for example, for 15 minutes, the concentration of Po-218 at the beginning of the count will decrease 32-fold to 0.26 pCi due to radioactive decay, and will continue to decay during counting. As such, the example assumes Po-218 will not contribute significant counts to the DU region of interest and should not interfere with the protection of workers.

The Po-214 is potentially more problematic than Po-218. Although Po-214 has a very short half-life, it will be continually replenished by its parent, Bi-214 (a beta emitter with a 20-minute half-life), which will also be present and build up on the web 46. It is convenient to think of the alpha emissions associated with Po-214 as if they belonged to Bi-214. On that basis, the concentration of Bi-214/Po-214 on the web 46 can be derived as follows:

189 pCi/m³×10 L/min×1E-3 m³/L (1−exp(−λt))÷(0.693/20 min)=1.89 pCi/min (1−0.13)÷0.963/ 20 min=42 pCi.

Hence, after one hour of filtration at 10 L/min, the Po-214 activity on the web 46 will be 42 pCi, while the concentration of U-238 will be 4 pCi. The Po-214 will decay, but not substantially, during counting for one hour because of the 20-minute half-life of Bi-214. This raises concerns that the Po-214 might contribute counts to the U-238 region of interest (the region of interest is the energy band in Mev (about 3.8 to 4.2 Mev for U-238) where most if not all the electron pulses produced by the alpha particles striking the detector 60 fall). However, this problem should be manageable because the region of interest for U-238 counting can be isolated from the region of interest of the alphas from Po-214 (alphas of 7.833 Mev). This challenge is greater when the U-238 concentration of interest is 0.24 pCi/m³ for protecting members of the public.

A mitigating factor, especially with respect to Po-214, is the high resolution of solid state alpha detectors, such as the detector 60. Because of the high resolution of detector 60, very few of the pulses associated with the Po-218 and Po-214 are expected to fall into the energy region of interest associated with the alpha emissions from U-238. It is noteworthy that all other alpha spectrometers employ algorithms referred to as "spectral stripping" as a means to subtract out counts from alpha emission from one or more radionuclides from contributing counts to the region of interest of another radionuclide. These algorithms are complex and can contribute to errors in the derived quantities of a given radionuclide on a filter sample. The detector described herein does not use such algorithms. Instead, the detector 60 counts the number of electronic pulses that fall within the energy region of interest for U-238. The detector 60 can do this because there will be no significant counts in this region of interest from radionuclides other than U-238.

Figure 7:
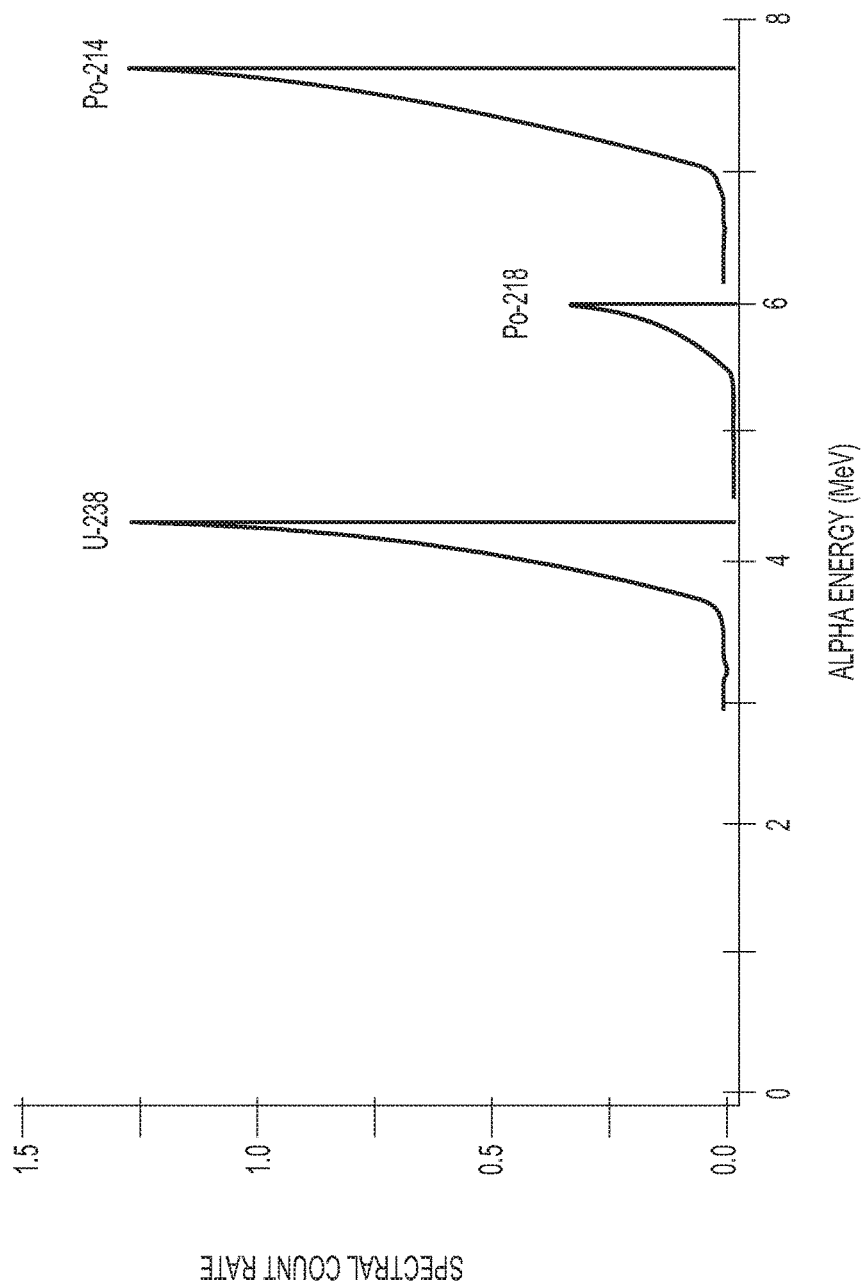
FIG. 7 illustrates a conceptual energy spectrum verses counts for radionuclides included in samples collected by the monitor of FIG. 1.

FIG. 7 presents a conceptual characterization of the energy spectrum of the primary alpha emissions associated with U-238, Po-218, and Pb-214. The actual relative height and width of each spike will be determined experimentally during testing and production of the CAM 10. Note that when a given alpha particle impinges on the solid-state detector 60, the alpha particle generates an electronic pulse that has a maximum size corresponding to the energy of the alpha particle. However, there will also be pulses generated that are slightly smaller than the maximum energy of the alpha particle, referred to herein as straggling. The implications are that some of the pulses produced in the detector 60 by a given energy alpha particle will also fall into energy regions below the maximum energy of the alpha particle. Hence, it is possible that these lower energy pulses could fall into energy regions associated with radionuclides present on the sample with lower alpha energy emission, resulting in false positive readings for the radionuclides with the lower energy alpha emissions.

To a large extent, this problem can be accounted for by setting the energy discriminator of the detector 60 such that the detector 60 counts pulses only within a given energy window. However, if the energies of the alpha emissions from different radionuclides present in the sample are close together (i.e., within a few tenths of an MeV), it is possible that there will be difficulty discriminating the number of atoms of one alpha emitter in the sample from another, lower energy, alpha emitter in the sample (see Table 2). This is in fact the case for counting the amount of Pu-239 in a sample that also contains Po-218. The reason is the energy of the alpha particle emitted by Pu-239 (5.1 MeV) is somewhat close to the energy of the alpha particles emitted by Po-218 (6.114 MeV) (also see FIG. 1 in Seiler, et al. 1988). However, in the case of U-238, the alpha energy is 4.2 MeV, well below the alpha energy of Po-218. The implications are that the presence of Po-218 in the sample, even in relatively large quantities and even in the presence of air (i.e., no vacuum), will not deliver a substantial number of counts in the energy region of interest with respect to U-238.

The degree to which this might occur depends on the height of the Po-218 spike and the degree to which its alpha emissions might be attenuated when traveling from the web 46 to the detector 60. The issue of alpha attenuation was researched by and described in Huang, et al., 2002. In that reference, the authors found that alpha attenuation is not an issue as long as the thickness of the aerosol deposit (i.e., the dust loading) on the web 46 is less than 0.1 mg/cm$^2$. As discussed below, for the CAM 10, the dust loading on the web 46 might reach 0.09 mg/cm$^2$ based on an air flow rate of 10 L/m, one hour of sampling, and an ambient particulate mass concentration of one mg/m$^3$. Huang, et al., 2002 also provides a review of other publications on this subject. Of particular interest, Stevens et al., 1963 show that for membrane and glass fiber filters the presence of nonradioactive dust caused serious reduction in energy resolution for dust exceeding ~0.4 mg/cm$^2$. Table 2 presents the results of the Huang, et. al., 2002 investigations with Po-218 (6.114 MeV alpha).

TABLE 2

Effect of Dust loading on Resolution (Full width at half maximum, FWHM)

| Type of Aerosol | Isotope | Alpha Energy (MeV) | Dust Loading (mg/cm$^2$) | FWHM (keV) |
|---|---|---|---|---|
| Glass Beads (3-10 microns) | Po-218 | 6.0 | 0 | 296 +/− 36 |
|  |  |  | 0.62 | 357 +/− 33 |
|  |  |  | 2.5 | 337 +/− 47 |
| Iron Oxide (0.3-0.8 microns) |  |  | 0 | 300 +/− 33 |
|  |  |  | 0.58 | 286 +/− 13 |
|  |  |  | 5.6 | 272 +/− 24 |
| Unattached Radon Decay products |  |  | 0 | 170 +/− 40 |
|  |  |  | 0.37 | 105 +/− 16 |
|  |  |  | 11 | 125 +/− 11 |

On this basis, it does not appear that the dust loading on the web 46 will result in a deterioration of the energy resolution for the alpha emissions from particulates on the web 46 to such an extent that attenuation of the Po-218 and Po-214 alpha peaks will deposit a substantial number of counts in the energy region of interest associated with U-238, even if the quantity of radon progeny on the web 46 is significantly larger than that of U-238.

The final and possibly the most important issue has to do with the possibility that so much dust will deposit on the web 46 that any alpha particles emitted by U-238 in the sample will be substantively degraded and/or never reach the detector and result in false negative readings. In order to evaluate this issue, the inventor assumed a typical high end chronic outdoor airborne particulate mass concentration of one mg/m$^3$ and an air sampling rate of 10 L/min. The total amount of dust deposited on the web 46 during one hour of sampling would be about 0.6 mg. Assuming a 1-inch diameter sample, the thickness of the dust deposit on the web 46 would be 0.6 mg÷6.45 cm$^2$=0.09 mg/cm$^2$ at an airborne dust concentration of one mg/m$^3$. Assuming a dust density of 2 g/cm$^3$, the thickness of the layer of dust on the web 46 after one hour of filtration would be 4.5E-5 cm. This thickness of dust is not expected to substantively attenuate the alpha emissions from U-238. This conclusion is based on the alpha range information provided in Table 3.

TABLE 3

Range of 4.2-MeV Alphas*

| Material | Density (g/cm$^3$) | Range g/cm$^2$ | cm | μm |
|---|---|---|---|---|
| Air (dry near sea level) | 1.20E-03 | 3.34E-03 | 2.78 | — |
| Water | 1 | 2.88E-03 | 2.88E-03 | 28.8 |
| Aluminum Oxide | 3.72 | 1.13E-03 | 2.36E-03 | 23.6 |
| Silicone | 2.33 | 4.34E-03 | 1.85E-03 | 18.5 |
| DUO2** | 1.73 | 9.68E-03 | 5.60E-03 | 56.0 |
| DUO2** | 10.97 | 9.68E-03 | 8.82E-04 | 8.8 |

*National Institute of Science and Technology, Physics Measurements Laboratory: astar-stopping power and range tables for helium nuclei. http://physics.nist.gov/PhysRefData/Star/Text/ASTAR.html.
**These are estimated values. In one case, the uranium oxide is assumed to settle as a dust and is not compacted on the filter and has a bulk density of 1.73. In the second case, the uranium oxide is assumed to be a solid metal oxide. The former is likely to be a more realistic value.

The implications of Table 3 are that the range of the alpha particles emitted by U-238 in the dust deposited on the web 46 would likely be much greater than the thickness of the dust on the web 46 assuming a one-hour sampling duration at an air flow rate of 10 L per minute. As such, self-attenuation within the deposited dust sample is not expected to undermine the ability of the instrument to perform its intended function.

Table 3 also reveals that it is essential that the solid-state detector 60 is located very close to the web 46 (perhaps only a few mm). If the distance between the web 46 and the detector 60 approaches 3 cm, it would be necessary for the housing containing the filter and the detector to be placed in an evacuated chamber. It is for this reason that many alpha spectrometry units employ a vacuum chamber. However, the inventor believes that an evacuated chamber is not needed as long as there is assurance that the distance between the filter and the detector can be maintained at a few mm. For this detector, the gap between the detector 60 and the web 46 may be adjustable.

One additional possible problem with such a design is that, due to electrostatic forces produced during the movement of the web 46 or electrostatic charge contained in the web 46 itself, some particles of dust on the web 46 might deposit and buildup on the surface of the detector 60. Such a buildup would gradually increase the "background" counts of the detector 60, resulting in false positives. One solution to this problem is covering the detector 60 (and perhaps the entire interior of the counting chamber) with an ultrathin superhydrophobic coating to mitigate electrostatic deposition of particles on the detector 60. Typical materials include proprietary polymer emulsions, such as Ultra-Ever Dry™, at thicknesses below on micron (1E-6 cm) and proprietary nanometer scale patterned silica or other nanomaterial coatings. Another possible solution to this problem could be STOPStatic.com, which consists of metal rods or strands that drain electrostatic charge. During testing of the CAM 10, particular attention will be given to this possible issue.

Radiation Protection of the Public

In order to help ensure protection of the public, it would be desirable for the CAM 10 to be able to detect airborne DU concentrations of 0.24 pCi/m$^3$. If the airborne concentration of DU is 0.24 pCi/m$^3$, 19 disintegrations would be experienced by a monitor with a flow rate of 10 L/min, a sample collection period of one hour, and a counting time of one hour. Again, assuming the monitor is 30% efficient, the total count rate would be about 6 counts per hour following the one-hour sample collection. Since the background count of alpha spectrometers is less than one count per hour, it should be possible to determine if the average concentration of DU in air on an hourly basis and also determine if the average hourly airborne concentration of DU is above 0.24 pCi/m$^3$. Issues related to false positives and false negatives discussed above for monitoring workers apply even more so to monitoring of members of the public. However, as discussed above, the inventor believed these issues are manageable and would be confirmed during testing of the CAM 10.

The inventor recognized that, rather than recording the average airborne concentration on an hourly basis, it would be desirable to report and plot the airborne activity concentration of respirable DU continuously. This can be accomplished by taking advantage of the component of the herein disclosed instrument that continuously records the airborne particulate concentration (mg/m$^3$). In addition to deriving the average airborne activity concentration of DU (pCi/m$^3$) for a given one-hour period, the CAM 10 also may derive the activity concentration of DU in the sample on the web 46, expressed in units of pCi/mg. The instrument will be able to do this using the continuous air flow monitor (liters/min) and its associated continuous airborne dust concentration monitor (mg/m$^3$). Once the average activity concentration of DU in the air over a given hour is determined, an estimate can be made of the air concentration as a function of time for the previous hour in units of pCi/m$^3$. After the first two-hour period (one hour to collect the sample and one hour to count the sample), a reasonable estimate of the concentration of respirable DU in air in units of pCi/mg of aerosol can be made. Going forward in time after that first two-hour period, the data characterizing the airborne aerosol concentration (mg/m$^3$) can be used, such that the aerosol concentration is continuously being recorded and knowledge is acquired of the concentration of DU associated with the aerosol (pCi/mg) to continuously report and record the airborne concentration of DU on the aerosol (pCi/m$^3$); i.e., a continuous real-time monitor. At the end of the next hour, this estimate will be validated by using the measured concentration and amount of DU on of the next hourly sample. This approach to continuously monitoring and recording the airborne concentration of DU is based on the premise that the concentration of DU in the aerosols (pCi/mg) will remain fairly unchanged during the course of any given hour. If a significant change does occur during the course of a given one-hour period, it will be detected and corrected at the next hourly count. In this way, not only is there a measurement of the average hourly respirable airborne concentration of DU and the average hourly concentration of DU in the solids deposited on the filter (which serve as our hourly anchor), a reasonable estimate is made of the time varying concentration of respirable DU on a continuous basis by continuously recording the airborne aerosol concentration in mg/m$^3$.

Conceptual Design of the CAM 10

A conceptual design of a continuous, real time monitor (i.e., the CAM 10) is now described for detecting the presence of DU in air at concentrations in excess of the levels that are of concern with respect to protecting radiation workers and members of the public. The conceptual design refers to elements and components of the CAM 10 illustrated in FIGS. 1-4B.

Considering aerosols that are in the respirable range, (i.e., less than about 10 microns aerodynamic diameter), there are a number of approaches that may be used to ensure that the aerodynamic diameter of the particles is known and accounted for in recording the airborne concentration of respirable particles of DU and establishing appropriate alarm set points. One approach would be to first pass the air flow through a gross particulate filter (e.g., filter 21) to remove airborne dust particles above the respirable range (above 10 microns). Changes in the air flow rate would indicate when the gross particulate dust loading is so great that it might be impeding the sampling of respirable particles of DU. The air flow would then pass by a particle size detector (e.g., the detector in mechanism 30) that would measure the particle size distribution using methods that would not affect the concentration of the respirable particulates in the air steam and would also measure the airborne aerosol concentration in the air (mg/m$^3$). Alternatively, the air flow can be drawn through a horizontal elutriator system, such as the MRE Type 113A gravimetric as described in Chapter 9 of *Aerosol Science for Industrial Hygienists*, by James H. Vincent, Pergamon, 1995. This type of device results in the collection of respirable aerosols on a filter. Other commercially available devices that can be used to characterize airborne concentration of dust particles and the aerodynamic diameter distribution of aerosols are described in the James H. Vincent reference.

The air flow would then pass through a movable (e.g., a type of conveyor belt) Teflon®, glass fiber, paper, or other type of filter (the web 46) onto which air particulates would be allowed to deposit for approximately one hour (i.e., at station 46A). The web 46 with the deposited dust will move to the next stage (i.e., at station 46B), where the web 46 will be positioned just beneath solid state alpha detector 60. This will be a light tight counting chamber which will preclude the production of pulses due to light which would interfere with counting pulses associated with the alpha emissions from U-238. With the web 46 placed immediately beneath the solid-state detector 60 at a distance less than a few mm, counts will be accumulated in an energy window (the region of interest) that begins at about 3.8 MeV and ends at about 4.2 MeV; i.e., the energy of most of the alpha emissions from U-238. Counting may be delayed for about 15 minutes to allow most of the Po-218 to decay away and then counts in the region of interest may be collected for approximately one hour before the web 46 moves on to measure the U-238 alpha emissions present in the next spot on the web 46.

The counts associated with each web 46 air sample spot (i.e., the air sample collected at station 46A) will be recorded and time stamped. These counts will be indicative of the average concentration of respirable DU in air over the previous one hour counting period (pCi/m$^3$) and also the average concentration of U-238 in the respirable airborne particles (pCi/mg). The CAM 10 may alarm if (1) the number of counts accumulated over any one-hour period at the location of radiation workers exceeds that associated with a DU air concentration of 7 pCi/m³ or (2) if the number of counts accumulated over any one-hour period at the remediation boundary or offsite locations exceeds that associated with a respirable airborne DU activity concentration of 0.24 pCi/m³. During testing of the CAM 10, sample collection time, air mover flow rates, counting intervals, etc. will be optimized to achieve these goals. In addition, the need for mitigation of electronic charge accumulation (electrostatic charge) will be investigated.

Based on the above analysis, the CAM 10 will be tested to confirm its desired performance. In addition, while the CAM 10 is being used in real time, concurrent continuous air samples will be collected adjacent to the locations of the real-time monitors, along with any lapel monitors worn by workers. The lapel filters will be changed after each worker shift and the general air samples filters will be changed out according to the standard practice used at the facility, and analyzed for DU using conventional radio-analytical methods by a laboratory accredited for such analyses. The amounts and concentrations of DU as obtained from the lapel and general sample monitors using laboratory analyses will be compared with the results of the real-time monitor as a means to verify that the real-time monitor is providing valid results.

As noted above, incorporated into the design of the CAM 10 are two features that will help to optimize the functionality of the device and allow for recording the real-time concentration of airborne particles of respirable DU: particle size distribution and dust loading on the filter. First, as the sample air enters the intake 20, the particle size distribution will be measured and expressed in units of diameter (microns) and/or aerodynamic diameter, and/or activity median aerodynamic diameter (AMAD, also in units of microns). The AMAD distribution is important because the potential radiological hazard of respirable airborne DU particulates depends on the AMAD of the particles. Table 4 presents the lifetime committed effective dose for adult workers and children (1-year old) as a function of the AMAD of the aerosols.

TABLE 4

Lifetime Committed Effective Dose for Inhalation of Insoluble U-238 for Adult Workers and for 1-Year Old from the Inhalation of Insoluble U-238 (referred to as dose conversion factors or DCFs)*

| AMAD (microns) | Adult Worker (Sv/Bq) | 1 year old (Sv/Bq) |
|---|---|---|
| 0.001 | 9.9E−6 | 2.2E−5 |
| 0.003 | 2.4E−5 | 5.6E−5 |
| 0.01 | 4.2E−5 | 1.3E−4 |
| 0.03 | 3.9E−5 | 1.5E−4 |
| 0.1 | 2.1E−5 | 9.2E−5 |
| 0.3 | 1.0E−5 | 4.7E−5 |
| 1.0 | 7.3E−6 | 2.2E−5 |
| 3.0 | 7.1E−6 | 2.0E−5 |
| 5.0 | 5.7E−6 | 1.5E−5 |
| 10.0 | 3.5E−6 | 9.1E−6 |

*Values obtained from the CD accompanying ICRP 68 (1994) and ICRP 72 (1995).

The DCFs can vary by up to a factor of about 10 depending on the AMAD of the aerosol. This CAM 10 may operate on the default premise that the airborne particles of DU have an AMAD of 5 microns. This is the default assumption, which is recommended by the International Commission on Radiation Protection (ICRP) because it is representative of respirable airborne particles in general and also is associated with a relatively high radiological hazard potential as compared to particles with larger sizes.

The design of the CAM 10 includes a continuous optical air particulate monitor that measures both the airborne particulate concentration (e.g., micrograms/m³) and also the median aerodynamic diameter of the particles (which serves as a convenient surrogate for activity median aerodynamic diameter (AMAD).

It is instructive to note the relationship between the diameter of a particle and its associated aerodynamic diameter, as follows $$dac = d(p/p^*)^{1/2} \qquad \text{Equation 1}$$

where:
dac=median aerodynamic diameter of the particle of interest (microns),
d=the median diameter of the particles deposited on the filter (microns)
p=1 gram per cm³,
p*=density of the particle of interest The density of a particle of uranium dioxide is about 10.97 g/cm³. The measured median diameter of the particles deposited on the filter may be converted to median aerodynamic diameter using this equation. For example, if the median diameter of the particles deposited on the filter is one micron and has a density of 10.97 g/cm³, its median aerodynamic diameter is 0.3 microns. This conversion from measured diameter to aerodynamic diameter does not take into consideration how the radionuclides are distributed on the different sizes of the particles deposited on the web 46. Hence, this approach is only an approximation of the AMAD. The actual AMAD is unique to each air sample and cannot be determined in real time or routinely in laboratory analyses of the sample. It is the convention to treat median aerodynamic diameter as AMAD.

The CAM 10 will also continuously monitor the airborne dust concentration. Algorithms are incorporated into the CAM 10 such that, if the airborne particulate concentration exceeds a level that could substantively degrade the energy of the alpha emissions from U-238 on the web 46 (i.e., a dust depth approaching 1E-3 cm), the CAM 10 will so indicate, and the user of the CAM 10 will be alerted. Under these circumstances, the data being compiled by the CAM 10 might substantially underestimate the concentration of DU in the air and should not be used as a means to protect workers or the public. However, as described above, the CAM 10 will employ a genetic algorithm that will preclude the unacceptable buildup of particulates on the filter. In addition, since the alpha spectrum will be continually displayed, a sudden change in the shape of the spectrum (a flattening and broadening of the spectral peaks) will be indicative of the start of alpha self-attenuation and corrective action can be taken to manually lower the air flow rate and/or sample collection time.

Figure 6A:
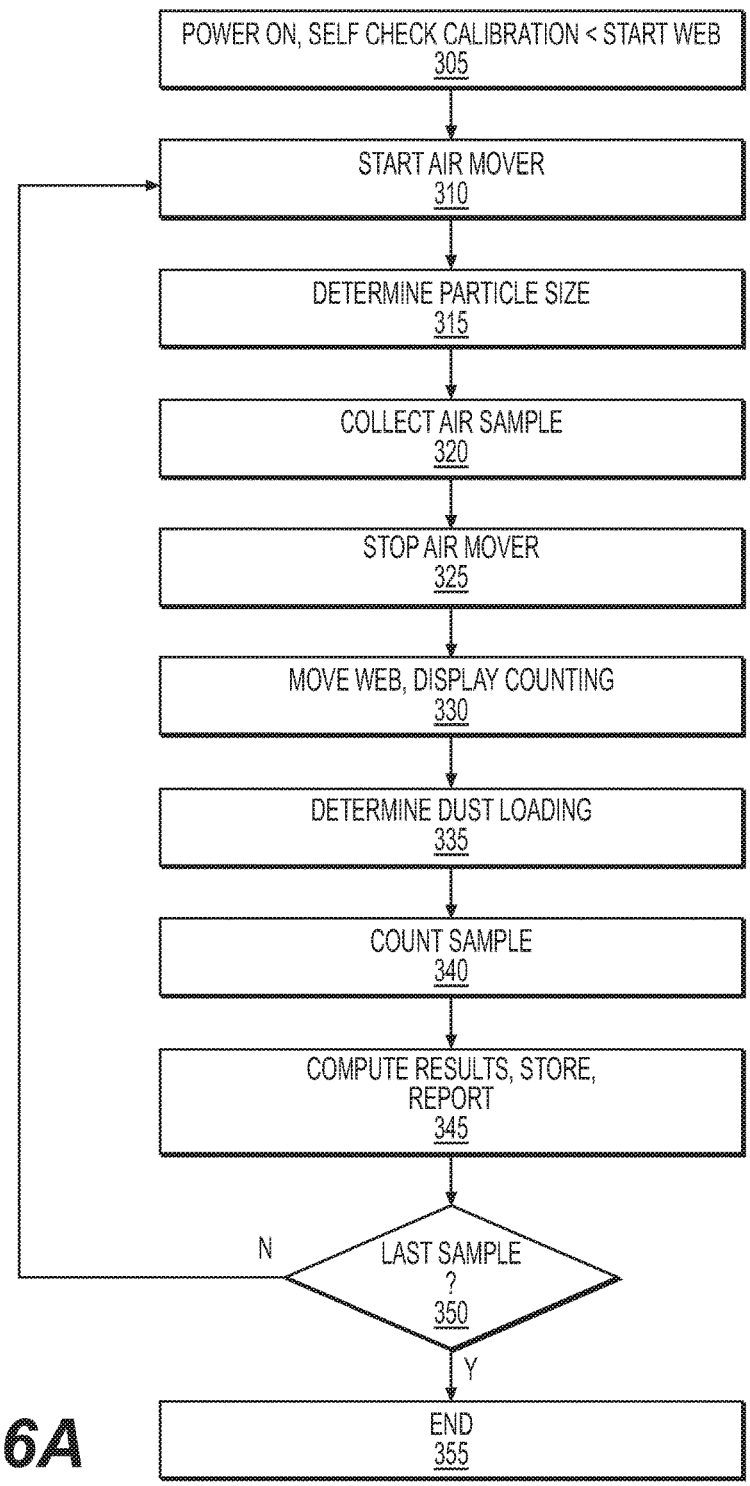
FIGS. 6A and 6B are flowcharts illustrating example operations of the monitor of FIG. 1.
Figure 6B:
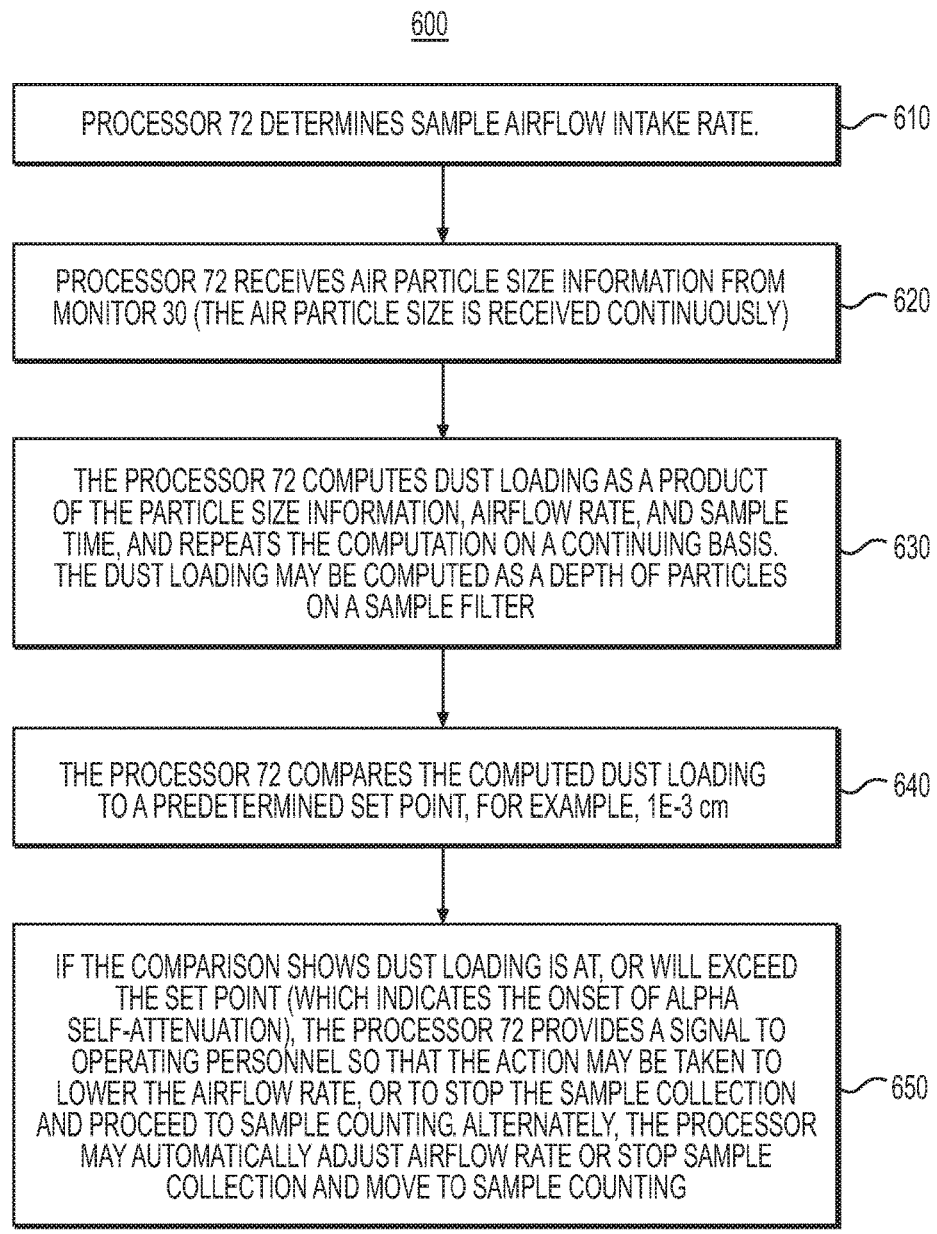

The algorithm is shown as process 600, shown in FIG. 6B. Process 600 may be executed by processor 72 (FIG. 2A) as part of process 335 of FIG. 6A. Process 600 begins in block 610, when a sampling operation of the CAM 10 begins with a specific intake airflow rate, for example 10 L/min, with the airflow provided to or determined by the processor 72. In block 620, the processor 72 receives air particle size information from monitor 30 (the air particle size is received continuously). In block 630, the processor 72 computes dust loading as a product of the particle size information, airflow rate, and sample time, and repeats the computation on a continuing basis. The dust loading may be computed as a depth of particles on a sample filter. In block 640, the processor 72 compares the computed dust loading to a predetermined set point, for example, 1E-4 cm. In block 650, if the comparison shows dust loading is at, approaches, or will exceed the set point (which indicates the possible onset of alpha self-attenuation), the processor 72 provides a signal to operating personnel so that action may be taken to lower the airflow rate, or to stop the sample collection and proceed to sample counting. Alternately, the processor may automatically adjust airflow rate or stop sample collection and move to sample counting.

In addition, it is widely recognized that inhaled or ingested uranium is both chemically and radiologically toxic. The CAM 10 is designed to quickly identify conditions where the airborne mass concentration of DU might be radiologically toxic. A vast body of literature describes the chemical toxicity of inhaled and ingested uranium (see EPA 2006 and Rostker 2017)). Section 2.2.2 of EPA 2006 explains that "DU particles and oxides retained in the body have different solubilities. The three oxides of primary concern ($UO_2$, $UO_3$, and $U_3O_8$) are relatively insoluble. Insoluble and sparingly soluble compounds are believed to have little potential to cause renal toxicity but could cause pulmonary toxicity through inhalation."

EPA 2006 also states that (also see ATSDR 2013) "ATSDR has a 'minimal risk' level for intermediate ingestion set at an oral intake of 2 μg of uranium per kg of body weight per day, though the World Health Organization (WHO) has established a tolerable daily intake (TDI) for uranium of 0.6 μg/kg body weight per day."

Note that these limits are for ingestion and for forms of uranium that would be absorbed into the blood stream. At an airborne concentration of 7 pCi/$m^3$, the mass of uranium inhaled in one hour would be:

$$7\ \text{pCi/m}^3 \times 0.037\ \text{Bq/pCi} \times 1.2\ \text{m}^3\text{/hr} \div 12440\ \text{Bq/g} = 2.5\text{E-}5\ \text{g/hr} = 25\ \mu\text{g/hr}.$$

Of this quantity, about 0.04 (or 4 percent; Federal Guidance Report No. 13 indicates that soluble forms of uranium have an absorption fraction of 0.04 for infants) would be absorbed into the blood and distributed throughout the body. Assuming a reference adult of 70 kg, an intake and absorption of 42 μg per day is required to exceed the TDI. Hence, at an airborne activity concentration of soluble uranium of 7 pCi/$m^3$, the absorption rate of uranium into the bloodstream would be about 8 μg/day or about 0.1 μg/kg-day. On this basis, the TDI would not be exceeded. However, in the above calculation, we applied an absorption factor of 0.04. It is not apparent whether this is appropriate based on the definition of TDI. If a factor of 0.04 is not applied, the intake associated with 7 pCi/$m^3$ would be 2.5 μg/kg-day, well above the TDI of 0.6 μg/kg-day.

Rostker 2017 provides a comprehensive review of DU and its potential harmful effects. With respect to chemical toxicity, Rostker 2017 states the following:

> Operational guidelines based on the MPOC [maximum permissible organ concentration] suggest temporary and permanent kidney effects may occur for inhaled soluble DU intakes above 8 milligrams (mg) and 40 mg, respectively. [32][4] These values may need to be adjusted for specific situations.[33] For example, in 10 CFR 20.1201(e),[34] the Nuclear Regulatory Commission (NRC) includes a requirement to limit soluble uranium intakes to 10 mg in a week in consideration of uranium's chemical toxicity. The NRC extended this guidance in 10 CFR 76 to assessing the adequacy of protecting the health of the public from accidents involving uranium at gaseous diffusion plants. The final guidance establishing 10 CFR 76 (59 Federal Register (FR) 48944, Sep. 23, 1994) specifically stated, "The NRC will consider whether the potential consequences of a reasonable spectrum of postulated accident scenarios exceed 0.25 Sv (25 rem), or uranium intakes of 30 mg."

[4] Reference [32] in the quote is Health Physics Society, Bioassay Programs for Uranium: An American National Standard, HPS N13.22-1995, McLean, Va., p. 34.

> Reference 33 in the quote is Harley, Naomi, Earnest Foulkes, Lee Hilborne, Arlene Hudson, and C. Ross Anthony, "A Review of the Scientific Literature as it Pertains to Gulf War Illnesses," Volume 7, "Depleted Uranium," Washington, D.C.: RAND, National Defense Research Institute, 1999, p. 33.
>
> Reference 36 in the quote is American Conference of Governmental Industrial Hygienists, 1999 TLVs and BEIs, Threshold Limit Values for Chemical Substances and Physical Agents, Biological Exposure Indices, Cincinnati, Ohio, 1999, p. 4.
>
> Few human studies verify kidney damage at these thresholds—even under exposure conditions of a single exposure to soluble uranium compounds that exceed occupational limits. These intake thresholds are worst-case benchmarks because they assume intakes of soluble uranium during a single exposure and therefore do not take into account the body's ability to eliminate 90 percent of uranium from the blood every 3 days. Gulf War veterans who were exposed to depleted uranium generally experienced repeated, small contacts with insoluble forms of uranium, an exposure scenario that would be expected to produce even less kidney damage.
>
> The Occupational Safety and Health Administration (OSHA) and American Conference of Governmental Industrial Hygienists (ACGIH) have established long- and short-term occupational exposure standards for uranium inhalation by workers based on uranium's chemical toxicity to the kidney. OSHA's Permissible Exposure Levels (PELs) and the ACGIH's Threshold Limit Values (TLV®) are based on the principle that a threshold exists below which no adverse health effects occur. As the exposure increases above the threshold, the adverse health effect becomes more severe. Both the PEL and the TLV® are "time-weighted average concentration[35] for a conventional 8-hour workday and 40-hour workweek, to which it is believed nearly all workers may be repeatedly exposed, day after day, without adverse effect."[36]

Chronic exposure of soluble natural uranium at concentrations of 7 pCi/$m^3$ for 2000 work hours per year constitutes an intake of about 25 mg.

The implications of the above discussions and calculations are that chemical toxicity could be limiting if there is reason to believe that the DU is in a form other than the insoluble forms described above. A large body of research (see the above references to the March 2009 issue of Health Physics) indicates that the DU aerosols produced during munitions testing initially could be relatively soluble, representing a possible chemical toxin. In order to ensure that the exposed individuals are not inhaling chemically toxic quantities of DU, periodic (i.e., as frequently as deemed necessary by the organization performing the testing) urine samples will be required at a site to confirm that the intake of DU experienced by the workers is not chemically toxic. If the uranium is insoluble, very little uranium will be detected in urine. If soluble, uranium will be readily detected in a 24-hour urine sample collected one month after chronic exposure. The following table presents the normalized excretion rate of uranium in urine following inhalation and ingestion of both insoluble and soluble forms of uranium.

TABLE 5

Normalized Excretion Rate (pCi/day of uranium excreted in urine and pCi/L of uranium in urine) Assuming a Chronic Intake Rate of 1 pCi/day of Uranium by Inhalation and Ingestion

| Day after Start of Chronic Intake | Inhalation | | Ingestion | |
|---|---|---|---|---|
| | Insoluble (pCi/day and pCi/L in Urine | Soluble (pCi/day and pCi/L in Urine | Insoluble (pCi/day and pCi/L in Urine | Soluble (pCi/day and pCi/L in Urine |
| 10 | 8.97E−4 and 6.4E−4 | 2.18E−1 and 0.16 | 1.52E−3 and 1.09E−3 | 1.53E−2 and 1.09E−2 |
| 20 | 1.02E−3 and 7.3E−4 | 2.37E−1 and 0.17 | 1.66E−3 and 1.19E−3 | 1.66E−2 and 1.19E−2 |
| 30 | 1.11E−3 and 7.9E−4 | 2.46E−1 and 0.16 | 1.73E−3 and 1.24E−3 | 1.73E−2 and 1.24E−2 |

The set point for the CAM 10 may be 7 pCi/m$^3$ for DU in air, which corresponds to a daily inhalation rate of 67 pCi/day (i.e., 7 pCi/m$^3$×1.2 m$^3$ per hr inhalation rate×8 hours per work day). At this inhalation rate, the concentration of uranium in urine at the end of 30 days of chronic inhalation would 0.05 pCi/L for insoluble uranium, but it would be 10.72 pCi/L for soluble uranium.

According to Manickam, et. al., 2007, "the typical minimum detectable concentration for total uranium for a 24-h urine sample is approximately 0.6 mBq/day or 0.19 μg/day." This corresponds to a urinary excretion rate of 0.0162 pCi/day or a concentration of uranium in urine of 0.012 pCi/L. The implications of this analysis are that, at the end of one month of chronic worker exposure to a uranium airborne concentration of 7 pCi/m$^3$, the concentration of uranium in urine would be 0.05 pCi/L (slightly above the limit of detection) if the inhaled uranium is insoluble. However, if the inhaled uranium is soluble, the concentration in urine would be 10.72 pCi/L. Accordingly, urine samples will be able to readily reveal whether the inhaled uranium was soluble or insoluble, and a determination could be made whether the set point for the detector is or is not protective of workers, considering the possibility of the potential chemically toxic effects of inhaled uranium.

Another feature that will aide in determining if the potential for toxicological damage to kidneys is present is the CAM 10 includes a second optical sensor upstream of the prefilter to measure the airborne concentrations of particles that are greater than 10 microns. This information will help in determining the total amount of DU being inhaled, not just the respirable size particles. This could be important if the DU is in a more chemically soluble form. Under these circumstances, the inhaled (or ingested) DU is more readily absorbed into the bloodstream, transported to internal organs in the body, and cause toxicological, as opposed to radiological damage, especially to the kidneys (as described herein).

FIGS. 6A and 6B presents example operations of the CAM 10 expressed in the form of a flowchart. In FIG. 6A, CAM 10 operation 300 begins in block 305 where the CAM 10 is powered up and various start up routines are executed and the CAM 10 is configured. The CAM 10 also executes various self-check routines and, if applicable, notifies a remote monitor that the CAM 10 is operational and operating. The operation then moves to block 310.

In block 310, the motor 52 starts to operate impeller 54 to achieve the desired airflow. The airflow to be achieved may take into account the sampling environment in terms of expected airborne DU concentration, expected dust loading on the web 46, required sample time, power mode of the CAM 10, and other factors.

In block 315, in an embodiment, the processor 72 uses a default value, such as 5 microns, for the AMAD. In another embodiment, the processor 72 executes an algorithm to approximate the value of AMAD using data collected from the site at which the CAM 10 operates. In this embodiment, the processor 72 may execute the algorithm of Equation 1, above, namely dac=d (p/p*)$^{1/2}$ using data collected by the mechanism 30.

In block 320 the processor 72 controls the CAM 10 to take an air sample for a desired duration, such as, for example, one hour.

In block 325, after the required sampling time, the processor 72 causes the motor to stop.

In block 330, the processor 72 causes the web 46 to advance to the counting location 46B, where the collected sample may wait for decay of short-lived radionuclides before counting begins. Alternately, the counting delay may be accommodated by holding the collected sample at the sampling location 46A for the decay to occur.

In block 335 the processor 72 executes an algorithm to compute dust loading on the web 46 for the collected sample. To compute dust loading, the processor 72 may execute an algorithm that takes into account sample time, sample flow rate, and default, measured, or estimated airborne particulate concentration in the sampled environment. If the derived dust concentration (dust loading) on the filter indicates possible shielding of alphas by an amount exceeding a limit, the CAM 10 may so signal to operating personal.

Note that as with all steps (blocks) in the operation 300 certain steps may be executed in orders different from that illustrated, and some steps (e.g., blocks 330 and 335) may be performed simultaneously.

In block 340, with the collected sample at the counting location 46B, and optionally a light-tight configuration of the detector housing, the processor 72 may operate the detector 60 to count the sample for alpha emissions for a designated period, such as one hour.

In block 345, the processor may compute DU concentration and may store and report data collected, measurements made, and computational results for the just completed air sample.

In block 350, the processor 72 determines if additional samples are to be collected and measured. If additional samples are to be collected and measured, the operation 300 returns to block 310. Note, however, that this determination may be made in advance of the sequence illustrated in FIG. 6A, and that if an additional air sample is to be obtained, the operation 300 returns to block 310 at the time of sample counting provided for in block 340. If no additional samples are to be obtained, the operation 300 moves to block 355 and ends. In an embodiment as part of the operation 300 executed at block 355, the CAM 10 may shut down or, alternatively, enter a low power or sleep mode, especially if operating in a battery mode, so as to conserve electrical power.

In view of the above description, Applicant has developed a novel and non-obvious design for a real time continuous air monitor for depleted uranium in the respirable range. A summary of some of the salient, novel features of the CAM 10 includes:

1. The CAM 10 is designed to detect and measure the concentration of only DU at a site in the region of interest where the only alpha-emitting manmade contamination is DU.
2. The CAM 10 continuously monitors the particle size distribution and uses this information to adjust the alarm set point for the device.
3. The CAM 10 counts the number of pulses in the U-238 region of interest and performs no spectral stripping to determine the concentration of U-238 in air.
4. The CAM 10 continually monitors the airborne dust loading on the web 46 and alerts the operator when the airborne dust concentration is so high that the airborne concentrations of DU reported by the CAM 10 would underestimate the airborne concentration of DU and cannot be used.
5. The CAM 10 can operate in a near autonomous and unattended state with all sampling operations under control of a local and/or remote processor and without the need for frequent removal of a sample filter.
6. Based on knowledge of the average hourly concentration of respirable DU dust on the filter (pCi/mg) and the data continuously monitoring the concentration of airborne dust ($mg/m^3$), real time concentrations of airborne concentrations of respirable DU ($pCi/m^3$) can be continuously estimated.

In more detail, unlike current alpha particle detectors, the CAM 10 eliminates the need to employ a spectral stripping algorithm, with its attendant uncertainties, to address the possible false positives stemming from the presence of radon and thoron progeny in an air sample. Instead, the CAM 10 eliminates the possibility of false positives by counting the alpha particles that deposit their energy in the region of interest associated with the decay of U-238. This approach for counting alpha emissions from U-238 can be accomplished because the energy of the alpha emissions associated with the decay of Po-218 and Po-214 are much higher than that of U-238 (see FIG. 3), and, as a result, the alpha emissions from Po-218 and Po-214 do not contribute to the energy region of interest for the alpha emission associated with the decay of U-238.

The CAM 10 also eliminates the need to address possible false positives from beta particles that might deposit energy and result in false positive counts. This is because beta emissions associated with any of the radionuclides that might be deposited on the web 46 will not deposit energy in the region of interest and result in false positives.

Unlike current airborne alpha instruments, the CAM 10 eliminates the need to perform spectral stripping to remove the lower end energy tails associated with alpha emitters to enable an instrument to discriminate among alpha emitters present in an air sample. The CAM 10 also eliminates the need to employ coincidence counting to take advantage of the short half-life of some alpha emitters, and accommodate counts contributed by beta emitters.

Unlike current airborne alpha instruments, the CAM 10 can accurately count alpha emissions in a dusty environment. At least two features of the CAM 10 provide this capability: the inclusion of an optional dust loading measurement device and a movable web for collecting air samples and then reading the air sample.

Confirmatory Experiments

FIGS. 1-6B and their accompanying descriptions disclose a design for a continuous air monitor (i.e., the CAM 10) intended for detecting alpha particles emitted during radioactive decay of depleted uranium. This section describes a series of experiments that were performed in a laboratory environment to demonstrate that the CAM 10 meets its design specifications under the following air sampling conditions:

an air sampling period of less than 1 hour,
an air sampling rate of less than 10 L/minute,
followed shortly thereafter by a counting time interval of less than 1 hour.

Note that these air sampling conditions are merely examples, and longer or shorter periods may be used. The inventor designed the experiments to show that under these sampling and counting conditions, the CAM 10 will be able to continuously and unambiguously detect and quantify the concentration of U-238 and any other isotope of uranium that might be present in the air at concentrations that could result in committed effective doses to radiation workers due to inhalation in excess of 10% of the radiation protection standards (i.e., 500 mrem/yr effective dose commitment) if the exposures persist over a 2000-hour work year.[5] In addition, the CAM 10 will achieve this objective in the presence of a chronic dust loading up to about 1 to 5 $mg/m^3$. As noted herein, such a dust loading is relatively high compared to typical airborne dust loadings indoors and outdoors under quiescent conditions where the respirable dust concentrations are on the order of tens of micrograms per cubic meter. As a reference point, the threshold limit value for occupational exposure to respirable dust (i.e., <10 micron aerodynamic diameter, referred to as particulates not otherwise regulated) is 5 $mg/m^3$, and the limit for total dust particulates not otherwise regulated is 15 $mg/m^3$ (see 29 CFR 1910.1000 Table Z-1, Limits for Air Contaminants). This means that in working environments where the airborne dust loading is higher than these values, some type of intervention is required.

[5] 10 CFR 20.1201 (a) states that "The licensee shall control the occupational dose to individual adults, except for planned special exposures under Part 20.1206, to the following dose limits (1) Annual limit, which is the more limiting of—(1) the total effective dose equivalent being equal to 5 rem (0.05 Sv); or (ii) the sum of the deep dose equivalent and the committed dose equivalent to any individual organ or tissue other than the lens of the eye being equal to 50 rems (0.5 Sv).

In addition, under the same set of sampling and counting conditions noted above, the CAM 10 will be able to clearly and unambiguously continuously detect and quantify the concentration of U-238 and any other isotope of uranium that might be present in ambient air at concentrations that exceed 50% of the concentrations that could result in committed effective doses in excess of the radiation protection standards for members of the public from all potential exposure pathways (i.e., 50 mrem/yr to the most sensitive members of the general population).[6]

[6] 1—CFR 20.1301 states that "(a) Each licensee shall conduct operations so that (1) The total effective dose equivalent to individual members of the general public from the licensed operation does not exceed 0.1 rem (1 millisievert) in a year, exclusive of the dose contributed from background radiation, from any medical administration the individual has received, from exposures to individuals administered radioactive material and released in accordance with part 35.75 from voluntary participation in medical research programs, and from the licensees disposal of radioactive material into sanitary sewage in accordance with Part 20.2003.

Anticipated Performance

The anticipated performance of the CAM 10 includes three factors:

1. No counts in the region of interest when no radioactivity is deposited on the filter In theory, no counts in the energy region of interest (i.e., >3 MeV to 8 MeV) should be recorded after one hour of counting if no radioactive material is present on the filter medium.

2. Naturally occurring alpha-emitters ubiquitously present in outdoor and indoor air can be detected, accurately counted, and most importantly, will not contribute counts to the uranium energy region of interest (i.e., 3.0 to 4.8 MeV).

Naturally occurring radon is ubiquitous in outdoor air at about 0.1 to 1 pCi/L, while the concentrations of radon indoors typically range from 0.1 to occasionally several pCi/L. The short-lived progeny of radon are reported to be at about 50% of the radon concentration both indoors and outdoors. UNSCEAR 1993 presents an extensive discussion of this matter. The presence of radon and its progeny represent a challenge to the ability of the CAM 10 to achieve its design objectives because, in theory, the alpha-emitting short-lived progeny of radon can contribute alpha counts to the alpha emission region of interest for uranium, resulting in false positives.

In theory, if ambient air in the laboratory is passed through a filter medium for 1 hour at a flow rate of 10 l/min and then immediately counted on the solid-state detector for 1 hour, the only naturally occurring alpha emitters present in the air in the lab that could be deposited on the filter media in any substantive quantity are Po-214 (20-minute half-life with E$\alpha$=7.833 MeV) and Po-218 (3-minute half-life with E$\alpha$=6.114 MeV).

These counts would occur in the energy region of interest for these radionuclides. Specifically, assuming that the resolution of the CAM 10 solid state detector is about 200 keV, as cited in its specifications, virtually all of the Po-218 counts would occur in the energy range of above about 5.7 MeV to a maximum of 6.114 MeV, with the peak at 6.114 MeV. For Po-214, virtually all the Po-214 counts would occur in the energy range of no less than about 7.0 MeV to a maximum of 7.883 MeV, with the peak at 7.883 MeV.

The inventor did not expect any counts from these two radionuclides to occur in the energy range of the uranium isotopes associated with depleted uranium (which is expected to occur in an energy range no less than 3.0 MeV to no greater than 4.8 MeV, with a peak at 4.2 MeV) because the inventors did not expect the alphas from Po-214 and Po-218 to be substantively attenuated under the conditions of sampling and counting the air particulate samples collected and counted by the CAM 10. The inventor believes this to be the case because of the following:

The Po-214 and Po-218 atoms are deposited on the surface of the filter media and do not embed inside the matrix of the filter media because the filter media was selected to avoid deposition of the particles deep into the filter media, where, if such deposition were to occur, the alpha particles could be attenuated by the filter media; and The amount of the air particulates deposited on the filter media, along with the isotopes of polonium, is expected to be quite small because the concentration of the airborne dust in the laboratory was determined to range from 2 to 20 µg/m$^3$. At this concentration, the amount of dust deposited on the filter media was expected be:

10 µg/max 10 L/min×60 min×1E-3 m$^3$/L×1E-3 mg/µg=0.006 mg.

Assuming that the density of the dust on the filter media is about 2 g/cm$^3$ and the area of the filter paper is 450 mm$^2$, the thickness of the dust deposit on the filter media is estimated as:

0.006 mg/450 mm$^2$×100 mm$^2$/cm$^2$÷(2 g/cm$^2$×1000 mg/g)=6.67E-7 cm.

According to the literature summarized herein, the range of alpha emitters in the 5 MeV range in media with a density of about 2 g/cm$^3$ is about 1E-3 cm. Hence, no appreciable attenuation of the alpha emissions from particulates on the filter media is anticipated due to the dust deposited on the filter media. In a similar manner, the alpha particles are not anticipated to be attenuated by the approximate 1 to 2 mm air gap between the filter media and the CAM 10 solid state detector because the median range in air of alpha particles (i.e., the distance an alpha particle will travel) is typically about 3 cm.

3. The airborne concentration of isotopes of uranium associated with depleted uranium can be continuously detected and quantified at the desired level of sensitivity, and the alpha emissions will not be substantively attenuated by the presence of the DU or elevated levels of other airborne particulates, as might occur at DU remediation and/or munitions testing sites.

One design objective of the CAM 10 is to be able to accurately measure the concentration of airborne U-238 at a concentration of 7 pCi/m$^3$ when present in the air with a known concentration of respirable particles (mg/m$^3$). Let us assume the following:

the airborne concentration of particulates at a site is 1 mg/m$^3$; and the air is sampled for 1 hour at a rate of 10 L/min.

Under these conditions, the amount of airborne particles deposited on the filter media would be 0.6 mg (i.e., 1 mg/m$^3$×10 L/min×1E-3 m$^3$/L×60 min/hr). This amount of particulate material would have a thickness of about 6.67E-5 cm (0.6 mg/450 mm$^2$×100 mm$^2$/cm$^2$×1E-3 g/mg÷2 g/cm$^3$=6.67E-5 cm). This thickness of fine particles on the filter media was not anticipated to attenuate the 4.2 MeV alphas associated with the decay of U-238 because the range of these alpha particles is on the order of 1E-3 cm in the soil particulates on the filter media. The implications are that the count obtained from each individual filter of the CAM 10 would be reliable for several hours assuming that the average concentration of the airborne dust in the respirable range during sampling is about 1 mg/m$^3$. The airborne dust loading of respirable particles will be continuously monitored and alarm when the total dust loading on the filter media becomes so high that it has the potential to substantially attenuate the alpha particles emitted from the uranium on the filter media. In addition, the genetic algorithm will help to preclude the unacceptable buildup of dust particles on the filter.

The amount of uranium oxide that would be deposited onto the filter media would be 4.2 pCi (7 pCi/m$^3$×10 L/min×1E-3 m$^3$/L×60 min/hr=4.2 pCi). The number of counts on the CAM 10 associated with 4.2 pCi of uranium counted for 1 hour would be 140 counts (4.2 pCi×0.037 dis/sec-pCi×3600 sec/hr×0.25=140 counts in one hour). These are the number of counts the inventors anticipated in the region of interest for U-238, which is about 3.0 to 4.8 MeV. The number of counts should not degrade until the dust loading on the filter media approaches the range of the alpha particles in the surrogate soil deposited on the filter media (i.e., about 1E-3 cm).

One of the inventor's design objectives is to be able to detect the presence of airborne respirable U-238 at a concentration of 0.24 pCi/m$^3$. This is the concentration associated with a dose of 50 mrem per year to the limiting member of the general public from all potential exposure pathways. This concentration is about 30 times lower than the 7 pCi/m$^3$ detection limit established for the protection of radiation workers. Hence, the number of counts in the region of interest associated with this airborne concentration of respirable U-238 is 140/30=4.7 counts following 1 hour of sampling at a sample rate of 10 L/min followed by counting the sample on the CAM 10 for 1 hour.

Design and Results of Actual Testing of the CAM 10 Breadboard

To confirm the detectors performance, the inventor built a bread board model of the detector and ran a number of preliminary experiments to confirm the predicted performance and capabilities of the detector. The bread board model confirmed the following performance aspects of the CAM 10:

Ability to count DU alphas;

Ability to distinguish DU alphas from alphas from other isotopes such as polonium 214; and Ability of the optical sensor to provide reliable measurements of respirable concentrations of airborne particulates.

Disclosed below are the bread board model and certain of its components, the experimental designs, and the experimental results.

Figure 8:
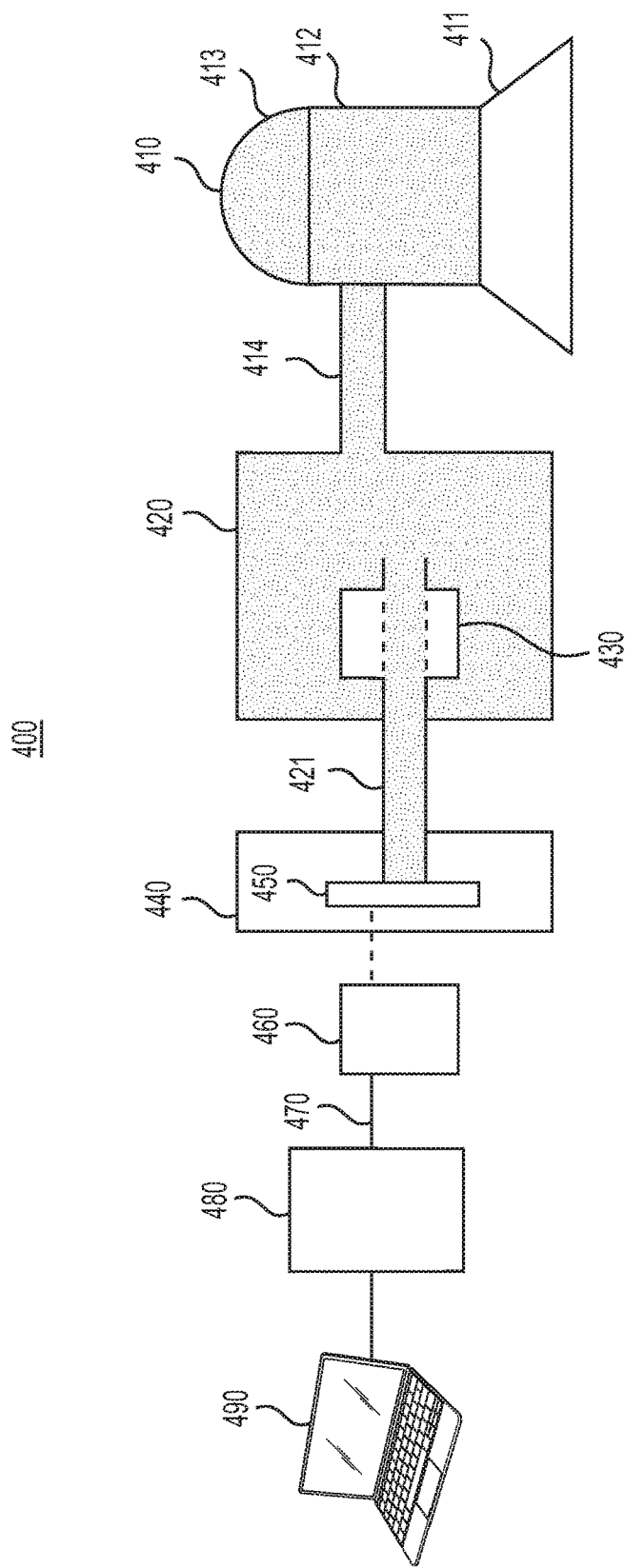

The bread board model was configured to include important components of the CAM 10 of FIG. 1. FIGS. 8-12 show bread board 400, it's components, and results of experiments using the bread board 400. In FIG. 8, bread board 400 includes aerosol production mechanism 410, particulate sampling chamber 420, counting chamber 440, electronics and analysis chain 480, and processor system 500. The aerosol production mechanism 410 includes vibration table 411, aerosol chamber 412, cover 413, and tube 414. To conduct the experiments disclosed herein, the inventor introduced specific quantities of soil particles, into the aerosol chamber 412 and then operated the vibration table 411 to vibrate the aerosol chamber 412, thereby causing the particles to become airborne. The tube is kept short and straight to minimize particle deposition in the tube 414.

Figure 9C:
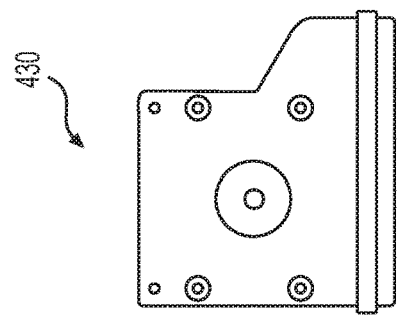
Figure 9B:
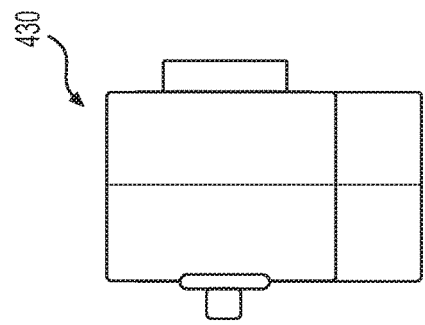
Figure 9A:
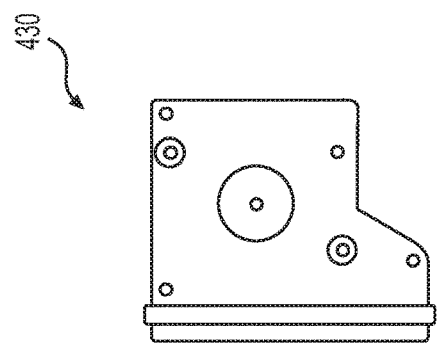

The particulate sampling chamber 420 receives the aerosol particles from the tube 414, directing the aerosol particles into optical particle counter 430, described in more detail with respect to FIGS. 9A-9C. After counting in the particle counter 430, the particles move through tube 421 to sampling chamber 440.

The sampling chamber 440 includes filter mechanism 450 and an air mover (not shown). Following sampling, a filter media is moved to the solid state detector 460 where the sample is counted. The detector 460 is coupled to, electronic output 470 and 480, and processor system 490. The detector 460 is shown in more detail in FIGS. 10 and 11. The processor system 490 executes machine instructions such as those disclosed with respect to FIGS. 6A and 6B to control some components of the bread board 400 and to display experimental results.

The first set of experiments made use of the naturally occurring alpha emitters present in the air in the laboratory. A brief explanation of the source of naturally occurring alpha emitters both indoors and out door is instructive in terms of understanding the first set of experiments performed to confirm that the CAM 10 achieves its design objectives.

Figure 15:
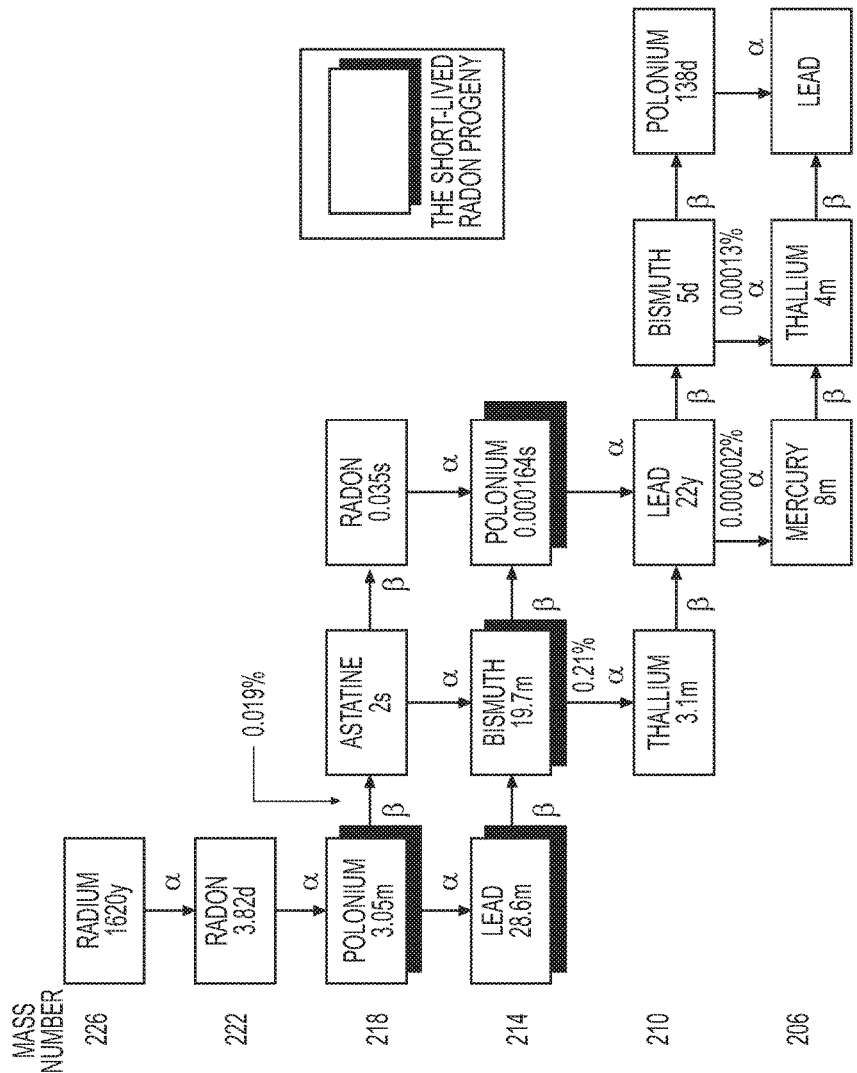

FIG. 15 presents the naturally occurring decay series for radium-226 (Ra-226) and its progeny. All soil contains naturally occurring Ra-226, which decays to the noble gas radon-222 (Rn-222). As Ra-226 decays, it transforms to Rn-222 which then leaves the soil and enters the atmosphere. If there is a structure sitting on the soil, the Rn-222 enters the structure. Each atom of Rn-222 then undergoes a series of disintegrations, producing what is referred to as radon progeny, some of which emit beta particles with energies well below the energy of interest of the alpha emission associated with the decay of DU. The electronic pulses produced in the detector by these beta particles are of no concern to the CAM-10 because a discriminator can be used to eliminate any electronic pulses of electrons produced in the detector that are below the energy region of interest of the CAM 10. However, two of these progeny, Po-218 and Po-214, are of special interest to the inventor because they are alpha emitters that have energies that are above the energy region of interest for detecting the alpha emissions from DU. The presence of these radionuclides in air can result in false positives when trying to detect the amount of DU that may be in the atmosphere. In addition, these two alpha emitters are useful in testing the performance of the CAM 10.

Before beginning the experiments, a calibration test was run with an Am-241 source to confirm that the solid state semiconductor was performing correctly. FIG. 19 presents the spectra obtained from counting the Am-241 source.

This spectra is best understood by comparing it to the energy spectra of the alpha emissions associated Am-241, as provided in Table 7.

TABLE 7

| Intensity of Alpha Emissions from Am-241 (T1/2 = 432.2 years)* | |
|---|---|
| Alpha Energy | Relative Intensity per disintegration |
| 5.388 | 0.014 |
| 5.443 | 0.128 |
| 5.486 | 0.852 |
| 5.512 | 0.0020 |
| 5.443 | 0.0034 |
| 5.308 | 0.000339 |

*From Table 8.14 of Shleien, et. al, 1998

From a practical perspective, it can be assumed that 0.852 of the alpha emitted by Am-241 have an energy of 5.486 MeV and 0.128 of the alpha emissions have an energy of 5.443 MeV. The other alpha emissions are very infrequent and cannot be discerned as separate peaks on the spectra. In addition, the full width at half maximum (FWHM) appears to be about 0.025 keV, as expected as specified in the documentation provided by the detector vendor. This spectra confirms that the detector 60 is performing as expected.

The first set of experiments involve drawing samples of air through a filter and depositing the air particulates, including the Po-218 and Po-214, onto the filter and then counting the alpha activity on the filter and creating an alpha spectrum of these emissions. The experiments were conducted using the breadboard model, shown conceptually in FIG. 8. Components of the breadboard model are shown in FIGS. 9A-12.

FIGS. 9A-9C illustrate optical particle counter 430. The counter 430 used in the bread board 10 is the Alphasense OPC-N2 Particle Counter manufactured by Sensor Technology House, 300 Avenue West, Skyline 120, Great Notley, Essex CM77 7AA, United Kingdom.

Figure 11:
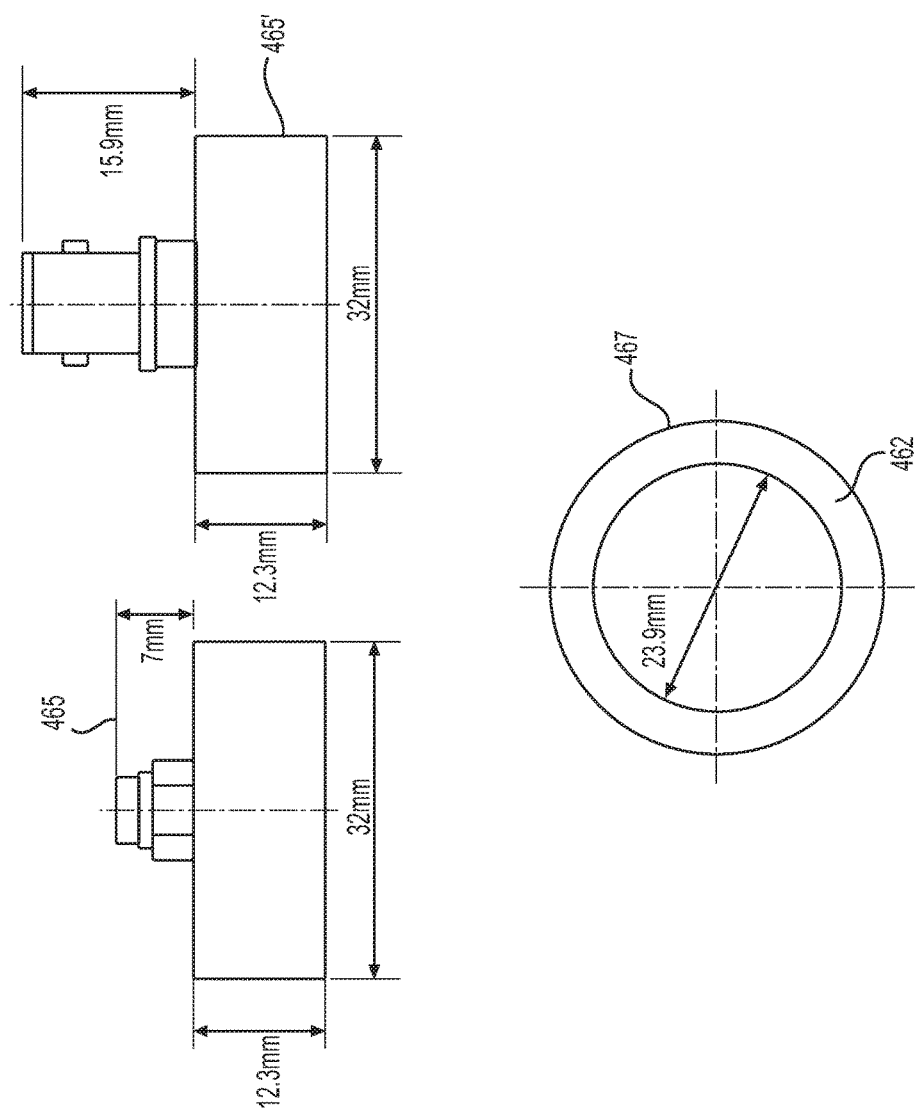

FIGS. 10 and 11 illustrate the silicon oxide solid state detector 460. The detector 460 is a SIID-450 model obtained from Baltic Scientific Instruments, LTD, Ganiber Dambis 26, Riga, Latvia. In FIG. 10, detector 460 includes top and bottom housing elements 461 and 463. The housing elements, when assembled, enclose detector element 465 and solid-state surface barrier 467.

FIG. 11 is a schematic of the detector showing its dimensions and two versions with different electrical connectors (465 and 465'). The active sensitive area of the detector 460 is a disc 467 with a diameter of 23.9 mm and a surface area of 450 mm². Noteworthy is that the face of the semiconductor sensor has protective film (not shown) with a thickness of 0.05 micron. This inert/transparent layer protects the active area of the detector 460 and allows the surface to be cleaned. In addition, the protective film is extremely thin and will not attenuate alpha particles striking the surface of the detector 460.

The housing 461/463 also has a cylindrical rim 462 of approximately 1 mm. This rim allows a filter containing radioisotopes to be placed against the face of the detector 460, but offset at a distance of 1 mm. This separation is useful because the filter containing particles of radionuclides will be placed facing the surface of the detector 460 but will not touch and contaminate the active area of the detector 460. However, since the distance between the filter and the sensitive area of the detector 460 is only 1 mm, the air gap is not large enough to attenuate alpha particles emitted from radionuclides deposited on the filter surface. As discussed above, the range of typical alpha particles (5 MeV) is about 30 mm in air.

Table 8 presents the fundamental performance specification of the solid state semi-conductor detector 460. Noteworthy is the alpha energy resolution of <25 keV[7] full width at half maximum (FWHM) at an alpha energy of 5.1 MeV. This is important because any alpha emitters deposited into the filter, such as Po-214 and Po-218, will not deposit counts in the energy region of interest for alpha emission from DU.

[7] This is the FWHM for the detector itself. However, after passing the pulses through the amplifier and other electronics, the actual FWHM observed in the spectra is closer to 200 keV.

TABLE 8

Detector Performance Specifications

| Parameter | Value |
|---|---|
| Area of Si implanted detector's open part, mm | 450 |
| Thickness of Si implanted detector, μm | 400 |
| Dead layer, μm | 0.25 |
| Reversed leakage current at 70 V, nA | ≤30 |
| Depletion bias, V | 25 |
| Detector capacity at depletion bias, pF | ≤200 |
| Optimal operating voltage of Si implanted detector, V | 50 |
| Alpha energy resolution (opened)-FWHM (241 Am), keV at 5.1 MeV (241 Am), keV | ≤18 |
| Alpha energy resolution (300 nm Al metalized)-FWHM at 5.1 MeV (241 Am), keV | ≤25 |
| Dimensions of detector unit, height, mm × diameter, mm | 12.3 × 32 |

Alpha (and beta particles) that strike the surface barrier 467 of the detector 460 will deposit their energy in the sensitive layer of the detector and generate pulses of electrons that will drift to the conduction band of the detector, where they will be swept away through the coaxial cable 469 to the electronic and analysis chain 480. See FIG. 12.

Figure 12:
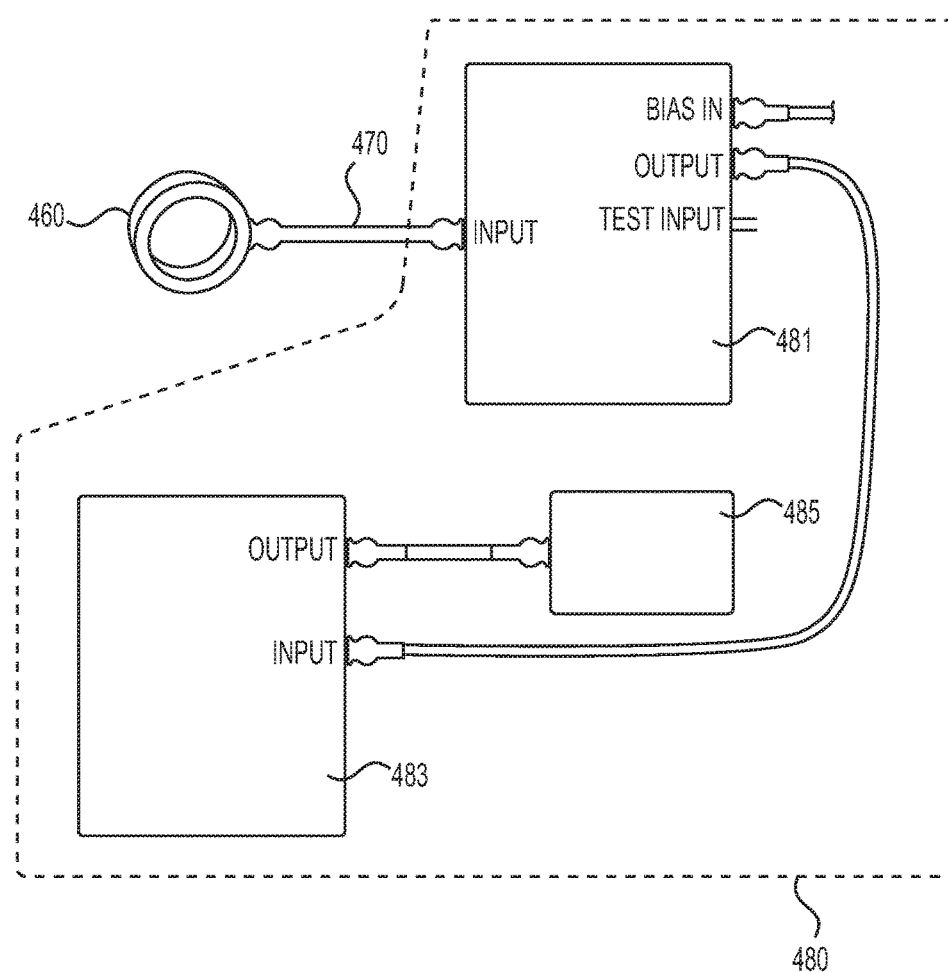

FIG. 12 shows the electronic and analysis chain 480, which includes charge sensitive preamplifier 481, shaping amplifier 483, and oscilloscope 485. The preamplifier 481 is a Cremat CR-110 single channel charge sensitive preamplifier, obtained from Cremat Inc., 950 Watertown St. #3, West Newton, Mass. The shaping amplifier 483 is a Cremat CR-200-1 Gaussian Shaping Amplifier. The output of the shaping amplifier 483 is a time-stamped sequence of amplified and shaped pulses of electrons individually having voltages that are directly proportional to the energy of the alpha or beta particles that deposit their energy in the sensitive volume of the surface barrier detector 430.

Each of these pulses is sent to oscilloscope 485, which counts each arriving pulse (in units of millivolts), sorts the pulses according to a pulse size, and then converts the pulse size using a voltage to MeV conversion factor, as described above for Am-241.

Figure 13:
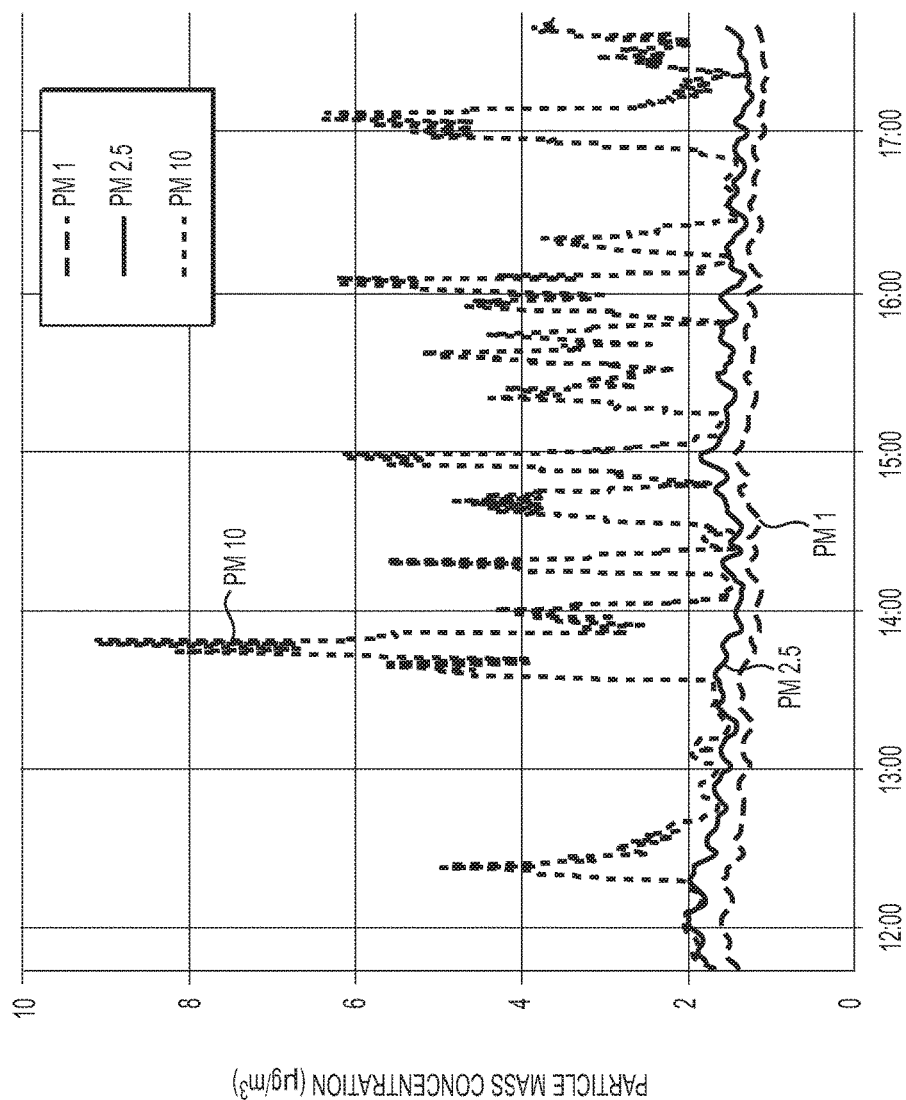

FIG. 13 illustrates aerosol concentration in a laboratory (lab) housing the CAM 10 bread board model. Line PM 10 provides the measured concentration of aerosols in the lab with an aerodynamic diameter of 10 microns or less over a several hours period. Measurements were made every second. Note that, in these measurements, the concentration of respirable aerosols varies over a range of 2 to 10 microns/m³. In other such measurements, the respirable aerosol concentrations ranged from about 2 to 25 micrograms per m³. From a review of the literature, this range of concentrations of respirable particles in indoor air is commonplace. The concentration of PM 10 appears to be higher when individuals are walking around the lab, and then go down to about 2 microgram/m³ (lines PM 1 and 2.5) when no one is in the lab.

In order to evaluate the performance of the CAM 10 breadboard, a number of simple experiments were performed.

Experiment 1

Figure 16:
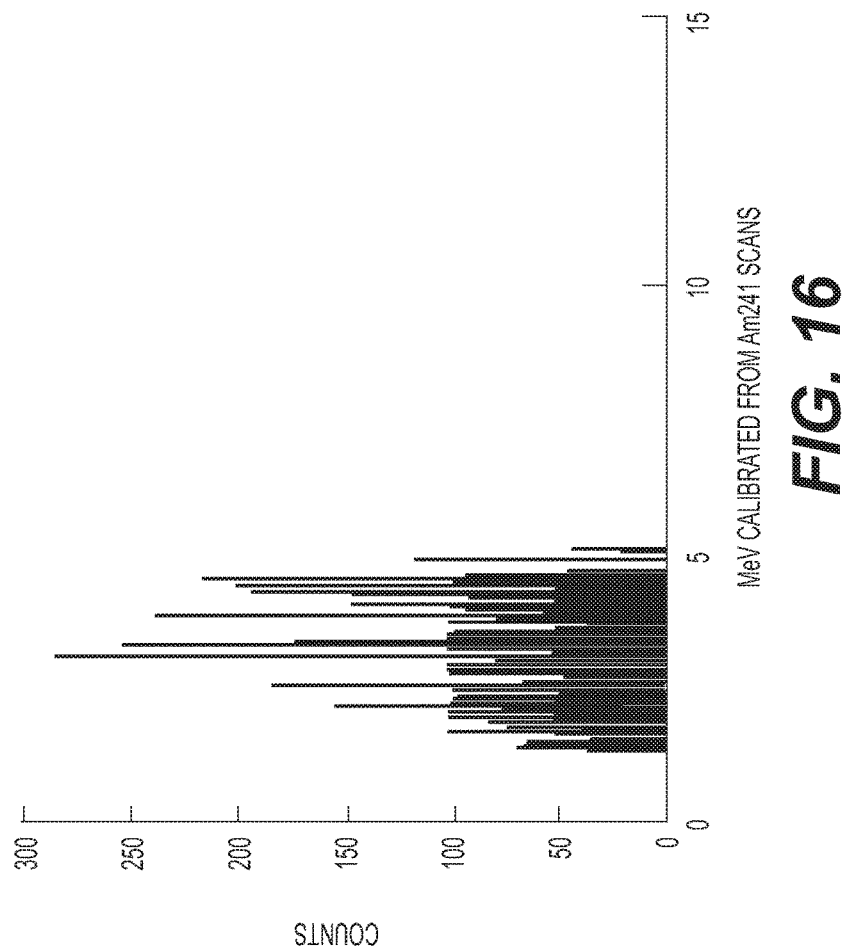

In the first experiment, approximately 2 to 5 mg of naturally uranium oxide powder was directly deposited onto the filter medium and counted for 10 minutes. FIG. 16 shows the spectrum obtained from this experiment in which 2-5 mg of uranium oxide powder deposited on filter media and counted for 10 minutes.

The alpha energies emitted by natural uranium include primarily 4.8 and 4.2 MeV alphas from U-238 and U-234. However, the spectrum is somewhat irregular between about 2 to 5 MeV because of two factors. The first is that the uranium oxide powder has a range of diameters from several microns to approximately a mm (information as provided by the vendor). In addition, a crude energy conversion factor was employed to convert millivolts (which is the output of the counter) to MeV. Experiments are continuing to obtain a more refined spectrum. Noteworthy is that no counts are observed outside the region of interest for the alphas from uranium, and, more importantly, clear and unambiguous counts from the uranium alpha emissions are being obtained from the solid state detector and its associated signal processing, as described above.

The total number of counts integrated under the uranium spectrum is 9250 counts. The following is a check on the reasonableness of this total count assuming that about 2 mg of uranium oxide was deposited onto the filter medium (assuming 25% efficiency of the detector as specified by the vendor): 2 mg×683 pCi/mg×0.037 dis/sec per pCi×10 min× 60 sec/min×0.25=7581 counts.

Given the uncertainty in the number of mg of uranium oxide deposited on the filter and the uncertainty in efficiency, these results certainly appear to confirm that the CAM 10 breadboard performed adequately.

Experiment 2

Figure 17:
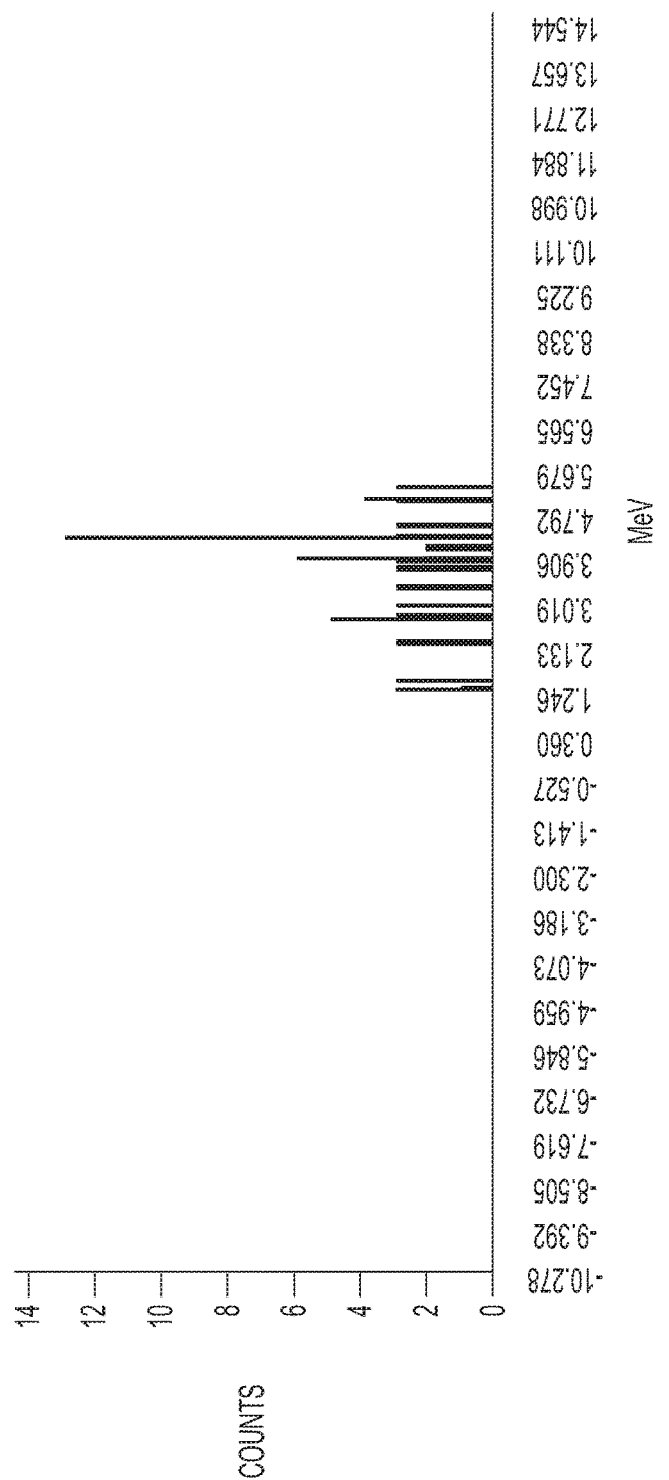

A second experiment with uranium was performed by first placing about 500 mg of uranium oxide powder in a mortar and pestle and grinding down the powder. The ground uranium oxide powder was then passed through a 5 micron filter and particles that passed through the filter were collected. About 1 microgram of the <5 micron uranium oxide powder was paced on the filter and recounted for 1 second and then for 1 minute. FIG. 17 (Spectra associated with a 1 second count of approximately 1 mg of naturally occurring uranium oxide powder with particles less than 5 micron in diameter) presents the spectra obtained from these alpha counts. A total of 94 alpha counts were obtained for the 1 second count. The expected number of counts for a 1 mg sample would be as follows:

$$1 \text{ mg} \times 683 \text{ pCi/mg} \times 0.037 \text{ dis/sec per pCi} \times 0.25 = 76.3 \text{ counts.}$$

The observed total count of 94 per second is compatible with an anticipated total count of 76.3 counts. The small difference is likely due to uncertainty in the amount of uranium oxide powder placed on the filter.

The alpha energy of the U-238 and U-234 that make up the majority of the uranium in the sample are 4.2 and 4.8 MeV. The spectrum seems reasonable, except that, given the 200 keV FWHM of the detector, we should see very few or no counts below about 3.0 MeV. However, there appear to be some low energy stragglers. Additional work is being done to refine the signal processing to reduce straggling in the spectra.

Experiment 3

Figure 14:
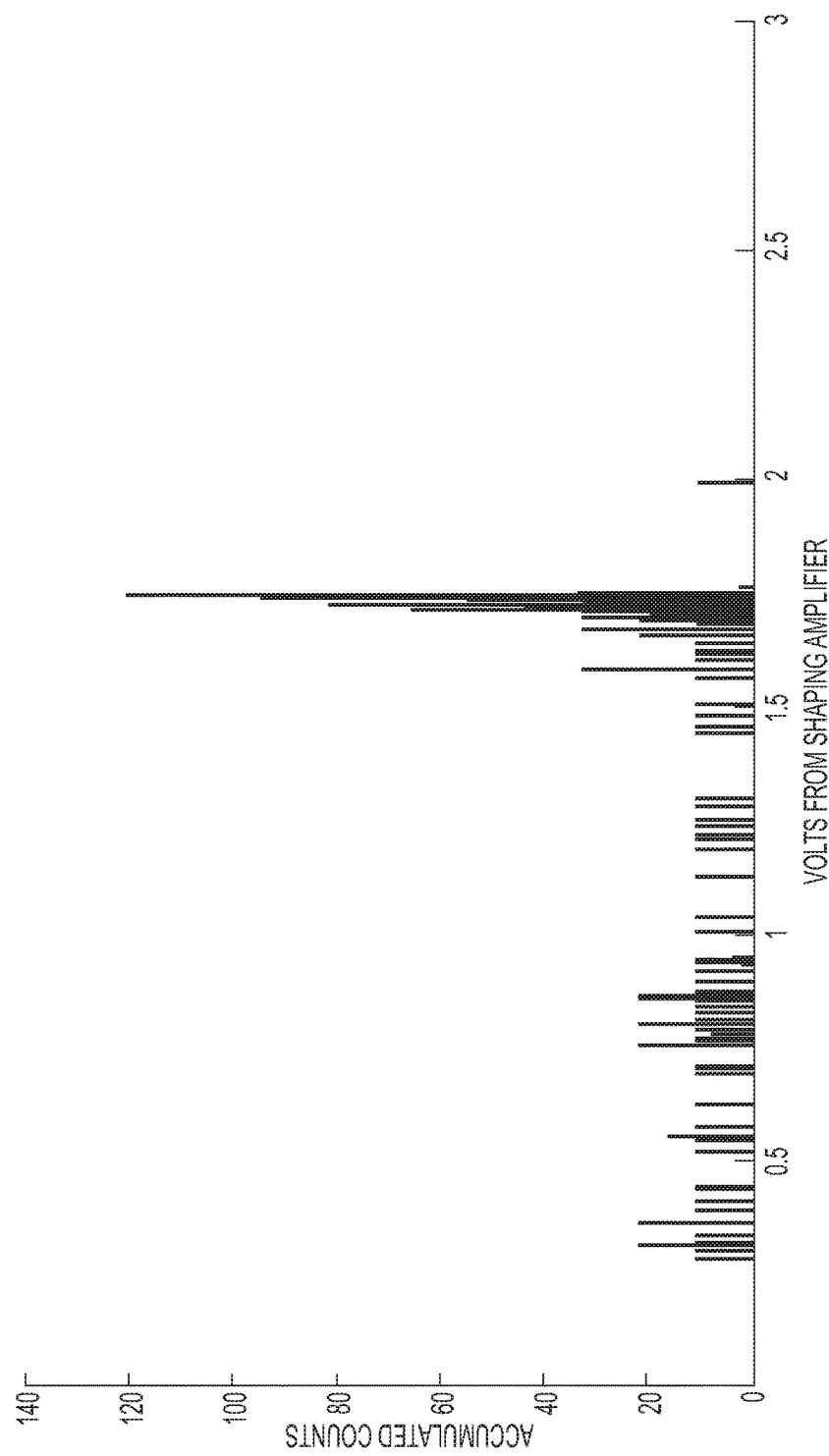

An air sample was collected for several hours and then counted after a delay to allow the Po-218 with a 3-minute half-life to decay away. This left the Bi-214 (relatively low energy beta emitter with a 19-minute half-life) and its progeny, Po-214, with its 7.7 MeV alpha emissions. FIG. 14 presents the spectrum associated with this air sample. The figure clearly shows the presence of Po-214. However, there are also several smaller lines to the left of the Po-214 alpha peak that are electronic pulse artifacts that will be removed after corrections are made to signal nose associated with the counting electronics.

CONCLUSION

Current alpha monitors are designed to, and do, operate in a specific environment that often requires use of a vacuum chamber and algorithms for spectral stripping; the monitors are intended to be used indoors and primarily in support of operations involving a number of different alpha emitters. In contrast, the CAM 10 is intended for use in a very different environment and is designed with features different from and not suggested by current monitoring devices.

REFERENCES

In describing the CAM 10, the preceding specification cites the following references:

ATSDR 2013. *Toxicological Profile for Uranium*, U.S. Department of Health and Human Services, Agency for Toxic Substances and Disease Registry, February 2013.

Besic, L., I. Muhovic, A. Adna, A. Kurtovic-Kozaric 2017, Meta-analysis of depleted uranium levels in the Nalkan region, Journal of Environmental Radioactivity 172 (2017) 207-217.

Cheng, Y. S., J. L. Kenoyer, R. A. Guilmette, Yung Sung Cheng and, M. A. Parkhurst, 2009. *Physiochemical Characterization of Capstone Depleted Uranium Aerosols II: Particle Size Distribution as a Function of Time*, Health Physics, Volume 96, Number 4, pp 266-275. March 2009.

Choy, C. C., G. P. Korfatis, and X. Meng, 2006. *Removal of Depleted Uranium from Contaminated Soil. J. Hazard Mater.* 2006 Aug. 10; 136(1): 53-60. Epub 2005 Dec. 28.

Crean, D. E., F. R. Livens, M. Sajih, M. C. Stennett, D. Goleman, C. N. Broca, and N. C. Hyatt, "Remediation of soils contaminated with particulate depleted uranium by multi-stage chemical extraction," Journal of Hazardous Materials 263 (2013 (382-390, Aug. 2, 2013).

DOE 2009. *DOE Standard: Guide of Good Practices for Occupational Radiological Protection in Uranium Facilities*, U.S. Department of Energy, DOE-STD-1136-2004. Washington D.C.

EPA 1999. *Cancer Risk Coefficients for Environmental Exposure to Radionuclides—Federal Guidance Report No. 13*. U.S. Environmental Protection Agency. EPA 402-R-99-001, September 1999.

EPA 2006, *Depleted Uranium-Technical Brief*, Radiation Protection Division of the Office of Radiation and Indoor Air of the Environmental Protection Agency.

Hindin, R., D. Brugge, and B. Panikkar 2005. "Terratogenicity of depleted uranium aerosols: A review from an Epidemiological perspective," Environmental Health: A Global Access Science Source 2005, 4:17 Aug. 22, 2005.

Holmes, T. D., R. A. Guilmette, Yung Sung Cheng, M. A. Parkhurst, and M. D. Hoover 2009. *Aerosol Sampling System for Collection of Capstone Depleted Uranium Particles in a High-Energy Environment*, Health Physics, Volume 96, Number 4, pp 221-237. March 2009.

ICRP 68 (1994), *Dose Coefficients for Intakes of Radionuclides by Workers*, International Commission on Radiation Protection. Annals of the ICRP Volume 24, No. 4, 1994. ISSN 0146-6453. Pergamon.

ICRP 72 (1995), *Age-Dependent Doses to the Members of the Public from Intake of Radionuclides—Part 5 Compilation of Ingestion and Inhalation Coefficients*, International Commission on Radiation Protection. Annals of the ICRP Volume 26, No. 1, 1995. Pergamon.

Kennedy, W. E. Jr. and D. L. Strenge, *Residual Radioactive Contamination from Decommissioning," Technical Basis for Translating Contamination Levels to Annual Total Effective Dose Equivalent*, Prepared by Pacific Northwest Laboratory, Battelle Memorial Institute, prepared for the U.S. Nuclear Regulatory Commission, NUREG/CR-5512, PNL-7994, Vol. 1, October 1992; see page 6.10).

Krupka, K. M., M. A. Parkhurst, K. Gold, B. W. Arey, E. D. Jenson, and, R. A. Guilmette, 2009. *Physiochemical Characterization of Capstone Depleted Uranium Aerosols III: Morphologic and Chemical Oxide Analysis*, Health Physics, Volume 96, Number 4, pp 276-291. March 2009.

Manickam, S. Sdraulig, and R. A. Tinker, *Method Design and Validation for the Determination of Uranium Levels in Human Urine Using High-Resolution Alpha Spectrometry*, Journal of Environmental Radioactivity, Vol. 99, pp 4891-501, 2008.

Miller, G., Y. S. Cheng, R. J. Traub, T. T. Little, and R. Guilmette, 2009. *Methods Used to Calculate Doses Resulting from Inhalation of Capstone Depleted Uranium Aerosols*, Health Physics, Vol. 96, No. 3, p. 306-327, March 2009.

Mohammes, A. A., A Sh. Hussien, and N. F. Tawfiw, 2008. "Assessment of depleted uranium concentration in selected Iraqi soils", Journal of Al-Nahrain University, Volume 11(1), pp 74-81, April 2008.

NCRP 1987. *Exposure of the Population in the United States and Canada from Natural Background Radiation*, National Council on Radiation Protection and Measurements, NCRP Report No. 94, Dec. 30, 1987.

Parkhurst, M. A., E. G. Daxon. G. M. Lodde, F. Szron, R. A. Guilmette, L. E. Roszell, G. A. Falco, and C. B. McKee, "Depleted Uranium Aerosol Doses and Risks: Summary of U.S. Assessments," prepared for the US Army by Battelle under the Chemical and Biological Defense Information Analysis Center, Task 241, DO 0189, Aberdeen Md., PNWD-3476. October 2004

Rostker, 2000. Environmental Exposure Report, Depleted Uranium in the Gulf (II). Special Assistant to Gulf War Illness, Department of Defense, 200179-0000002, Ver 2.0; http://wwwgilflink.osd.mil/du_ii/.

Sarap, N. B. et al. 2014, "Environmental radioactivity in southern Serbia at locations where depleted uranium was used," Arh Hig Rad Toksikol 2014: 65: 189-197. DOI: 10.2478/10004-1254-65-2014-2427.

Seiler, F. A., G. J. Newton, and R. A. Guilmette, *Continuous Monitoring for Airborne α Emitters in a Dusty Environment*, in Health Physics, Vol 54. No. 5 (May) pp 503-515, 1988.

Stevens DC, Toureau AER. *The Effect of Dust Loading on the Shape of Alpha Pulse Height Spectra of Air Sample Filters*, Atomic Energy Research Establishment Report. Berkshire, UK: AERE; Report No. AERE-R 4249; 1963.

UNSCEAR 1993, *Sources and Effects of Ionizing Radiation, United Nations Scientific Committee on the Effects of Atomic Radiation*. UNSCEAR 1993 Report to the General Assembly, with Scientific Annexes. United Nations, New York, 1993.

Yu, C. et. al., 1993a, *Data Collection handbook to Support Modeling the Impacts of Radioactive Material in Soil*, Environmental Assessment and Information Sciences Division, Argonne National Laboratory, ANL/EAIS-8, April 1993.

Yu. et. al., 1993b, "Manual for Implementing Residual Radioactivity Material Guidelines Using RESRAD Version 5," Environmental Assessment and Information Sciences Division, Argonne National Laboratory, ANL/EAD/LD-2, September 1993.

Zhang, Y. Shao, and N. Huang, *Measurement of Dust Deposition Velocity in a Wind Tunnel Experiment*, Atmos. Chem. Phys., 14, 8869-8882, 2014.

Certain of the devices shown in the Figures include a computing system. The computing system includes a processor (CPU) and a system bus that couples various system components including a system memory such as read only memory (ROM) and random access memory (RAM), to the processor. Other system memory may be available for use as well. The computing system may include more than one processor or a group or cluster of computing system networked together to provide greater processing capability. The system bus may be any of several types of bus structures including a memory bus or memory controller, a peripheral bus, and a local bus using any of a variety of bus architectures. A basic input/output (BIOS) stored in the ROM or the like, may provide basic routines that help to transfer information between elements within the computing system, such as during start-up. The computing system further includes data stores, which maintain a database according to known database management systems. The data stores may be embodied in many forms, such as a hard disk drive, a magnetic disk drive, an optical disk drive, tape drive, or another type of computer readable media which can store data that are accessible by the processor, such as magnetic cassettes, flash memory cards, digital versatile disks, cartridges, random access memories (RAM) and, read only memory (ROM). The data stores may be connected to the system bus by a drive interface. The data stores provide nonvolatile storage of computer readable instructions, data structures, program modules and other data for the computing system.

To enable human (and in some instances, machine) user interaction, the computing system may include an input device, such as a microphone for speech and audio, a touch sensitive screen for gesture or graphical input, keyboard, mouse, motion input, and so forth. An output device can include one or more of a number of output mechanisms. In some instances, multimodal systems enable a user to provide multiple types of input to communicate with the computing system. A communications interface generally enables the computing device system to communicate with one or more other computing devices using various communication and network protocols.

The preceding disclosure refers to flowcharts and accompanying descriptions to illustrate the embodiments represented in FIGS. 1-4B. The disclosed devices, components, and systems contemplate using or implementing any suitable technique for performing the steps illustrated. Thus, the flowchart of FIG. 4 is for illustration purposes only and the described or similar steps may be performed at any appropriate time, including concurrently, individually, or in combination. In addition, many of the steps in the flow chart may take place simultaneously and/or in different orders than as shown and described. Moreover, the disclosed systems may use processes and methods with additional, fewer, and/or different steps.

Embodiments disclosed herein can be implemented in digital electronic circuitry, or in computer software, firmware, or hardware, including the herein disclosed structures and their equivalents. Some embodiments can be implemented as one or more computer programs, i.e., one or more modules of computer program instructions, encoded on computer storage medium for execution by one or more processors. A computer storage medium can be, or can be included in, a computer-readable storage device, a computer-readable storage substrate, or a random or serial access memory. The computer storage medium can also be, or can be included in, one or more separate physical components or media such as multiple CDs, disks, or other storage devices. The computer readable storage medium does not include a transitory signal.

The herein disclosed methods can be implemented as operations performed by a processor on data stored on one or more computer-readable storage devices or received from other sources.

A computer program (also known as a program, module, engine, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

I claim:

1. A continuous, real time monitor for airborne depleted uranium (DU) particles in a respiratory range, comprising:
an air mover that pulls an air sample into the monitor at a desired airflow rate to deposit particles in the air sample on a filter media;
a prefilter sized to pass only respirable range particles in the air sample, wherein the respirable range comprises particles having a maximum aerodynamic diameter of 10 microns;
a first particle detector configured to provide a first airborne dust concentration and a first size distribution of the particles contained in the air sample;
a movable filter web through which the air sample is pulled, the movable filter web supporting a plurality of the filter media upon which the particles in the air sample are deposited;
a solid state detector configured to measure alpha activity emitted from DU particles in the air sample and deposited on the filter media; and
a processor configured to execute a program of machine instructions, the program contained on a non-transient computer-readable storage medium, and configured to:
control movement of the movable filter web to place the movable filter web in a first position in which the air sample passes thereby depositing the particles and a second position at which the emitted alpha activity is detected and measured by the solid state detector, and
compute, using the first airborne dust concentration, a dust loading on the filter media.

2. The monitor of claim 1, wherein the processor is configured to execute the program of machine instructions configured to:
maintain the movable filter web in the first position for a first time period, and
maintain the movable filter web in the second position for a second time period with the solid state detector activated to count the alpha activity emitted from the DU particles.

3. The monitor of claim 1, wherein the processor is further configured to control the movable filter web in the second position for a third time period to allow decay of short-lived radionuclides before counting the alpha activity from the DU particles.

4. The monitor of claim 3, wherein the first size distribution comprises airborne particles having a maximum aerodynamic diameter of 10 microns.

5. The monitor of claim 4, wherein the processor is configured to execute a genetic algorithm configured to:
compute a thickness of dust on the filter media, comprising the processor configured to determine a product of the dust loading on the filter media, and a dust density on the filter media;
compare the computed dust thickness to a desired set point; and
adjust one or more of the sample time and the sample airflow rate based on the comparison.

6. The monitor of claim 5, wherein the processor is configured to repeat the computing, comparing, and adjusting processes of the genetic algorithm periodically during the sampling time.

7. The monitor of claim 4, wherein the processor is further configured to execute the genetic algorithm configured to:
compute a shortest air sample time and an associated sample airflow rate that results in a deposition of DU on the filter media that is indicative of an ambient airborne concentration of respirable DU reaching a variable setpoint.

8. The monitor of claim 7, wherein the filter media comprises a porous material that will not repel the particles nor allow the particles to become embedded in or absorbed by the filter media.

9. The monitor of claim 7, further comprising a second air particle detector upstream of the prefilter that is configured to determine a second airborne concentration and a second size distribution of the particles contained in the air sample, the second size distribution comprising aerodynamic diameters of particles less than 50 microns.

10. A continuous alpha monitor, comprising:
an air intake, comprising:
an air mover,
an air intake prefilter that limits particulates in the air intake to an aerodynamic diameter of 10 microns or less, and
a particle detector mounted downstream of the air intake prefilter, the air particle detector configured to provide a first airborne dust concentration and a first distribution of aerodynamic diameters of particulates in air passing the prefilter, the particulates including depleted uranium particulates;
a movable sample filter web configured to collect the particulates;
a solid state detector configured to detect alpha radiation emitted by the collected particulates;
a processor configured to execute machine instructions embodied on a non-transient computer-readable storage medium to compute a dust loading; and
the processor configured to compute an indication of alpha concentration detected by the solid state detector.

11. The continuous alpha monitor of claim 10, wherein the movable sample filter web supports a plurality of sample filters, and
a processor-controlled motor configured to move the movable sample filter web;
wherein the solid state detector comprises:
a movable light shield;
wherein the solid state detector is spaced away from a surface of a sample filter by a gap of three millimeters or less; and
wherein the particle detector comprises:
a light source, and
a light scattering detector configured to measure aerodynamic diameters of the particulates based on a detected angle of scattered light.

12. The continuous alpha monitor of claim 10, further comprising a static eliminator configured to minimize static buildup on the movable sample filter web.

13. The continuous alpha monitor of claim 11, further comprising a sample filter removal station positioned downstream of the solid state detector, the sample filter removal station comprising a sample filter lifting device configured to lift a sample filter from the movable sample filter web.

14. The continuous alpha monitor of claim 10, further comprising a second particle detector upstream of the prefilter configured to determine a second airborne dust concentration and a second size distribution comprising aerodynamic diameters of particulates less than 50 microns.

15. The continuous alpha monitor of claim 11, wherein the processor is configured to execute the program of machine instructions configured to:
control movement of the movable sample filter web to place the filter media in a first position in which the air sample passes thereby depositing the particulates and a second position at which the emitted alpha radiation is detected and measured by the solid state detector, and compute a dust thickness on the filter media.

16. The continuous alpha monitor of claim 15, wherein the processor is configured to execute the program of machine instructions configured to:
maintain the movable sample filter web in the first position for a first time period, and
maintain the movable sample filter web in the second position for a second time period with the solid state detector activated to count the alpha radiation from decay of the depleted uranium particles.

17. The continuous alpha monitor of claim 16, wherein the processor is further configured to control the movable second position for a third time period to allow decay of short-lived radionuclides before counting the alpha radiation.

18. A continuous, real time monitor for sampling and counting alpha particles emitted from decay of depleted uranium, comprising:
a processor-controlled air mover that is configured to pull an air sample into the monitor at a desired airflow rate to deposit particles in the air sample on a filter media;
a prefilter sized to pass only respirable range particles in the air sample, wherein the respirable range comprises particles having a maximum aerodynamic diameter of 10 microns;
a first particle detector configured to provide a first airborne dust concentration and a first size distribution of the particles contained in the air sample, the first airborne dust concentration provided as an input to a processor to enable computation of dust loading on the filter media accumulated during a sampling operation;
a processor-controlled movable filter web through which the air sample is pulled, the movable filter web supporting a plurality of the filter media upon which the particles in the air sample are deposited; and
a processor-controlled solid state detector configured to measure alpha activity emitted from DU particles in the air sample and deposited on the filter media.

19. The monitor of claim 18, wherein the processor is configured to execute a genetic algorithm configured to:
compute a thickness of dust on the filter media, comprising the processor determining a product of the first airborne dust concentration and a dust density on the filter media;
compare the computed dust thickness to a desired set point;
adjust one or more of the sample time and the sample airflow rate based on the comparison; and
wherein the processor is configured to repeat the computing, comparing, and adjusting processes of the genetic algorithm periodically during the sampling time.

20. The monitor of claim 19, wherein the processor is further configured to execute the genetic algorithm configured to:
compute a shortest air sample time and an associated sample airflow rate that results in a deposition of depleted uranium on the filter media that is indicative of an ambient airborne concentration of respirable depleted uranium reaching a variable setpoint.

* * * * *